US010869873B2

(12) United States Patent
Einav et al.

(10) Patent No.: US 10,869,873 B2
(45) Date of Patent: Dec. 22, 2020

(54) METHODS AND COMPOSITIONS FOR TREATING VIRAL DISEASES

(71) Applicant: The Board of Trustees of the Leland Stanford Junior University, Palo Alto, CA (US)

(72) Inventors: Shirit Einav, Palo Alto, CA (US); Rina Barouch-Bentov, Palo Alto, CA (US); Gregory Neveu, Palo Alto, CA (US); Amotz Zivav, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 15/150,293

(22) Filed: May 9, 2016

(65) Prior Publication Data
US 2017/0000802 A1 Jan. 5, 2017

Related U.S. Application Data

(62) Division of application No. 14/362,993, filed as application No. PCT/US2012/068167 on Dec. 6, 2011, now Pat. No. 9,364,484.
(Continued)

(51) Int. Cl.
A61K 31/404 (2006.01)
A61K 31/517 (2006.01)
(Continued)

(52) U.S. Cl.
CPC .......... A61K 31/553 (2013.01); A61K 31/404 (2013.01); A61K 31/517 (2013.01);
(Continued)

(58) Field of Classification Search
CPC .. A61K 31/553; A61K 31/404; A61K 31/517; C12Q 1/18; Y02A 50/30; G01N 2500/10
See application file for complete search history.

(56) References Cited

U.S. PATENT DOCUMENTS 3,760,984 A 9/1973 Theeuwes
3,845,770 A 11/1974 Theeuwes et al.
(Continued)

FOREIGN PATENT DOCUMENTS

EP 1 256628 A3 11/2003
WO WO 94/24314 A1 10/1994
(Continued)

OTHER PUBLICATIONS

Randhawa, Effect of Tyrosine Kinase Inhibitors on Polyomavirus BK Replication, Am. J. Clin. Pathol., 2010, 134, pp. 916-920.*
(Continued)

Primary Examiner — Savitha M Rao
Assistant Examiner — Andrew P Lee
(74) Attorney, Agent, or Firm — James S. Keddie; Bozicevic, Field & Francis LLP

(57) ABSTRACT

The invention provides a method for treating viral infections and coinfections through the use of inhibitory agents that prevent a unique viral structural protein motifs from binding to host proteins from the clathrin adaptor proteins family and subsequently preventing viral replication.

8 Claims, 35 Drawing Sheets
Specification includes a Sequence Listing.

| Host protein | Motif | | | | | | Partner |
|---|---|---|---|---|---|---|---|
| Consensus | ±/X | $X_1$ | $X_2$ | Y | $X_3$ | $X_4$ | ± |
| TFR | P | L | S | Y | T | R | F | AP2M1 |
| P-selctin | L | G | T | Y | G | V | F | AP2M1 |
| HLA-DM | H | S | S | Y | T | P | L | AP2M1 |

Related U.S. Application Data

(60) Provisional application No. 61/567,491, filed on Dec. 6, 2011.

(51) Int. Cl.
   *A61K 31/553* (2006.01)
   *C12C 1/18* (2006.01)

(52) U.S. Cl.
   CPC ............ *C12C 1/18* (2013.01); *G01N 2500/10* (2013.01); *Y02A 50/30* (2018.01)

(56) References Cited

U.S. PATENT DOCUMENTS

| | | | |
|---|---|---|---|
| 3,916,899 | A | 11/1975 | Theeuwes et al. |
| 3,923,426 | A | 12/1975 | Theeuwes |
| 3,987,790 | A | 10/1976 | Eckenhoff et al. |
| 3,995,631 | A | 12/1976 | Higuchi et al. |
| 4,016,880 | A | 4/1977 | Theeuwes et al. |
| 4,036,228 | A | 7/1977 | Theeuwes |
| 4,111,202 | A | 9/1978 | Theeuwes |
| 4,111,203 | A | 9/1978 | Theeuwes |
| 4,203,440 | A | 5/1980 | Theeuwes |
| 4,203,442 | A | 5/1980 | Michaels |
| 4,210,139 | A | 7/1980 | Higuchi |
| 4,211,771 | A | 7/1980 | Witkowski et al. |
| 4,327,725 | A | 5/1982 | Cortese et al. |
| 4,350,155 | A | 9/1982 | Thompson |
| 4,360,019 | A | 11/1982 | Portner et al. |
| 4,487,603 | A | 12/1984 | Harris |
| 4,627,850 | A | 12/1986 | Deters et al. |
| 4,692,147 | A | 9/1987 | Duggan |
| 4,695,623 | A | 9/1987 | Stabinsky |
| 4,725,852 | A | 2/1988 | Gamblin et al. |
| 4,865,845 | A | 9/1989 | Eckenhoff et al. |
| 4,897,471 | A | 1/1990 | Stabinsky |
| 5,057,318 | A | 10/1991 | Magruder et al. |
| 5,059,423 | A | 10/1991 | Magruder et al. |
| 5,112,614 | A | 5/1992 | Magruder et al. |
| 5,137,727 | A | 8/1992 | Eckenhoff |
| 5,234,692 | A | 8/1993 | Magruder et al. |
| 5,234,693 | A | 8/1993 | Magruder et al. |
| 5,382,657 | A | 1/1995 | Karasiewicz et al. |
| 5,443,450 | A | 8/1995 | Kratoska et al. |
| 5,643,207 | A | 7/1997 | Rise |
| 5,728,396 | A | 3/1998 | Peery et al. |
| 5,814,019 | A | 9/1998 | Steinbach et al. |
| 5,820,589 | A | 10/1998 | Torgerson et al. |
| 5,951,974 | A | 9/1999 | Dickson, Jr. |
| 5,976,109 | A | 11/1999 | Heruth |
| 5,981,709 | A | 11/1999 | Greenwald et al. |
| 5,985,305 | A | 11/1999 | Peery et al. |
| 5,990,276 | A | 11/1999 | Zhang et al. |
| 6,017,328 | A | 1/2000 | Fischell et al. |
| 6,143,715 | A | 11/2000 | Llinas-Brunet et al. |
| 6,171,276 | B1 | 1/2001 | Lippe et al. |
| 6,198,966 | B1 | 3/2001 | Heruth |
| 6,241,704 | B1 | 6/2001 | Peterson et al. |
| 6,265,380 | B1 | 7/2001 | Tung et al. |
| 6,277,830 | B1 | 8/2001 | Ganguly et al. |
| 6,323,180 | B1 | 11/2001 | Llinas-Brunet et al. |
| 6,329,379 | B1 | 12/2001 | Llinas-Brunet et al. |
| 6,329,417 | B1 | 12/2001 | Llinas-Brunet et al. |
| 6,410,531 | B1 | 6/2002 | Llinas-Brunet et al. |
| 6,420,380 | B2 | 7/2002 | Llinas-Brunet et al. |
| 6,423,695 | B1 | 7/2002 | Tam et al. |
| 6,440,985 | B1 | 8/2002 | Bailey et al. |
| 6,464,687 | B1 | 10/2002 | Ishikawa et al. |
| 6,475,180 | B2 | 11/2002 | Peterson et al. |
| 6,479,508 | B1 | 11/2002 | Beaulieu et al. |
| 6,512,954 | B2 | 1/2003 | Fox et al. |
| 6,534,523 | B1 | 3/2003 | Llinas-Brunet et al. |
| 6,608,027 | B1 | 8/2003 | Tsantrizos et al. |
| 6,608,067 | B1 | 8/2003 | Tung et al. |
| 6,617,309 | B2 | 9/2003 | Tung et al. |
| 6,624,290 | B2 | 9/2003 | Zhang |
| 6,642,204 | B2 | 11/2003 | Llinas-Brunet et al. |
| 7,655,419 | B2 | 2/2010 | Glenn et al. |
| 2002/0058635 | A1 | 5/2002 | Averett |
| 2003/0019067 | A1 | 1/2003 | Rapp |
| 2003/0186895 | A1 | 10/2003 | Llinas-Brunet et al. |
| 2003/0187018 | A1 | 10/2003 | Llinas-Brunet et al. |
| 2006/0199174 | A1 | 9/2006 | Glenn et al. |
| 2007/0065427 | A1 | 3/2007 | Freeman et al. |
| 2007/0122378 | A1 | 5/2007 | Freeman et al. |
| 2008/0118511 | A1 | 5/2008 | Freeman et al. |
| 2011/0052536 | A1 | 3/2011 | Einav et al. |
| 2011/0229484 | A1 | 9/2011 | Baumert et al. |

FOREIGN PATENT DOCUMENTS

| | | |
|---|---|---|
| WO | WO 97/27840 A1 | 8/1997 |
| WO | WO 99/07733 A2 | 2/1999 |
| WO | WO 99/07734 A2 | 2/1999 |
| WO | WO 00/06529 A1 | 2/2000 |
| WO | WO 00/09543 A2 | 2/2000 |
| WO | WO 00/09558 A1 | 2/2000 |
| WO | WO 00/59929 A1 | 10/2000 |
| WO | WO 02/060926 A1 | 10/2000 |
| WO | WO 01/47883 A1 | 5/2001 |
| WO | WO 01/90121 A2 | 11/2001 |
| WO | WO 02/06246 A1 | 1/2002 |
| WO | WO 02/057287 A2 | 7/2002 |
| WO | WO 02/057425 A2 | 7/2002 |
| WO | WO 02/069903 A2 | 9/2002 |
| WO | WO 2002/089731 A2 | 11/2002 |
| WO | WO 02/100846 A1 | 12/2002 |
| WO | WO 02/100851 A2 | 12/2002 |
| WO | WO 03/000254 A1 | 1/2003 |
| WO | WO/2003/007945 A1 | 1/2003 |
| WO | WO/2003/010140 A2 | 2/2003 |
| WO | WO/2003/010141 A2 | 2/2003 |
| WO | WO 2005/032329 A2 | 4/2005 |
| WO | WO 2006/133326 A1 | 12/2006 |
| WO | WO 2007/018692 A1 | 2/2007 |
| WO | WO 2008/021928 A2 | 2/2008 |
| WO | WO2010034670 A2 | 4/2010 |

OTHER PUBLICATIONS

Liu P, Bartz R, Zehmer J, Ying Y-s, Zhu M, et al. (2007) Rab-regulated interaction of early endosomes with lipid droplets. Biochim Biophys Acts 1773: 784-793.

Jong X, Li H, Derdowski A, Ding L, Burnett A, et al. (2005) AP-3 Directs the Intracellular Trafficking of HIV-1 Gag and Plays a Key Role in Particle Assembly. Cell 120: 663-674.

Barouch Bentov R, Sauer K (2011). Mechanisms of drug resistance in kinases. Expert Opin Investig Drugs 20: 153-208.

Knight ZA, Shokat KM (2005) Features of Selective Kinase Inhibitors. Chem Biol 12: 621-637.

Lupberger J, Zeisel M, Xiao F, Thumann C, Fofana I, et al. (2011) EGFR and EphA2 are host factors for hepatitis C virus entry and possible targets for antiviral therapy. Nat Med 17: 589-595.

Bardou Jacquet E, Lorho R, Guyader D (2012) Kinase inhibitors in the treatment of chronic hepatitis C virus. Gut 60: 879-880.

Gottwein JM, Scheel TKH, Jensen TB, Ghanem L, Bukh J (2011). Differential Efficacy of Protease Inhibitors Against HCV Genotypes 2a, 3a, 5a, and 6a NS3/4A Protease Recombinant Viruses. Gastroenterology 141: 1067-1079.

Fischer T, Stone RM, DeAngelo DJ, Galinsky I, Estey E, et al. (2010) Phase IIB Trial of oral Midostaurin (PKC412), the FMS-Like Tyrosine Kinase 3 Receptor (FLT3) and Multi-Targeted Kinase Inhibitor, in Patients with Acute Myeloid Leukemia and High-Risk Myelodysplastic Syndrome With Either Wild-Type or Mutated FLT3. J Clin Onc 28: 4339-4345.

Rock EP, Goodman V, Jiang JX, Mahjoob K, Verbois SL, et al. (2007) Food and Drug Administration Drug Approval Summary: Suntinib Malate for the Treatment of Gastrointestinal Stromal Tumor and Advanced Renal Cell Carcinoma. Oncologist 12: 107-113.

(56) References Cited

OTHER PUBLICATIONS

Shepherd FA, Rodrigues Pereira J, Ciuleanu T, Tan EH, Hirsh V, et al. (2005) Erlotinib in Previously Treated Non Small-Cell Lung Cancer. N Engl J Med 353: 123-132.
Kelley R, Ko A (2008) Erlotinib in the treatment of advanced pancreatic cancer. Biologics 2: 83-95.
Prados MD, Lamborn KR, Chang S, Burton E, Butowski N, et al. (2006) Phase 1 study of erlotinib HCl alone and combined with temozolomide in patients with stable or recurrent malignant glioma. Neuro Oncol 8: 67-78.
Jilg N, Chung RT (2012) Adding to the toolbox: Receptor tyrosine kinases as potential targets in the treatment of hepatitis C. J Hepatol 56: 282-284.
Schwartz M, Chen J, Janda M, Sullivan M, den Boon J, et al. (2002) A Positive-Strand RNA Virus Replication Complex Parallels Form and Function of Retrovirus Capsids. Mol Cell 9: 505-514.
Remy I, Michnick SW (2007) Application of protein-fragment complementation assays in cell biology. Biotechniques 42 137-145.
Rual J-F, Hirozane-Kishikawa T, Hao T, Berlin N, Li S, et al. (2004) Human ORFeome version 1.1: a platform for reverse proteomics. Genome Res 14: 2128-2135.
Blight KJ, Kolykhalov AA, Rice CM (2000) Science 290, 1972-1974, 2000.
Einav S, Elazar M, Danieli T, Glenn JS (2004) A nucleotide binding motif in hepatitis C virus (HCV) NS4B mediates HCV RNA replication. J Virol 78: 11288-11295.
Cocquerel L, Meunier JC, Pillez A, Wychowski C, Dubuisson J (1998) A retention signal necessary and sufficient for endoplasmic reticulum localization maps to the transmembrane domain of hepatitis C virus glycoprotein E2. J Virol 72: 2183-2191.
Camus et al., Malec Biol Cell 18:3193-3203, 2007.
Berlioz-Torrent et al., J Virol 73:1350-1361, 1999.
Byland et al., Molec Biol Cell 18:414-425, 2007.
Wyss et al., J Virol 75:2982-2992, 2001.
Ohno et al., Virology 238:305-315, 1997.
Boge et al., J Biol Chem 273:15773-15778, 1998.
Egan et al., J Virol 70:6547-6556, 1996.
Rowell et al., J Immunol 155:473-488, 1995.
Lodge et al., EMBO J 16:695-705, 1997.
Deschambeault et al., J Virol 73:5010-5017, 1999.
Blight et al. J Virol 76:13001, 2002.
Zhang et al. J Virol 78:1448, 2004.
Gennaro (2000), "Remington: The Science and Practice of Pharmacy"; Pharmaceutical Dosage Forms and Drug Delivery Systems (1999).
Remington's Pharmaceutical Sciences, 17th edition, 1985.
Merck Index, compound No. 8199, Eleventh Edition.
Program and Abstracts of the 54th Annual Meeting of the American Association for the Study of Liver Diseases (AASLD, 2003).
Ricotta et al., Journal of Cell Biology 156, 791-795, 2002.
Sigal et al., Nature 477, 95-98, 2011.
Wei et al., Antimicrobial agents and chemotherapy 46:1896-1905, 2002.
Zhou et al., Cell Host & Microbe 4:495-504, 2008.
Tscherne et al., J Virol 80, 1734-1741, 2006.
Sefton; Crit Rev Biomed Eng. 1987;14(3):201-40.
Buchwald et al. Diabetes Care. Mar.-Apr. 1980;3(2):351-8.
Saudek et al. Diabetes Educ. Jan.-Feb. 1989;15(1):44-9.
Langer Science. Sep. 28, 1990;249(4976):1527-33.
Gretch et al. Ann Intern Med. Sep. 1, 1995;123(5):321-9.
Yokley et al. Anal Chem. Aug. 1, 2002;74(15):3754-9.
Pause et al. J Biol Chem. May 30, 2003;278(22):20374-80. Epub Mar. 19, 2003.
Lamarre et al. Nature. Nov. 13, 2003;426(6963):186-9. Epub Oct. 26, 2003. Erratum in: Nature. Nov. 20, 2003;246.
Kwong et al American Association for the Study of Liver Diseases 2003 Conference Boston, MA Oct. 24-28, 2003.
Ma Y, Yates J, Liang Y, Lemon SM, Yi M (2008) N53 Helicase Domains Involved in Infectious Intracellular Hepatitis C Virus Particle Assembly. J Virol 82: 7624-7639.
Steinmann E, Penin F, Kallis S, Patel A, Bartenschlager R, et al. (2007) Hepatitis C virus p7 protein is crucial for assembly and release of infectious virions. PLoS Pathog 3: e103-e103.
Jones CT, Murray CL, Eastman DK, Tassello J, Rice CM (2007) Hepatitis C Virus p7 and NS2 Proteins Are Essential for Production of Infectious Virus. J Virol 81: 8374-8383.
Stapleford KA, Lindenbach BD (2011) Hepatitis C Virus NS2 Coordinates Virus Particle Assembly through Physical Interactions with the E1-E2 Glycoprotein and NS3-NS4A Enzyme Complexes. J Virol 85: 1706-1717.
Jirasko V, Montserret R, Lee J, Gouttenoire J, Moradpour D, et al. (2010) Structural and functional studies of nonstructural protein 2 of the hepatitis C virus reveal its key role as organizer of virion assembly. PLoS Pathog 6: e1001233-e1001233.
Masaki T, Suzuki R, Murakami K, Aizaki H, Ishii K, et al. (2008) Interaction of Hepatitis C Virus Nonstructural Protein 5A with Core Protein Is Critical for the Production of Infectious Virus Particles. J Virol 82: 7964-7976.
Tellinghuisen T, Foss K, Treadaway J (2008) Regulation of hepatitis C virion production via phosphorylation of the NS5A protein. PLoS Pathog 4: e1000032-e1000032.
Appel N, Zayas M, Miller S, Krijnse Locker J, Schaller T, et al. (2008) Essential role of domain III of nonstructural protein 5A for hepatitis C virus infectious particle assembly. PLoS Pathog 4: e1000035-e1000035.
Hughes M, Griffin S, Harris M (2009) Domain III of NS5A contributes to both RNA replication and assembly of hepatitis C virus particles. J Gen Virol 90: 1329-1334.
Counihan N, Rawlinson S, Lindenbach B (2012) Trafficking of hepatitis C virus core protein during virus particle assembly. PLoS Pathog 7: e1002302-e1002302.
Ohno H (2006) Clathrin-associated adaptor protein complexes. J Cell Science 119: 3719-3721.
Nakatsu F, Ohno H (2003) Adaptor protein complexes as the key regulators of protein sorting in the post-Golgi network. Cell Struct Funct 28: 419-429.
Owen D, Collins B, Evans P (2004) Adaptors for clathrin coats: structure and function. Annu Rev Cell Dev Biol 20: 153-191.
Traub LM, Bannykh SI, Rodel JE, Aridor M, Balch WE, et al. (1996) AP-2-containing clathrin coats assemble on mature lysosomes. J Cell Biol 135: 1801-1814.
Ricotta D, Conner SD, Schmid SL, von Figura K, Honing S (2002) Phosphorylation of the AP2 u subunit by AAK1 mediates high affinity binding to membrane protein sorting signals. J Cell Biol 156: 791-795.
Korolchuk VI, Banting G (2002) CK2 and GAK/auxilin2 Are Major Protein Kinases in Clathrin-Coated Vesicles. Traffic 3: 428-439.
Zhang CX, Engqvist-Goldstein A ° EY, Carreno S, Owen DJ, Smythe E, et al. (2005) Multiple Roles for Cyclin G-Associated Kinase in Clathrin-Mediated Sorting Events. Traffic 6: 1103-1113.
Duffer BA, Watkins SC, Montelaro RC (1998) Equine Infectious Anemia Virus Gag Polyprotein Late Domain Specifically Recruits Cellular AP-2 Adapter Protein Complexes during Virion Assembly. J Virol 72: 10218-10221.
Duffer BA, Parent LJ, Wills JW, Montelaro RC (1997) Equine infectious anemia virus utilizes a YXXL motif within the late assembly domain of the Gag p9 protein. J Virol 71: 6541-6546.
Chen C, Vincent O, Jin J, Weisz OA, Montelaro RC (2005) Functions of early (AP-2) and late AIP1/ALIX) endocytic proteins in equine infectious anemia virus budding. J Biol Chem 280: 40474-40480.
Noble B, Abada P, Nunez-Iglesias J, Cannon PM (2006) Recruitment of the Adaptor Protein 2 Complex by the Human Immunodeficiency Virus Type 2 Envelope Protein is Necessary for High Levels of Virus Release. J Virol 80: 2924-2932.
Batonick M, Favre M, Boge M, Spearman P, Hning 5, et al. (2005) Interaction of HIV-1 Gag with the clathrin-associated adaptor AP-2. Virology 342: 190-200.
Corless L, Crump CM, Griffin SDC, Harris M (2010) Vps4 and the ESCRTIII complex are required for the release of infectious hepatitis C virus particles. J Gen Virol 91: 362-372.

(56) References Cited

OTHER PUBLICATIONS

Ariumi Y, Kuroki M, Maki M, Ikeda M, Dansako H, et al. (2011) The ESCRT system is required for hepatitis C virus production. PLOS One 6: e14517-e14517.

Lai C-K, Jeng K-S, Machida K, Lai MMC (2010) Hepatitis C Virus Egress and Release Depend on Endosomal Trafficking of Core Protein. J Virol 84: 11590-11598.

Aguilar RC, Boehm M, Gorshkova I, Crouch RJ, Tomita K, et al. (2001) Signal-binding Specificity of the mu4 Subunit of the Adaptor Protein Complex AP-4. J Biol Chem 276: 13145-13152.

Cusick ME, Klitgord N, Vidal M, Hill DE (2005) Interactome: gateway into systems biology. Hum Mol Genet 14: Spec No. 2:R171-8.

Bailer SM, Haas J (2009) Connecting viral with cellular interactomes. Curr Opin Microbiol 12: 453-459.

Maerkl SJ, Quake SR (2007) A systems approach to measuring the binding energy landscapes of transcription factors. Science 315: 233-237.

Einav S, Gerber D, Bryson PD, Sklan EH, Elazar M, et al. (2008) Discovery of a hepatitis C target and its pharmacological inhibitors by microfluidic affinity analysis. Nat Biotechnol 26: 1019-1027.

Gerber D, Maerkl SJ, Quake SR (2009) An in vitro microfluidic approach to generating protein-interaction networks. Nat Methods 6: 71-74.

Cassonnet P, Rolloy C., Neveu G., Vidalain P.O., Chnatier T., et al. (2011) Benchmarking a luciferase complementation assay for detecting protein complexes. Nat Methods 8: 990-992.

Geminard C, De Gassart A, Blanc L, Vidal M (2004) Degradation of AP2 during reticulocyte maturation enhances binding of hsc70 and Alix to a common site on TFR for sorting into exosomes. Traffic 5: 181-193.

Lohmann V, Korner F, Koch J, Herian U, Theilmann L, et al. (1999) Replication of subgenomic hepatitis C virus RNAs in a hepatoma cell line. Science 285: 110-111.

Wang Y-H, Chang S, Huang C, Li Y-P, Lee C-H, et al. (2005) Novel nuclear export signal-interacting protein, NESI, critical for the assembly of hepatitis delta virus. J Virol 79: 8113-8120.

Ricotta D, Hansen J, Preiss C, Teichert D, HAning S (2008) Characterization of a Protein Phosphatase 2A Holoenzyme That Dephosphorylates the Clathrin Adaptors AP-1 and AP-2. J Biol Chem 283: 5510-5517.

Murray CL, Jones CT, Tassello J, Rice CM (2007) Alanine Scanning of the Hepatitis C Virus Core Protein Reveals Numerous Residues Essential for Production of Infectious Virus. J Virol 81: 10220-10231.

Kopp M, Murray CL, Jones CT, Rice CM (2010) Genetic Analysis of the Carboxy-Terminal Region of the Hepatitis C Virus Core Protein. J Viral 84: 1666-1673.

Ohno H, Aguilar RC, Yeh D, Taura D, Saito T, et al. (1998) The Medium Subunits of Adaptor Complexes Recognize Distinct but Overlapping Sets of Tyrosine-based Sorting Signals. J Biol Chem 273: 25915-25921.

Hitchcock IS, Chen MM, King JR, Kaushansky K (2008) YRRL motifs in the cytoplasmic domain of the thrombopoietin receptor regulate receptor internalization and degradation. Blood 112: 2222-2231.

Dunn KW, Kamocka MM, McDonald JH (2011) A practical guide to evaluating colocalization in biological microscopy. Am J of Physiol—Cell Physiol 300: C723-C742.

Karaman MW, Herrgard S, Treiber DK, Gallant P, Atteridge CE, et al. (2008) A quantitative analysis of kinase inhibitor selectivity. Nat Biotechnol 26: 127-132.

Hourioux C, Ait Goughoulte M, Patient R, Fouquenet D, Arcanger Doudet F, et al. (2007) Core protein domains involved in hepatitis C virus-like particle assembly and budding at the endoplasmic reticulum membrane. Cell microbial 9: 1014-1027.

Toh Q, Tan T, Teo W, Ho C, Parida S, et al. (2005) Identification of cellular membrane proteins interacting with hepatitis B surface antigen using yeast split-ubiquitin system. Int J Med Sci 2: 114-117.

Rost M, Mann S, Lambert C, Daring T, Thome N, et al. (2006) Gamma2-Adaptin, a Novel Ubiquitin-interacting Adaptor, and Nedd4 Ubiquitin Ligase Control Hepatitis B Virus Maturation. J Biol Chem 281: 29297-29308.

Hartmann-Stahler C, Prange R (2001) Hepatitis B Virus Large Envelope Protein Interacts with c2-Adaptin, a Clathrin Adaptor-Related Protein. J Virol 75: 5343-5351.

Freed EO (2002) Viral Late Domains. J Virol 76: 4679-4687.

Zhou H, Wang F, Wang Y, Ning Z, Hou W, et al. (2011) Improved Recovery and Identification of Membrane Proteins from Rat Hepatic Cells using a Centrifugal Proteomic Reactor. Mol Cell Proteomics 10: O111.008425.

Eden ER, White IJ, Tsapara A, Futter CE (2010). Membrane contacts between endosomes and ER provide sites for PTP1B-epidermal growth factor receptor interaction. Nat Cell Biol 12: 267-272.

Center for Drug Evaluation and Research Approval Package for : Application No. NDA 21-938 (GIST) and NDA 21-968 (MRCC); Jan. 17, 2006.

Milton et al., A Phase I/II Study of Weekly High-Dose Erlotinib in Previously Treated patients with Nonsmall Cell Lung Cancer; Cancer. Sep. 1, 2006;107(5):1034-41.

Groen et al. A randomized, double-blind, phase II study of erlotinib with or without sunitinib for the second-line treatment of metastatic non-small-cell lung cancer (NSCLC); Annals of Oncology 24: 2382-2389, 2013.

O'Farrell et al. An Innovative Phase I Clinical Study Demonstrates Inhibition of FLT3 Phosphorylation by SU11248 in Acute Myeloid Leukemia Patients; Clinical Cancer Research; vol. 9, 5465-5476, Nov. 15, 2003.

Bello et al. Electrocardiographic Characterization of the QTc Interval in Patients with Advanced Solid Tumors: Pharmacokinetic-Pharmacodynamic Evaluation of Sunitinib; Clin Cancer Res 2009;15(22) Nov. 15, 2009.

Ruinemans et al. Fatal necrotizing pancreatitis during combined treatment with erlotinib and sunitinib; Lung Cancer 70(2010) 364-365.

Houk et al. Relationship between exposure to sunitinib and efficacy and tolerability endpoints in patients with cancer: results of a pharmacokinetic/pharmacodynamic meta-analysis; Cancer Chemother Pharmacol; Dec. 2009.

Neveu et al. AAK1 and 1 GAK Regulate Hepatitis C Virus Entry and Are Potential Drug Targets; J. Virol; posted online Feb. 4, 2015.

Faivre et al. Safety, Pharmacokinetic, and Antitumor Activity of SU11248, a Novel Oral Multitarget Tyrosine Kinase Inhibitor, in Patients With Cancer; vol. 24; No. 1; Jan. 1, 2006; pp. 25-35.

Riely et al. Randomized Phase II Study of Pulse Erlotinib Before or After Carboplatin and Paclitaxel in Current or Dormer Smokers With Advanced Non-Small-Cell Lung Cancer; vol. 27; No. 2; Jan. 10, 2009; pp. 264-270.

Scagliotti et al. Sunitinib Plus Erlotinib Versus Placebo Plus Erlotinib in Patients With Previously Treated Advanced Non-Small-Cell Lung Cancer: A Phase III Trial; vol. 30; No. 17; Jun. 10, 2012; pp. 2070-2078.

Neveu et al. Identification and Targeting of an Interaction between a Tyrosine Motif within Hepatitis C Virus Core Protein and AP2M1 Essential for Viral Assembly; PLOS Pathogens; Aug. 2012; vol. 8; Issue 8; pp. 1-15.

Prados et al. Phase 1 study of erlotinib HCl alone and combined with temozolomide in patients with stable or recurrent malignant glioma. Neuro-Oncology 8, 67-78, 2006.

Grommes et al. "Pulsatile" high-dose weekly erlotinib for CNS metastases from EGFR mutant non-small cell lung cancer. Neuro-Oncology 13(12):1364-1369, 2011.

Blumenschein et al. Sunitinib Plus Erlotinib for the Treatment of Advanced/Metastatic Non-Small-Cell Lung Cancer; Journal of Thoracic Oncology—vol. 7, No. 9, Sep. 2012; pp. 1406-1416.

Liang TJ, Rehermann B, Seeff LB, Hoofnagle JH (2000) Pathogenesis, natural history, treatment, and prevention of hepatitis C. Ann Intern Med 132: 296-305.

Soriano V, Vispo E, Poveda E, Labarga P, Martin Carbonero L, et al. (2011) Directly acting antivirals against hepatitis C virus. J Antimicrob Chemother 66: 1673-1686.

(56) References Cited

OTHER PUBLICATIONS

Bartenschlager R, Lohmann V (2000) Replication of hepatitis C virus. J Gen Virol 81 Pt 7: 1631-1648.
Branch AD (2000) Hepatitis C virus Rna codes for proteins and replicates: does it also trigger the interferon response? Semin Liver Dis 20: 57-68.
Reed KE, Rice CM (2000) Overview of hepatitis C virus genome structure, polyprotein processing, and protein properties. Curr Top Microbiol Immunol 242: 55-84.
Lindenbach BD, Evans MJ, Syder AJ, Wolk B, Tellinghuisen TL, et al. (2005) Complete replication of hepatitis C virus in cell culture. Science 309: 623-626.
Roingeard P, Hourioux C, Blanchard E, Brand D, Ait Goughoulte M (2004) Hepatitis C virus ultrastructure and morphogenesis. Biol Cell 96: 103-108.
Rouille Y, Helle F, Delgrange D, Roingeard P, Voisset C, et al. (2006) Subcellular Localization of Hepatitis C Virus Structural Proteins in a Cell Culture System That Efficiently Replicates the Virus. J Virol 80: 2832-2841.
Boson B, Granio O, Bartenschlager R, Cosset F-L (2011) A concerted action of hepatitis C virus p7 and nonstructural protein 2 regulates core localization at the endoplasmic reticulum and virus assembly. PLoS Pathog 7: e1002144-e1002144.
Miyanari Y, Atsuzawa K, Usuda N, Watashi K, Hishiki T, et al. (2007) The lipid droplet is an important organelle for hepatitis C virus production. Nat Cell Biol 9: 1089-1097.
Boulant S, Targett-Adams P, McLauchlan J (2007) Disrupting the association of hepatitis C virus core protein with lipid droplets correlates with a loss in production of infectious virus. J Gen Virol 88: 2204-2213.
Fukasawa M (2010). Cellular lipid droplets and hepatitis C virus life cycle. Biol Pharm Bull 33: 355-359.
Shi S, Polyak S, Tu H, Taylor D, Gretch D, et al. (2002) Hepatitis C virus NS5A colocalizes with the core protein on lipid droplets and interacts with apolipoproteins. Virology 292: 198-210.
Barba G, Harper F, Harada T, Kohara M, Goulinet S, et al. (1997) Hepatitis C virus core protein shows a cytoplasmic localization and associates to cellular lipid storage droplets. Proc Natl Acad Sci U S A 94: 1200-1205.
Moradpour D, Englert C, Wakita T, Wands JR (1996) Characterization of cell lines allowing tightly regulated expression of hepatitis C virus core protein. Virology 222: 51-63.
Mackenzie JM, Westaway EG (2001) Assembly and maturation of the flavivirus Kunjin virus appear to occur in the rough endoplasmic reticulum and along the secretory pathway, respectively. J Virol 75: 10787-10799.
Mukhopadhyay S, Kuhn R, Rossmann M (2005) A structural perspective of the flavivirus life cycle. Nat Rev Microbiol 3: 13-22.
Roingeard P, Hourioux C, Blanchard E, Prensier G (2008) Hepatitis C virus budding at lipid droplet-associated ER membrane visualized by 3D electron microscopy. Histochem Cell Biol 130: 561-566.
Jones D, McLauchlan J (2010) Hepatitis C virus: assembly and release of virus particles. J Biol Chem 285: 22733-9.
Cocquerel L, Duvet S, Meunier JC, Pillez A, Cacan R, et al. (1999) The transmembrane domain of hepatitis C virus glycoprotein E1 is a signal for static retention in the endoplasmic reticulum. J Virol 73: 2641-2649.
Coller K, Heaton N, Berger K, Cooper J, Saunders J, et al. (2012) Molecular determinants and dynamics of hepatitis C virus secretion. PLoS Pathog 8: e1002466-e1002466.
Gastaminza P, Cheng G, Wieland S, Zhong J, Liao W, et al. (2008) Cellular Determinants of Hepatitis C Virus Assembly, Maturation, Degradation, and Secretion. J Virol 82: 2120-2129.
Huang H, Sun F, Owen D, Li W, Chen Y, et al. (2007) Hepatitis C virus production by human hepatocytes dependent on assembly and secretion of very low-density lipoproteins. Proc Natl Acad Sci U S A 104: 5848-5853.
Chang K-S, Jiang J, Cai Z, Luo G (2007) Human Apolipoprotein E Is Required for Infectivity and Production of Hepatitis C Virus in Cell Culture. J Virol 81: 13783-13793.
Jiang J, Luo G (2009) Apolipoprotein E but not B is required for the formation of infectious hepatitis C virus particles. J Virol 83: 12680-12691.
Merz A, Long G, Hiet M-S, Brugger B, Chlanda P, et al. (2011) Biochemical and Morphological Properties of Hepatitis C Virus Particles and Determination of Their Lipidome. J Biol Chem 286: 3018-3032.
Bartenschlager R, Penin F, Lohmann V, Andre P (2011) Assembly of infectious hepatitis C virus particles. Trends Microbiol 19: 95-103.
McLauchlan (2000) Properties of the hepatitis C virus core protein: a structural protein that modulates cellular processes. J Viral Hepat 7: 2-14.
McLauchlan J, Lemberg M, Hope G, Martoglio B (2002) Intramembrane proteolysis promotes trafficking of hepatitis C virus core protein to lipid droplets. EMBO J 21: 3980-3988.
Boulant S, Montserret R, Hope RG, Ratinier M, Targett-Adams P, et al. (2006) Structural Determinants That Target the Hepatitis C Virus Core Protein to Lipid Droplets. J Biol Chem 281: 22236-22247.
Boulant S, Vanbelle C, Ebel C, Penin Fo, Lavergne J-P (2005) Hepatitis C Virus Core Protein Is a Dimeric Alpha-Helical Protein Exhibiting Membrane Protein Features. J Virol 79: 11353-11365.
Herker E, Harris C, Hernandez C, Carpentier A, Kaehlcke K, et al. (2010) Efficient hepatitis C virus particle formation requires diacylglycerol acyltransferase-1. Nat Med 16: 1295-1298.
Parent R, Qu X, Petit M-A, Beretta L (2009) the heat shock cognate protein 10 is associated with hepatitis C virus particles and modulates virus infectivity. Hepatology 49: 1798-1809.
Backes P, Quinkert D, Reiss S, Binder M, Zayas M, et al. (2010) Role of Annexin A2 in the Production of Infectious Hepatitis C Virus Particles. J Virol 84: 5775-5789.
Tamai K, Shiina M, Tanaka N, Nakano T, Yamamoto A, et al. (2012) Regulation of hepatitis C virus secretion by the Hrs-dependent exosomal pathway. Virology 422: 377-385.
Abid et al. Journal of Hepatology; 2003 vol. 38, Supplement 2, p. 3.
Dhanak et al. J Biol Chem. Oct. 11, 2002;277(41):38322-7. Epub Aug. 6, 2002.
Zhong et al. Antimicrob Agents Chemother. Aug. 2003;47(8):2674-81.
Osborn et al. J Pharmacol Exp Ther. Nov. 2002;303(2):540-8.
Masci et al. Curr Oncol Rep. Mar. 2003;5(2):108-13.
Schweitzer, BK et al. Overview of the Flaviviridae With an Emphasis on the Japanese Encephalitis Group Viruses. Lab Medicine, 2009: 40: 493-499.
Jha et al. Journal of Biol. Chem. 2011. vol. 286. No. 30, pp. 26319-26326.
Bekerman et al., "Anticancer kinase inhibitors impair intracellular viral trafficking and exert broad-spectrum antiviral effects", The Journal of Clinical Investigation, 2017, 127(4): 1338-1352, doi: 10.1172/JCI89857.
Potisopon et al., "Comparison of dengue virus and HCV: from impact on global health to their RNA-dependent RNA polymerases", Future Virology, 2014, 9(1): 53-67.

* cited by examiner

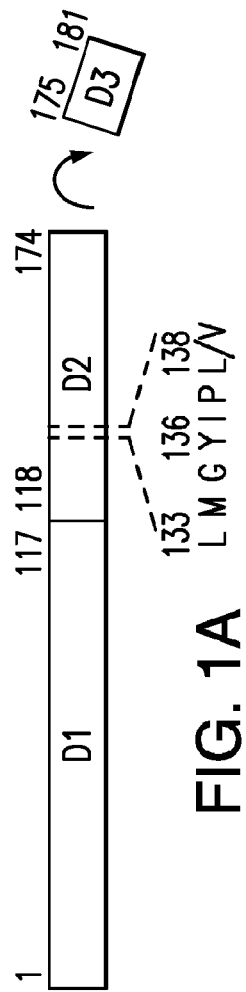

FIG. 1A

| Host protein | Motif | | | | | | Partner |
|---|---|---|---|---|---|---|---|
| Consensus | Ƶ/X | X₁ | X₂ | Y | X₃ | X₄ | Ƶ |
| TFR | | P | L | S | Y | T | R | F | AP2M1 |
| P-selctin | | L | G | T | Y | G | V | F | AP2M1 |
| HLA-DM | | H | S | S | Y | T | P | L | AP2M1 |

FIG. 1B

| Virus/Protein | Motif | | | | | Host partner(s) |
|---|---|---|---|---|---|---|
| Consensus | Y | X | X | Ƶ | | |
| ELAV/Gag | Y | P | D | L | | AP2M1 |
| HIV-1/Gag | Y | P | I | V | | AP2M1 |
| HIV-1/Env | Y | S | P | L | | AP2M1, AP1M1, AP3M1 |

FIG. 1C

| HCV/Core | Motif | | | | | | | |
|---|---|---|---|---|---|---|---|---|
| Consensus | φ | X1 | X2 | Y | X3 | X4 | Ƶ | |
| HCV consensus | L | M | G | Y | I | P | L/V | |
| % conservation | 99.3 | 98.9 | 99.4 | 98.9 | 98 | 99.6 | 86.71 | |
| Genotypes 1,3,4,5 | L | M | G | Y | I | P | L | |
| Genotypes 2,6,7,8 | L | M | G | Y | I | P | V | |
| Y136A mutant | L | M | G | A | I | P | V | |
| φ139A mutant | L | M | G | Y | A | P | L | |
| φ139L mutant | L | M | G | Y | I | P | L | |
| YTPL mutant | L | M | G | Y | T | P | L | |
| YRRL mutant | L | M | G | Y | R | R | L | |

FIG. 1D

| Mutant | TCID$_{50}$/ml | |
|---|---|---|
| | Extracellular | Intracellular |
| J6/JFH(p7-Rluc2A)........................ | 6.32x10$^3$ | 3.15x10$^4$ |
| J6/JFH(p7-Rluc2A)/ΔE1-E2......... | 0 | 0 |
| J6/JFH(p7-Rluc2A)/Y136A............ | 0 | 0 |
| J6/JFH(p7-Rluc2A)/V139A............ | 1.19x10$^2$ | 4.5x10$^3$ |

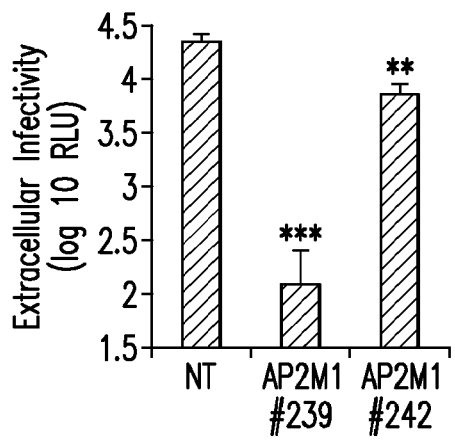
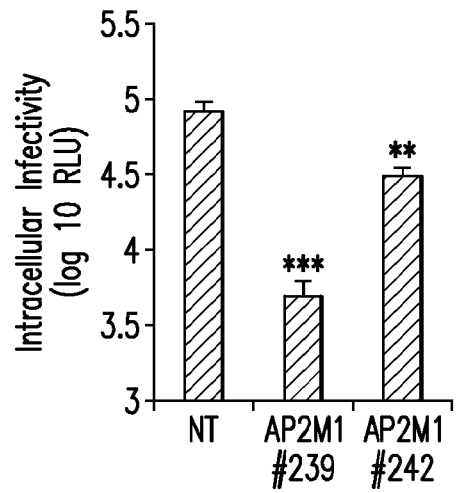
FIG. 4D  FIG. 4E
| Clone | TCID$_{50}$/ml | |
|---|---|---|
| | Extracellular | Intracellular |
| NT.................................. | 6.32x10$^3$ | 2.14x10$^4$ |
| AP2M1 #239.................. | 1.58x10$^1$ | 7.01x10$^1$ |
| AP2M1 #242.................. | 1.79x10$^2$ | 2.05x10$^3$ |
FIG. 4F

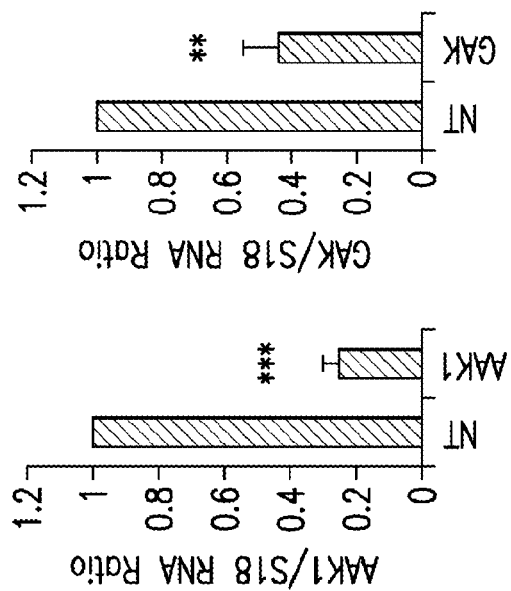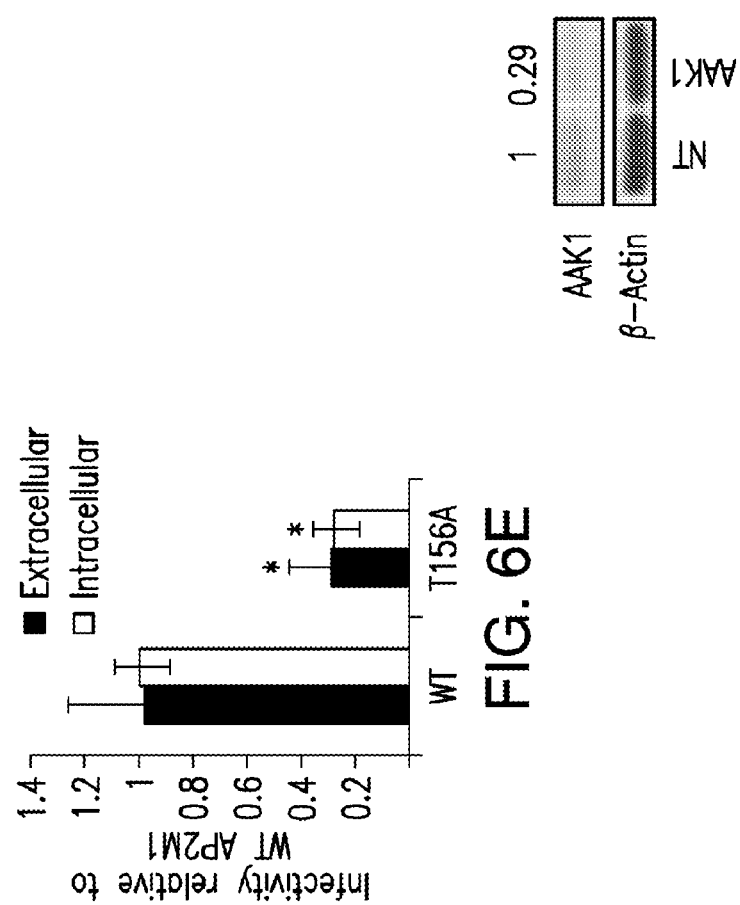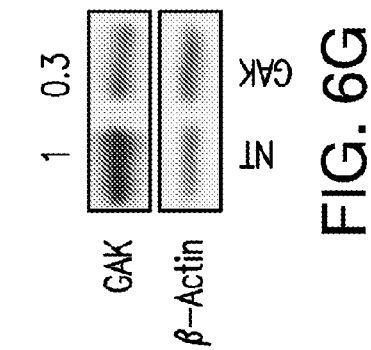

| Compound | Target | Kd of binding (nM) | IC50 (μM) | EC50 for Extracellular Infectinity (μM) | EC50 for Intracellular Infectivity (μM) | EC50 for HCVcc infection (μM) |
|---|---|---|---|---|---|---|
| Erlotinib | GAK | 3.1 | 0.038±0.01 | 0.6±0.12 | 0.45±0.13 | 0.6±0.12 |
| Sunitinib malate | AAK1 | 11 | 0.045±0.02 | 0.2±0.03 | 0.155±0.06 | 1.2±0.3 |
| PKC-412 | AAK1 | 48 | 0.2±0.07 | 1.6±0.4 | 1.79±0.4 | 4.6±2 |

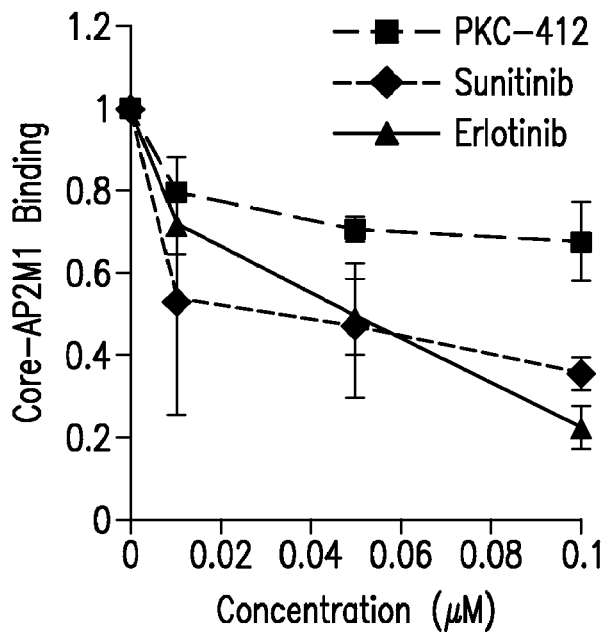
FIG. 7C
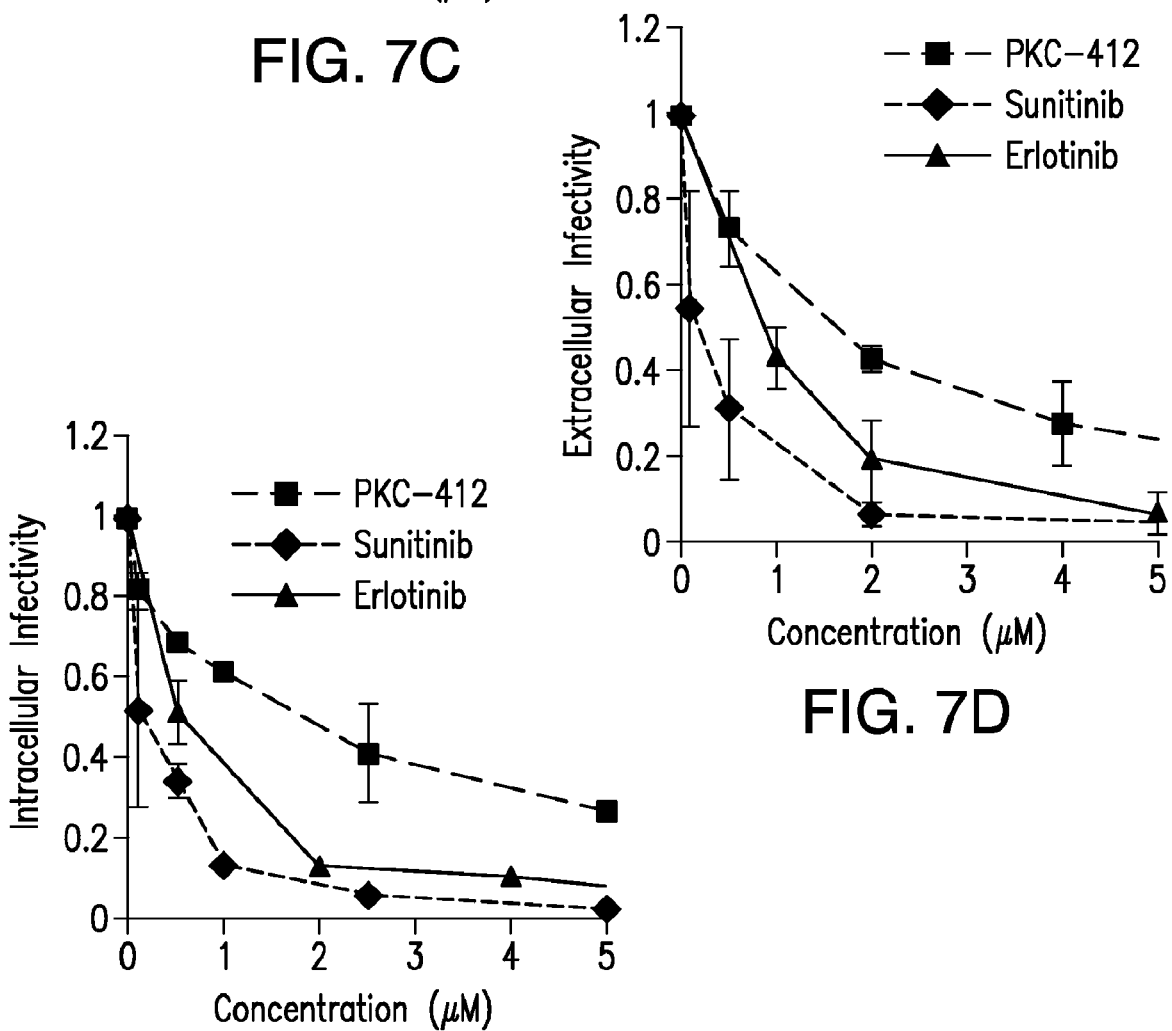
FIG. 7D
FIG. 7E

METHODS AND COMPOSITIONS FOR TREATING VIRAL DISEASES

CROSS REFERENCE TO RELATED APPLICATIONS

This application is a Divisional of U.S. application Ser. No. 14/362,993, filed Jun. 5, 2014, which is a U.S. National filing of and claims priority to PCT/US2012/068167, filed Dec. 6, 2012, which claims priority to U.S. Provisional Patent Application No. 61/567,491, filed Dec. 6, 2011. Priority to each of the above referenced applications is claimed and the content of each application is incorporated herein by reference in their entirety.

STATEMENT REGARDING FEDERALLY SPONSORED RESEARCH

This invention was made with Government support under contract AI079406 awarded by the National Institutes of Health. The Government has certain rights in this invention.

FIELD OF THE INVENTION

The present invention relates to virology. More specifically, the invention relates to treatment of viral diseases through inhibition of interactions of host cellular clathrin adaptor proteins and viral YXXΦ or dileucine motifs or their regulation.

BACKGROUND OF THE INVENTION

Human infections with Lentiviridae, such as HIV, and Flaviviridae, such as HCV, pose significant challenges to global health. Although potent anti-HCV drugs are in clinical development and response rates to interferon-based regimens have improved with the inclusion of protease inhibitors (PI), resistance, drug-drug interactions, and cumulative toxicity continue to pose challenges. More effective antiviral strategies are therefore still in need to combat the HCV pandemics. In addition, novel antiviral strategies are needed for inclusion in salvage regimens for treating HIV in patients failing highly active antiretroviral therapy (HAART) due to resistant virus.

SUMMARY OF THE INVENTION

Briefly described, embodiments of this disclosure include compounds, compositions, pharmaceutical compositions, and methods of treating a host with a viral infection. In an embodiment, susceptible viruses according to the present disclosure include viruses comprising at least one protein comprising a YXXΦ motif or a dileucine motif, referred to herein as "clathrin AP binding viruses," Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, methods of treating replication of such virus in a host, methods of inhibiting the binding of a viral structural protein comprising the YXXΦ or dileucine motifs to host μ subunits of clathrin AP1-AP4 complexes, such as AP2M1, AP1M1, AP3M1, or AP4M1, methods of treating viral hepatitis-related liver fibrosis in a host, and the like.

One exemplary method of treating a host with a viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, among others, may include: administering to the host a therapeutically effective amount of an inhibiting agent to reduce the viral load in the host. In an embodiment, the inhibiting agent is selected from the group consisting of agents that competitively inhibit binding between a viral protein comprising the YXXΦ or dileucine motifs and a host protein selected from the group consisting of the μ subunits of clathrin AP1-AP4; and agents that inhibit host protein kinase activity of kinases that modulate the activity of host proteins selected from the group consisting of μ subunits of clathrin AP1-AP4. One exemplary method of treating viral infection of clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, in a host, among others, may include: administering an inhibiting agent to the host having such viral infection or infections. In an embodiment, the inhibiting agent is selected from the group consisting of agents that competitively inhibit binding between a viral structural protein comprising the YXXΦ or dileucine motifs and a host protein selected from the group consisting of AP2M1, and agents that inhibit host protein kinase activity of kinases that modulate the activity of host proteins selected from the group consisting of AP2M1 and other μ subunits of clathrin AP complexes. In some embodiments, these inhibitors inhibit GAK (cyclin G-associated kinase) or AAK1 (adaptor-associated kinase 1), which include compounds such as erlotinib, sunitinib, or PKC-412. Thus, inhibitory agents are of two classes: (1) competitive inhibitors of binding; and (2) agents that inhibit host protein kinase activity of kinases that modulate the activity of host proteins such as AP2M1 and/or other μ subunits of clathrin AP complexes.

One exemplary method of inhibiting the binding of the YXXΦ or dileucine motifs to host polypeptides, among others, includes administering an inhibiting agent to the host having a viral infection. In an embodiment, the inhibiting agent is selected from the group consisting of agents that competitively inhibit binding between a viral structural protein comprising the YXXΦ or dileucine motifs and a host protein selected from AP2M1 or other μ subunits of clathrin AP complexes, and agents that inhibit protein kinase activity of kinases that modulate the activity of host proteins selected from the group consisting of AP2M1 and/or other μ subunits of clathrin AP complexes.

One exemplary pharmaceutical composition for treating a host having a viral infection of clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, among others, may include an inhibiting agent. In an embodiment, the inhibiting agent is selected from the group consisting of agents that competitively inhibit binding between a viral structural protein comprising the YXXΦ or dileucine motifs and a host protein selected from AP2M1 and/or other μ subunits of clathrin AP complexes, and agents that inhibit protein kinase activity of kinases that modulate the activity of host proteins secreted from the group consisting of AP2M1 and/or other μ subunits of clathrin AP complexes.

One exemplary composition, among others, includes an inhibiting agent. In an embodiment, the inhibiting agent is selected from the group consisting of agents that competitively inhibit binding between a viral protein comprising the YXXΦ or dileucine motif and a host protein selected from the group consisting of AP2M1 and/or other μ subunits of clathrin AP complexes, and agents that inhibit protein kinase activity of kinases that modulate the activity of host proteins selected from the group consisting of AP2M1 and/or other μ subunits of clathrin AP complexes.

In one aspect, the present invention provides a method of treating HCV-HIV co-infection through administration of an effective amount of an agent that inhibits binding of HCV and HIV to host proteins selected from the group consisting of AP2M1 and other μ subunits of clathrin AP complexes. In one embodiment, the inhibiting agent inhibits AAK1 or GAK. In another embodiment, the agent is selected from the group consisting of erlotinib, sunitinib, and PKC-412. In another embodiment, the agent prevents binding of a Lentiviridae or Flaviviridae structural protein containing a YXXΦ or dileucine motif to a host protein selected from the group consisting of AP2M1 and/or other μ subunits of clathrin AP complexes. In still another embodiment, the agent inhibits AAK.

In another aspect, the invention provides a method of inhibiting infections by at least a first virus other than HCV, another member of Flaviviridae, or a member of Lentiviridae, or combinations thereof, through administration to a patient in need an effective amount of an agent that inhibits binding of a structural protein from a virus containing a YXXΦ or dileucine motif to a host protein selected from the group consisting of AP2M1 and/or other μ subunits of clathrin AP complexes. In one embodiment, the agent inhibits AAK1 or GAK. In another embodiment, the agent is selected from the group consisting of erlotinib, sunitinib, and PKC-412.

In another aspect, the present invention provides a method of screening for antiviral agents through contacting a susceptible virus as described herein or viral protein with a candidate agent and a protein selected from the group consisting of AP2M1 and/or other μ subunits of clathrin AP complexes, and determining an effect of the candidate agent on the binding of virus to the host protein.

In another aspect, the present invention provides a method of screening for antiviral agents through contacting a susceptible virus as described herein with a candidate agent and a cell expressing a protein selected from the group consisting of AP2M1 and other μ subunits of clathrin AP complexes, and determining the effect of the candidate agent on viral assembly or budding. In one embodiment, the candidate agent inhibits the activity of AAK1 or GAK.

In another aspect, the present invention provides a method of inhibiting assembly or budding of clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, in a host cell through contacting the host cell with an agent that prevents binding of a viral structural protein containing a YXXΦ or dileucine motif to a host protein selected from the group consisting of AP2M1 and other μ subunits of clathrin AP complexes. In one embodiment, the agent blocks binding of the viral structural protein to the host protein. In another embodiment, the agent competes with the viral structural protein for binding to the host protein. In another embodiment, the agent competes with the host protein for binding to the viral structural protein. In still another embodiment, the method involves screening of AAK1 and GAK inhibitors for non-Flaviviridae viruses.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 1A-F: Shows a viral core with a YXXΦ motif that binds AP2M1. FIG. 1(A) Schematics of core. The location of the identified motif is indicated. FIG. 1(B)-(C) Consensus sequences of YXXΦ motifs from representative human (B) and viral (C) proteins. FIG. 1(D) The consensus sequence of all HCV isolates, clones used in this study, and engineered core mutants. FIG. 1(E) Fluorescent images from a microfluidic chip and schematics. Left: AP2M1-V5-his was anchored to the device surface via its interaction with anti-His antibodies and labeled with anti-V5-FITC antibodies. Middle: T7-tagged core or NS3 were incubated with surface bound AP2M1 and labeled with anti-T7-Cy3 antibodies. Interactions were trapped mechanically by MITOMI. Cy3 signal representing bound viral protein is shown following a wash. Right: an overlay of the Cy3 and FITC signals, representing bound viral prey to human bait ratio. FIG. 1F. In vitro binding curves of core-T7 and NS3-T7 to surface bound AP2M1. Y axis represents bound viral protein to surface bound AP2M1 ratio.

FIG. 2(A) Schematics of the PCAs format. A and B represent prey and bait proteins, and GLuc1/2 are fragments of *Gaussia* luciferase. FIG. 2(B) Cells were cotransfected with combinations of plasmids indicated below the graph with those indicated in the legend. Y axis represents luminescence relative to the core-AP2M1 signal. The banded bar on the right represents AP2M1 binding to the host cargo protein TFR. FIG. 2(C) Core-AP2M1 binding in the presence of free AP2M1, core or NESI. Y axis represents luminescence ratio (the average luminescence signal detected in cells transfected with Gluc1-AP2M1 and Gluc2-core divided by the average of luminescence measured in control wells transfected with Gluc1-AP2M1 and an empty Gluc2 vector with those transfected with Gluc2-core and an empty Gluc1 vector relative to core-AP2M1 binding in the presence of empty PUC19. FIG. 2(D) Immunoprecipitations (IPs) in membranes of HCV infected cells. Left panels: Anti-AP2M1 antibodies or IgG were used for IP. Membranes were immunoblotted with anti-phospho-AP2M1, anti-AP2M1, anti-core, and anti-actin antibodies. Cal-A represents calyculin-A. Right panels: Anti-core antibodies or IgG were used for IP. Membranes were immunoblotted with anti-core, anti-AP2M1, and anti-actin antibodies. FIG. 2(E) Representative confocal IF microscopy images of AP2M1 and core in Huh-7.5 cells 3 days postelectroporation with J6/JFH HCV RNA. Data represent means±s.d. (error bars) from three independent experiments in triplicates (n>20 in E). *p<0.05, p<0.01, *p<0.001.

FIG. 3(A) Binding of wild type (WT) and core mutants to AP2M1 by PCAs. Y axis represents luminescence ratio (the average luminescence signal detected in cells transfected with Gluc1-AP2M1 and the various forms of Gluc2-core divided by the average of luminescence measured in control wells transfected with Gluc1-AP2M1 and an empty Gluc2 vector with those transfected with the respective Gluc2-core and an empty Gluc1 vector) relative to WT core-AP2M1 binding. FIG. 3(B) HCV RNA replication by *Renilla* luciferase assays at 6 hr (white) and 72 hr (black) postelectroporation with J6/JFH (p7-Rluc2A) harboring the corresponding mutations. ΔE1-

E2 is an assembly defective control. GNN is a replication defective polymerase mutant. FIG. 3(C) Extracellular infectivity by luciferase assays in naive Huh-7.5 cells infected with supernatants derived from the electroporated cells. FIG. 3(D) Intracellular infectivity by luciferase assays in naive Huh-7.5 cells infected with clarified cell lysates derived from the electroporated cells. FIG. 3(E) Intra- and extracellular infectivity titers measured by limiting dilution assays. $TCID_{50}$ is a 50% tissue culture infectious dose. FIG. 3(F) Viral RNA release into the culture supernatant at 72 hr postelectroporation measured by qRT-PCR. FIG. 3(G) HCV core protein release into the culture supernatant at 72 hr postelectroporation determined by ELISA relative to WT control. FIG. 3(H) Levels of core protein by western analysis in lysates prepared from cells infected with virus harboring the corresponding mutations. Means and s.d. (error bars) of results from at least three independent experiments in triplicates are shown. The dashed horizontal lines represent background levels of luciferase activity. RLU is relative light units. *$p<0.05$, $p<0.01$, *$p<0.001$.

FIG. 4A-I: Shows inhibition of HCV assembly by AP2M1 depletion. FIG. 4(A) AP2M1 protein levels by quantitative western analysis in stable clones harboring shRNA lentiviral constructs targeting the AP2M1 gene and a non-targeting (NT) sequence. A representative membrane and combined data from three independent measurements are shown. Y axis represents AP2M1 to actin protein ratio relative to NT control. FIG. 4(B) AP2M1/S18 RNA ratio by qRT-PCR in selected stable clones relative to NT control. FIG. 4(C) The indicated clones were electroporated with J6/JFH(p7-Rluc2A). HCV RNA replication in these clones by luciferase assays at 9 hr (white) and 72 hr (black) postelectroporation. FIG. 4(D) Extracellular infectivity measured by luciferase assays in naive cells inoculated with supernatants derived from the various stable cell clones. FIG. 4(E) Intracellular infectivity by luciferase assays in naive Huh-7.5 cells infected with clarified cell lysates derived from the electroporated cells. FIG. 4(F) Intra- and extracellular infectivity titers measured by limiting dilution assays. $TCID_{50}$ is a 50% tissue culture infectious dose. FIG. 4(G) Viral RNA release into the culture supernatant at 72 hr postelectroporation measured by qRT-PCR. FIG. 4(H) HCV core protein release into the culture supernatant at 72 hr postelectroporation, as determined by ELISA. FIG. 4 (I) Infectious virus production relative to NT control (top panel) and levels of AP2M1 protein by a western blot analysis (bottom panel) in cells concurrently transduced with lentiviruses expressing shAP2M1 and shRNA resistant WT AP2M1 cDNA (AP2M1-WT). Means and s.d. (error bars) of results from at least three independent experiments are shown. RLU is relative light units. *$p<0.05$, $p<0.01$, *$p<0.001$.

FIG. 5(A) A representative merged image of endogenous AP2M1 (blue) and the LD marker, Bodipy (green), in naive Huh-7.5 cells. FIG. 5(I) is demonstrated in the respective bottom panels. FIG. 5(K)-(P) Representative merged images and quantitative colocalization analysis of core (red) and (K) Bodipy (green), demonstrating increased localization of core to LD in Huh-7.5 cells electroporated with J6/JFH HCV RNA harboring the Y136A core mutation (right panel) compared with WT core (left panel). FIG. 5(L) Bodipy (green) in control (NT) cells (left panel) or AP2M1 depleted (right panel) Huh-7.5 electroporated with J6/JFH HCV RNA, showing a dramatic localization of core to LD in AP2M1 depleted cells. FIG. 5(M). TGN46 (green), demonstrating decreased localization of core to TGN in Huh-7.5 cells electroporated with J6/JFH RNA harboring the Y136A core mutation (right panel) compared with WT core (left panel). FIG. 5(N) TGN46 (green) in control (NT) cells (left panel) or AP2M1 depleted (right panel) Huh-7.5 electroporated with J6/JFH HCV RNA, showing decreased localization of core to TGN in AP2M1 depleted cells. FIG. 5(O) E2 (green), demonstrating decreased colocalization of core and E2 in Huh-7.5 cells electroporated with J6/JFH RNA harboring the Y136A core mutation (right panel) compared with WT core (left panel). FIG. 5(P) E2 (green) in control (NT) cells (left panel) or AP2M1 depleted (right panel) Huh-7.5 electroporated with J6/JFH HCV RNA, showing decreased colocalization of core and E2 in AP2M1 depleted cells. Representative images at ×60 magnification are shown. Graphs represent quantitative colocalization analysis of Z stacks using Manders' coefficients. Values indicate mean M2 values represented as percent colocalization (the fraction of green intensity that coincides with red intensity or in the case of FIGS. FIG. 5(G)-(I), the fraction of blue intensity that coincides with red intensity)±s.d. (error bars); n=10-15. *$p<0.05$, $p<0.01$, *$p<0.001$.

FIG. 6A-L: Shows that AAK1 and GAK regulate core-AP2M1 binding and are involved in HCV assembly. FIG. 6(A) Regulatory mechanisms of AP2M1 binding to host cargo proteins harboring YXXΦ signals. FIG. 6(B) Binding of core to wild type and T156A AP2M1 mutant by PCAs (black) and microfluidics (white). FIG. 6(C)-(E) Huh-7.5 were transfected with plasmids encoding WT or T156A AP2M1 mutant and electroporated with J6/JFH(p7-Rluc2A) 48 hr posttransfection. FIG. 6(C) Cellular viability by alamarBlue-based assays at 48 hr posttransfection relative to WT AP2M1 control. FIG. 6(D) HCV RNA replication in cells overexpressing WT or T156A AP2M1 mutant by luciferase assays at 6 hr (black) and 72 hr (white) postelectroporation with J6/JFH(p7-Rluc2A). FIG. 6(E) Extracellular (black) and intracellular (white) infectivity by luciferase assays in naive Huh-7.5 cells infected with supernatants or cell lysates derived from the indicated cells, respectively, relative to WT control. FIG. 6(F)-(G) Huh7.5 cells were transfected with the corresponding siRNAs. FIG. 6(F) Ratio of AAK1 (left) or GAK (right) to S18 RNA in these cells relative to NT sequences by qRT-PCR. FIG. 6(G) Quantitative western analysis. Numbers represent AAK1 (top) or GAK (bottom) to actin protein ratios relative to NT control. FIG. 6(H) Core-AP2M1 binding by PCAs in Huh-7.5 cells depleted for AAK1 or GAK by siRNAs. Y axis represents luminescence ratio (the average luminescence signal detected in cells transfected with Gluc1-AP2M1 and Gluc2-core divided by the average of luminescence measured in NT cells transfected with Gluc1-AP2M1 and an empty Gluc2 vector with those transfected with Gluc2-core and an empty Gluc1 vector) relative to NT control. FIG. 6(I)-(K) AAK1 or GAK depleted cells were electroporated with J6/JFH(p7-Rluc2A). FIG. 6(I) Cellular viability by alamar-Blue-based assays in depleted cells relative to NT control. FIG. 6(J) HCV RNA replication in these cells by luciferase assays at 6 hr (black) and 72 hr (white) postelectroporation. FIG. 6(K) Extracellular (black) and intracellular (white) infectivity by luciferase assays in naive Huh-7.5 cells infected with supernatants or cell lysates derived from the indicated cells, respectively, relative to NT control. FIG. 6(L) Core binding to AAK1 and GAK by PCAs. Y axis represents luminescence ratio relative to core-AP2M1 binding. Data represent means and s.d. (error bars) from at least two experiments in triplicates. RLU is relative light units. $*p<0.05$, $p<0.01$, $*p<0.001$.

FIG. 7A-I: Pharmacological inhibition of core-AP2M1 binding and HCV assembly. FIG. 7(A) AP2M1 regulators and the discovered inhibitors. FIG. 7(B) The inhibitors' Kds of binding to AAK1 or GAK (Karaman et al., Nat Biotechnol 26:127-132, 2008). IC50s for these compounds effect on core-AP2M1 binding, and EC50s for their effect on extracellular infectivity, intracellular infectivity, and viral infection with cell culture grown HCV (HCVcc). FIG. 7(C) Inhibition of core-AP2M1 binding by the compounds measured by PCAs. FIG. 7(D)-(G) Huh-7.5 cells electroporated with J6/JFH(p7-Rluc2A) were treated daily with either erlotinib, sunitinib or PKC-412 for 3 days. Supernatants and cell lysates were harvested at 72 hr and used to inoculate naive Huh-7.5 cells. Dose response curves of the inhibitors' effects on extracellular (D) and intracellular (E) infectivity relative to untreated controls. These compounds had no effect on HCV RNA replication (F) or cellular viability (G) by luciferase and AlamarBlue-based assays, respectively (GNN is a replication-defective polymerase mutant). FIG. 7(H) The effect of the inhibitors on AP2M1 phosphorylation by western analysis of cell lysates harvested following electroporation with J6/JFH(p7-Rluc2A) and treatment with the compounds in the presence of Calyculin A (Cal-A). Representative membranes blotted with anti-phopho-AP2M1 (p-AP2M1) and anti-actin antibodies, and quantitative analysis from 3 experiments are shown. Y axis represents pAP2M1/actin protein ratio relative to untreated controls. FIG. 7(I) The inhibitors' effect on viral infection (black) and cellular viability (grey) in cells infected with HCVcc following 72 hr of daily treatment relative to untreated controls. Data represent means and s.d. (error bars) from at least three experiments in triplicates. RLU is relative light units. $*p<0.05$, $p<0.01$, $*p<0.001$.

FIG. 8(A) AP2M1/S18 RNA ratio measured by qRT-PCR in Huh-7.5 cells transfected with a pool of four siRNAs (ON-TARGETplus SMARTpools, Dharmacon) targeting AP2M1 or a pool of non-targeting (NT) sequences at 48 hr posttransfection relative to NT contols. FIG. 8(B) AP2M1 protein levels by quantitative western analysis in cells 48 hr posttransfection with the corresponding pooled siRNAs. Numbers represent AP2M1 to actin protein ratio relative to the NT control. FIG. 8(C) Cellular viability by alamarBlue assays 48 hr post siRNAs transfections relative to NT control. FIG. 8(D) Cells were electroporated with J6/JFH(p7-Rluc2A) at 48 hr following transfection with the indicated pooled siRNAs. HCV RNA replication in these cells by luciferase assays at 6 hr (black) and 72 hr (white) postelectroporation. FIG. 8(E) Extracellular (black) and intracellular (white) infectivity measured in naive Huh-7.5 cells infected with supernatants or clarified cell lysates derived from electroporated cells harboring the indicated siRNAs by luciferase assays, respectively. FIG. 8(F) Infectious virus production measured by limiting dilution assays. FIG. 8(G) Extracellular (black) and intracellular (white) infectivity measured by focus formation assays in naive Huh-7.5 cells infected with supernatants or clarified cell lysates derived from Huh-7.5 cells transiently depleted for AP2M1 by siRNAs and infected with culture grown J6/JFH virus (titer: $1.2 \times 10^5$ TCID$_{50}$/ml). Results are relative to NT controls. Means±s.d. (error bars) of results from at least two independent experiments are shown. RLU is relative light units. TCID$_{50}$ is 50% tissue culture infectious dose.

FIG. 9(A) HIV replication in AAK1 or GAK depleted cells relative to NT control. FIG. 9 (B) The antiviral effect of AAK1 and GAK inhibitors on HIV replication relative to untreated control.

FIG. 10(A) Compartments and micromechanical valves. A valve is created where a control channel crosses a flow channel. The resulting thin membrane in the junction between the two channels can be deflected by hydraulic actuation. Using multiplexed valve systems allows a large number of elastomeric microvalves to perform complex fluidic manipulations within these devices. FIG. 10(B) Experimental protocol. ▧ represents surface bound biotinylated anti-histidine antibodies (shown in B1 and B2). ○ represents surface bound FITC-labeled bait human protein (shown in B3). ◉ represents Cy3-labeled prey viral protein (shown in B4 and B5). 1) The microfluidic device was bonded to a glass slide and subjected to surface patterning that resulted in a circular area coated with biotinylated anti-histidine antibodies within each unit cell (see c). 2) V5-his-tagged bait human proteins were expressed off the chip using in vitro transcription/translation (TNT) mixture and were loaded into the device. 3) These proteins bound to the surface anti-his antibodies. 4) T7-tagged viral proteins were expressed off the chip by the same mammalian in vitro TNT mixture in the presence of microsomal membranes and loaded into the device along with FITC-labeled anti-V5 and Cy3-labeled anti-T7 antibodies. 5) The "sandwich valves" were closed to allow incubation of the viral protein with the human proteins and their labeling with the respective fluorescent antibodies. 6) MITOMI was then performed by actuation of the "button membrane" facilitating trapping surface-bound complexes while expelling any solution phase molecules. The "sandwich valves" were opened followed by a brief wash to remove untrapped unbound material. 7) The device was scanned by an array scanner. Trapped viral protein and surface bound human proteins were detected. The ratio of bound viral protein to expressed human protein was calculated for each data point by measuring the median signal of Cy3 to median signal of FITC (represented by ◐, shown in B7). FIG. 10(C) Surface patterning. 1) Accessible surface area was derivatized by flowing a solution of biotinylated BSA (⬠) through all flow channels. 2) A Neutravidin solution (✸) was loaded. 3) The "button" membrane was activated. 4) All remaining accessible surface area except for a circular area of 60 µm masked by the button was passivated with biotinylated solution (◖). 5) The "button" membrane was opened. 6) A solution of biotinylated-anti-his antibodies (▦) was loaded allowing specific functionalization of the previously masked circular area 7) In vitro expressed human protein (◉) bound to the biotinylated-antibodies coating the discrete circular area. Each of the described steps was followed by a PBS wash.

FIG. 13(A) AP2M1/S18 RNA ratio measured by qRT-PCR in Huh-7.5 cells transfected with a pool of four siRNAs (ON-TARGETplus SMARTpools, Dharmacon) targeting AP2M1 or a pool of non-targeting (NT) sequences at 48 hr posttransfection relative to NT contols. FIG. 13(B) AP2M1 protein levels by quantitative Western analysis in cells 48 hr posttransfection with the corresponding pooled siRNAs. Numbers represent AP2M1 to actin protein ratio relative to the NT control. FIG. 13(C) Cellular viability by alamarBlue assays 48 hr post siRNAs transfections relative to NT control. FIG. 13(D) Cells were electroporated with J6/JFH(p7-Rluc2A) at 48 hr following transfection with the indicated pooled siRNAs. HCV RNA replication in these cells by luciferase assays at 6 hr (black) and 72 hr (white) postelectroporation. FIG. 13(E) Extracellular (black) and intracellular (white) infectivity measured in naive Huh-7.5 cells infected with supernatants or clarified cell lysates derived from electroporated cells harboring the indicated siRNAs by luciferase assays, respectively. FIG. 13(F) Infectious virus production measured by limiting dilution assays. FIG. 13(G) Extracellular (black) and intracellular (white) infectivity measured by focus formation assays in naive Huh-7.5 cells infected with supernatants or clarified cell lysates derived from Huh-7.5 cells transiently depleted for AP2M1 by siRNAs and infected with culture grown J6/JFH virus (titer: $1.2 \times 10^5$ $TCID_{50}$/ml). Results are relative to NT controls. Means±s.d. (error bars) of results from at least two independent experiments are shown. RLU is relative light units. $TCID_{50}$ is 50% tissue culture infectious dose.

FIG. 14(A) quantitative confocal immunofluorescence (IF) analysis for localization of core to the ER membrane in Huh-7.5 cells infected with culture grown HCV. FIG. 14(A) and FIG. 14(B) are representative merged images of core (red) and the ER marker, calreticulin (green), demonstrating a comparable partial localization of core to the ER membrane in Huh-7.5 cells infected with WT virus (A) or with virus harboring the Y136A core mutation (B). Representative images at ×60 magnification are shown. FIG. 14(C) Colocalization analysis of Z stacks using Manders' coefficients (with a higher value representing more colocalization). Values indicate mean M2 values represented as percent colocalization (the fraction of green intensity that coincides with red intensity±s.d. (error bars); n=10-15.

DETAILED DESCRIPTION

Figure 1F:
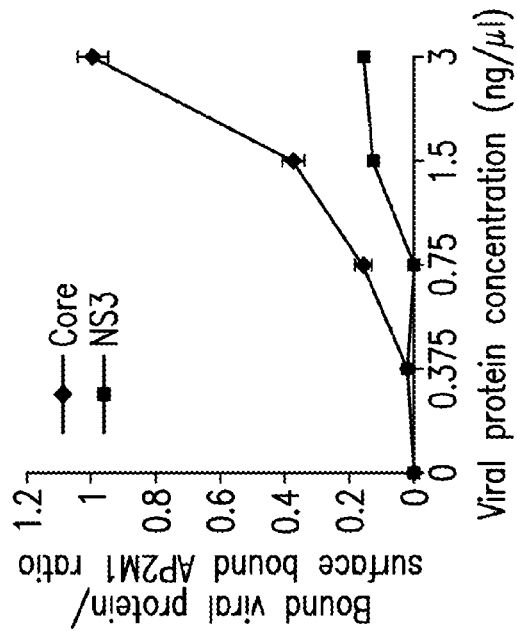

Before the present disclosure is described in greater detail, it is to be understood that this disclosure is not limited to particular embodiments described, and the embodiment of the invention as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible. As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355, NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "treatment," "treating," and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease, (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, etc.).

As used herein, the terms "prophylactically treat" or "prophylactically treating" refer to completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals, particularly pets such as dogs and cats. For diagnostic or research applications, a wide variety of mammals may be suitable subjects, including rodents (e.g., mice, rats, hamsters), rabbits, primates, and swine, such as inbred pigs and the like. The term "living host" refers to a host as noted above or another organism that is alive. The term "living host" refers to the entire host or organism and not just a part excised (e.g., a liver or other organ) from the living host.

The term "isolated compound" means a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers, as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound (e.g., an antiviral compound, as described herein) calculated in an amount sufficient to produce the desired effect in association with a pharmaceutically acceptable diluent, carrier, or vehicle. The specifications for unit dosage forms depend on the particular compound employed, the route and frequency of administration, the effect to be achieved, and the pharmacodynamics associated with each compound in the host.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that is useful in preparing a pharmaceutical composition that is generally safe, non-toxic, and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational, and the like.

The term "therapeutically effective amount" as used herein refers to that amount of an embodiment of the agent (which may be referred to as a compound, an inhibitory agent, and/or a drug) being administered that will relieve to some extent one or more of the symptoms of the disease, i.e., infection, being treated, and/or that amount that will prevent, to some extent, one or more of the symptoms of the disease, i.e., infection, that the host being treated has or is at risk of developing.

Viruses are small intracellular infectious agents that replicate via use of the host cell machinery. Virus assembly and budding of Flaviviridae remain poorly understood, although recent data suggest that the endocytic pathway may be involved, such as with Hepatitis C Virus (HCV). Host proteins are involved in these processes, although prior to the present disclosure, host proteins involved in mediating late assembly and budding were not targeted as antiviral agents. The present disclosure, however, provides antiviral methods and compositions that target host proteins for late assembly and budding. In particular, host clathrin adaptor proteins and their regulators involved in the endocytic or secretory pathways are effective targets. The role of clathrin adaptor proteins and their regulators in infectious Flaviviridae production was previously unknown. The present disclosure demonstrates that host clathrin adaptor proteins, such as AP2M1, AP1M1, AP3M1, and AP4M1, and their regulatoryo proteins, such as, but not limited to AAK1, and GAK are suitable targets for antiviral therapies. In addition, the present disclosure provides a novel viral amino acid motif that mediates interaction with a host protein.

Figure 1E:
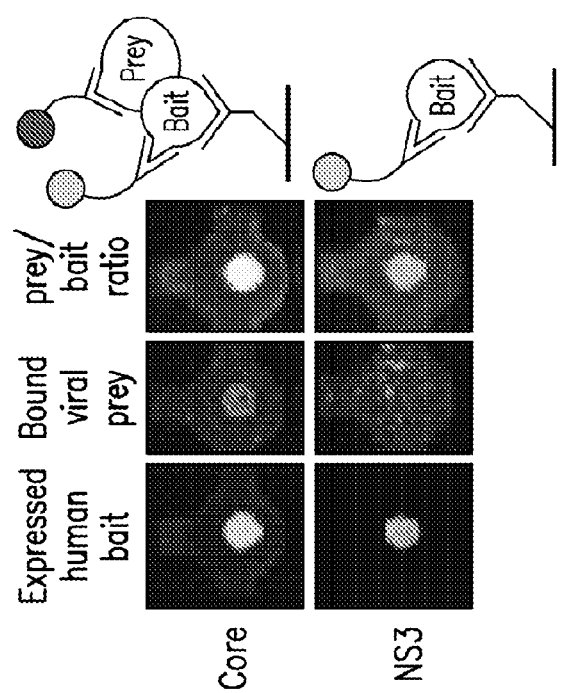

A conserved YXXΦ motif was discovered within the core protein of HCV, a 191-amino acid membrane protein that forms the viral capsid (FIG. 1). This YXXΦ motif is conserved across all HCV isolates available in databases to date. This motif was also discovered in structural proteins from other Flaviviridae and other viruses. This YXXΦ motif conforms with the YXXΦ consensus sorting signal within membrane host cargo proteins, recognized by the μ subunit of clathrin adaptor protein (AP) complexes (FIG. 1a). AP2M1 mediates clathrin-dependent endocytosis, the process by which cargo proteins are sorted into clathrin-coated pits destined for fusion with early endosomes. Recognition of the YXXΦ or dileucine motifs within retroviral proteins by AP2M1 or AP1M1 has been shown to be involved in mediating assembly and budding of retroviruses (FIG. 1b) (Batonick et al., *Virology* 342:190-200, 2005; Camus et al., *Molec Biol Cell* 18:3193-3203, 2007; Berlioz-Torrent et al., *J Virol* 73:1350-1361, 1999; Byland et al., *Molec Biol Cell* 18:414-425, 2007; Wyss et al., *J Virol* 75:2982-2992, 2001; Ohno et al., *Virology* 238:305-315, 1997; Boge et al., *J Biol Chem* 273:15773-15778, 1998; Egan et al., *J Virol* 70:6547-6556, 1996; Rowell et al., *J Immunol* 155:473-488, 1995; Lodge et al., *EMBO J* 16:695-705, 1997; Deschambeault et al., *J Virol* 73:5010-5017, 1999). However, the role of AAK1 and GAK in HIV infection has not been studied, and these mechanisms have not been targeted pharmacologically.

Accordingly, the present disclosure provides methods and compositions for treating or preventing viral infection from HCV, Flaviviridae, Flaviviridae other than HCV, HIV, Lentiviridae other than HIV, clathrin AP binding viruses, clathrin AP binding other than Flaviviridae, clathrin AP binding viruses other than HCV, or co-infections such as HCV/HIV co-infections.

Inhibition of the interaction between the viral YXXΦ motif and host adaptor proteinis, such as, but not limited to AP2M1, results in reduced infectious virus production of HCV, Flaviviridae, Flaviviridae other than HCV, clathrin AP binding viruses, clathrin AP binding viruses other than Flaviviridae, clathrin AP binding viruses other than HCV, or co-infections such as HCV/HIV co-infections. In addition, inhibition of the activity of proteins that regulate clathrin adaptor proteins may result in reduced infectious virus production of HCV, Flaviviridae, Flaviviridae other than HCV, clathrin AP binding viruses, clathrin AP binding viruses other than Flaviviridae, clathrin AP binding viruses other than HCV, or co-infections such as HCV/HIV co-infections. Thus, approaches designed to disrupt the viral YXXΦ motifs interaction with clathrin adaptor proteins, such as AP2M1 and the like, may be useful for inhibiting infectious virus production.

Regulation of the activity of many proteins occurs through the action of protein kinases and protein phophatases. GAK and AAK1 are two protein kinases that modulate the activity of AP2M1 and other μ subunits of clathrin AP complexes, indicating that administration of protein kinase inhibitors such as erlotinib, sunitinib, or PKC-412 may abolish the interaction of AP2M1 and other μ subunits of clathrin AP complexes with viral YXXΦ or dileucine motifs, thereby inhibiting viral infection from HCV, Flaviviridae, Flaviviridae other than HCV, clathrin AP binding viruses, clathrin AP binding viruses other than Flaviviridae, clathrin AP binding viruses other than HCV, HIV, Lentiviridae other than HIV, or co-infections such as HCV/HIV co-infections, as described in more detail below.

Embodiments of the present disclosure therefore provide methods of treating a viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, or any other enveloped virus that hijacks AP2M1 other μ subunits of clathrin AP complexes/AAK1/GAK, compositions (including inhibiting agents and combinations of such agents with other antiviral therapies) for treating an infection by such viruses, and the like. In particular, embodiments of the present invention provide for methods of treating infections caused by clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, and compositions for treating these infections or any other enveloped virus that binds clathrin adaptor proteins, such as AP2M1, or is regulated by AAK1 or GAK.

Embodiments of the present disclosure provide methods of prophylactically treating a viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, compositions (including inhibiting agents and combinations of such agents with other antiviral therapies) for prophylactically treating an infection by such viruses, and the like. In particular, embodiments of the present invention provide for methods of prophylactically treating HCV and/or HIV, and compositions for treating HCV and/or HIV. In an alternative embodiment, the present invention provides for methods for treating HCV/HIV infection or Flaviviridae other than HCV. While the discussion herein may describe the invention with respect to HCV, it should be noted that the disclosure relates to not only HCV, but also to clathrin AP binding viruses, Flaviviridae, Lentiviridae, HIV, co-infections, such as HCV/HIV co-infections, Flaviviridae other than HCV, clathrin AP binding viruses other than Flaviviridae, or clathrin AP binding viruses other than HCV, and compositions for treating these infections or any other enveloped virus that binds AP2M1 or other μ subunits of clathrin AP complexes or is regulated by AAK1 or GAK, or any other enveloped virus that binds clathrin adaptor proteins, such as AP2M1 and the like, or other μ subunits of clathrin AP complexes and this interaction is regulated by AAK1/GAK.

In view of the recognition that viral proteins comprising a YXXΦ or dileucine motif can mediate interaction with host proteins, embodiments of the present invention provide compositions (including pharmaceutical compositions) including an inhibiting agent that can be used to treat a host infected by a virus of the Flaviviridae family of viruses. In particular, the inhibiting agent can be used to treat hosts infected with viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV, or patients suffering from coinfections, in particular HCV and HIV or Flaviviridae other than HCV. Accordingly, two types of inhibiting agents find use herein: (1) those that inhibit interaction between a viral protein comprising the YXXΦ or dileucine motif and host clathrin adaptor proteins, such as AP2M1 andother μ subunits of clathrin AP complexes; and (2) those that inhibit kinase activity that regulates host proteins. In some embodiments, the inhibiting agent inhibits AAK1 or GAK.

As described in the Examples, it has been observed that the HCV YXXΦ motif in a structural protein binds to the host protein AP2M1. This interaction has been used to identify inhibiting agents that interfere with the interaction and thus may be candidates for clinical development as drugs for treating viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV.

Inhibiting agents described herein are useful in the treatment of viral infections, where the virus is a YXXΦ motif-containing virus, and Y is a tyrosine residue, X is any amino acid, and Φ is a bulky hydrophobic residue. These can include, but are not limited to, phenylalanine, methionine, leucine, isoleucine, and valine. Inhibiting agents described herein are useful in the treatment of viral infections, where the virus comprises a dileucine motif-containing virus. Dileucine motifs may include, but are not limited to, leucine-leucine, isoleucine-leucine, leucine-isoleucine, [D/E] XXXL[L/I], or DXXLL (where X is any amino acid). YXXΦ or dileucine motif-containing viruses include, among others, Lentiviridae, such as HIV, and Flaviviridae family viruses. Exemplary Flaviviridae include, but are not limited to, flaviviruses, pestiviruses, and hepatitis C viruses. Other YXXΦ or dileucine motif-containing viruses include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Hepatitis C virus (HCV); Kunjin virus; Central European encephalitis virus; Russian spring-summer encephalitis virus; Powassan virus; Kyasanur Forest disease virus; Ilheus virus; Apoi virus; GB virus A and B; Louping ill virus and Omsk hemorrhagic fever virus.

In an embodiment, inhibiting agents (e.g., anti-HCV agents) for use in inhibiting HCV replication and treating HCV infection, are of particular interest. Flaviviridae other than HCV and enveloped viruses other than Flaviviridae are also of interest. The HCV contemplated by the disclosure may be of any genotype (genotype 1, 2, 3, 4, 5, 6, and the like), as well as subtypes of an HCV genotype (e.g., 1a, 1b, 2a, 2b, 3a, etc.). Because HCV genotype 1 is typically the most difficult to treat, the methods and compositions of the invention for treating infections by HCV genotype 1 and genotype 1 subtypes are of particular interest. In an embodiment, HCV co-infections are of interest. In particular, HCV/HIV co-infections are of interest.

While the specification below refers to HCV, such a reference is only for clarity and is not intended to limit the disclosure as described in more detail below to HCV. As noted above, the methods and compositions of the invention can be applied to any virus possessing a YXXΦ or dileucine motif in a structural protein (e.g., viral infection from HCV, Flaviviridae, Flaviviridae other than HCV, clathrin AP binding viruses, clathrin AP binding viruses other than Flaviviridae, clathrin AP binding viruses other than HCV, co-infections such as HCV/HIV co-infections), Lentiviridae or HIV. The compositions and methods can also be applied to co-infections, and infections with Flaviviridae other than HCV, and enveloped viruses other than Flaviviridae.

The instant disclosure also describes in vitro cell-free methods of identifying agents (inhibiting agents) that modulate binding between a viral protein containing a YXXΦ or dileucine motif and a host clathrin adaptor protein such as AP2M1 or other μ subunits of clathrin AP complexes. A test agent that inhibits binding of YXXΦ or dileucine motif-containing viral proteins to host proteins including clathrin adatpor proteins, such as AP2M1 or other μ subunits of clathrin AP complexes, can be further tested for its ability to inhibit viral replication in a cell-based assay. For example, a test agent of interest can be contacted with a mammalian cell that harbors all or part of an HCV genome, and the effect of the test agent on HCV replication can be determined. Suitable cells include mammalian liver cells that are permissive for HCV replication, e.g., an immortalized human hepatocyte cell line that is permissive for HCV. For example, a suitable mammalian cell is Huh7 hepatocyte or a subclone of Huh7 hepatocyte, e.g., Huh-7.5. Suitable cell lines are described in, e.g., Blight et al. (*J Virol* 76:13001, 2002) and Zhang et al. (*J Virol* 78:1448, 2004). In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter. Other viral assay systems are known in the art.

In one embodiment, the test agents are organic moieties. In this embodiment, as is generally described in WO 94/24314, which is incorporated herein by reference, test agents are synthesized from a series of substrates that can be chemically modified. "Chemically modified" herein includes traditional chemical reactions, as well as enzymatic reactions. These substrates generally include, but are not limited to, alkyl groups (including alkanes, alkenes, alkynes, and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepines, beta-lactams, tetracyclines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which may then be tested using the present methods.

Thus, in specific embodiments, a test agent of interest (e.g., an inhibiting agent of the invention) inhibits viral replication by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of HCV replication in the absence of the test agent.

In particular, embodiments of the present invention include inhibiting agents that inhibit binding of viral proteins containing a YXXΦ or dileucine motif to host clathrin adaptor proteins such as AP2M1 or other μ subunits of clathrin AP complexes by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the binding of viral proteins containing a YXXΦ or dileucine motif to host clathrin adaptor proteins such as AP2M1 or other μ subunits of clathrin AP complexes in the absence of the test agent.

In yet another embodiment, the inhibiting agent is one that inhibits binding of a viral protein containing a YXXΦ or dileucine motif to host clathrin adaptor proteins such as AP2M1 or other μ subunits of clathrin AP complexes with a 50% inhibitory concentration ($IC_{50}$) of about 100 μM to 50 μM, about 50 μM to 25 μM, about 25 μM to 10 μM, about 10 μM to 5 μM, about 5 μM to 1 μM, about 1 μM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM.

In still yet another embodiment, the inhibiting agent inhibits binding of at least one viral protein containing a YXXΦ or dileucine motif to host clathrin adaptor proteins such as AP2M1 or other μ subunits of clathrin AP complexes. In an embodiment, the inhibiting agent inhibits binding of at least one viral protein containing a YXXΦ or dileucine motif to host proteins such as AP2M1 or other μ subunits of clathrin AP complexes with an $IC_{50}$ of less than about 500 nM, e.g., in some embodiments, the inhibiting agent inhibits binding of at least one viral protein containing a YXXΦ or dileucine motif to host structural proteins such as AP2M1 or other μ subunits of clathrin AP complexes with an $IC_{50}$ of about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, or less than about 5 nM.

In still yet another embodiment, the inhibiting agent, when contacted with a virus-infected cell (e.g., an HCV-infected liver cell), inhibits viral replication in the cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the level of viral replication in a viral-infected cell not contacted with the inhibiting agent.

In still yet another embodiment, the inhibiting agent, when contacted with an virus-infected cell (e.g., an HCV-infected liver cell), reduces the amount of infectious viral particles produced by the infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the number of infectious viral particles produced by the cell not contacted with the inhibiting agent.

In still yet another embodiment, in addition to determining the effect of a test agent on inhibition of viral proteins containing a YXXΦ or dileucine motif to host clathrin adaptor proteins such as AP2M1 or other μ subunits of clathrin AP complexes, test agents are assessed for any cytotoxic activity they may exhibit toward a living eukaryotic cell, using well-known assays, such as trypan blue dye exclusion, an MTT (3-(4,5-dimethylthiazol-2-yl)-2,5-diphenyl-2H-tetrazolium bromide) assay, and the like. Agents that do not exhibit significant cytotoxic activity may be considered preferred agents for further development as drugs.

In still yet another embodiment, the inhibiting agent, when administered in one or more doses to an individual infected with a virus as described herein (e.g., a human), reduces the viral load in the individual by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more, compared to the viral load in the individual not treated with the inhibiting agent.

Inhibiting Agents

Embodiments of the present disclosure provide for inhibiting agents that can be used to treat a host infected by a virus of the Flaviviridae family of viruses. In particular, Flaviviridae other than HCV. In particular, the inhibiting agent can be used to treat hosts infected with Hepatitis C virus or coinfections, in particular HCV+HIV. The inhibiting agent can be in one or more of the following groups: inhibitors of protein kinases AAK1 or GAK, which regulate viral protein-clathrin adaptor, such as AP2M1 (or other μ subunits of clathrin AP complexes), binding and mediate virus assembly and/or budding. Since AP2M1 and other μ subunits of clathrin AP complexes mediate various stages in the life cycles of multiple viruses, inhibition of AP2M1 and other μ subunits of clathrin AP complexes, such as by inhibition of its regulatory protein kinases or phosphatases, may affect or inhibit multiple viruses. Accordingly, the protein kinases that regulate these host proteins may be functionally relevant in other viral families. While not exclusively specific (like most compounds), the discovered protein kinase inhibitors bind AAK1 or GAK with high affinities compared to their other targets and have no effect on HCV RNA replication, demonstrating a relatively good selectivity.

Other agents that find use as inhibitors of GAK and AAK1 include, but are not limited to, RNAi, antisense, ribozymes, or small molecules that compete with erlotinib, sunitinib, or PKC-412 for binding to GAK or AAK1. In addition, inhibitors that are able to compete with YXXΦ or dileucine motifs for binding to host proteins include, but are not limited to, binding agents such as antibodies directed to YXXΦ or dileucine or against AP2M1 or other μ subunits of clathrin AP complexes. In addition, dominant-negative binding proteins or aptamers can inhibit GAK or AAK1. In another embodiment, decoy receptors or polypeptides corresponding to the YXXΦ or dileucine binding site from AP2M1 other μ subunits of clathrin AP complexes can inhibit GAK or AAK1.

Embodiments of the present invention include salts of the inhibiting agents. Embodiments of the present invention include prodrugs of the inhibiting agents. Embodiments of the invention include in compositions, pharmaceutical compositions, liquid compositions, gel compositions, and the like, each containing an inhibiting agent identified herein, and each of these compositions, in an embodiment, can be in the form of a controlled release or a sustained release formulation. In an embodiment, the inhibiting agent can be used in combination with another agent used to treat a Flaviviridae family viral infection, and as previously noted, either of the agents (the inhibiting agent and the other agent) or both of the agents can be in the form of a controlled release or a sustained release. In some instances, the term "inhibiting agent" may be referred to as an active agent or drug.

Pharmaceutical Formulations and Routes of Administration

Embodiments of the present disclosure include one or more inhibiting agents identified herein and formulated with one or more pharmaceutically acceptable excipients, diluents, carriers and/or adjuvants. In addition, embodiments of the present invention include such inhibiting agents formulated with one or more pharmaceutically acceptable auxiliary substances. In particular, one or more inhibiting agents can be formulated with one or more pharmaceutically acceptable excipients, diluents, carriers, and/or adjuvants to provide an embodiment of a composition of the invention.

In an embodiment, the inhibiting agent can be combined with another antiviral agent to prepare a composition of the invention, and the composition can include one or more pharmaceutically acceptable excipients, diluents, carriers and/or adjuvants.

In an embodiment, an inhibiting agent that inhibits binding of a protein containing a YXXΦ or dileucine motif to a host clathrin adaptor protein such as AP2M1 or other subunits of clathrin AP complexes (referred to below as "a subject active agent" or "drug") can be formulated with one or more pharmaceutically acceptable excipients, diluents, carriers, and/or adjuvants.

A wide variety of pharmaceutically acceptable excipients are known in the art. Pharmaceutically acceptable excipients have been amply described in a variety of publications, including, for example, Gennaro (2000), "Remington: The Science and Practice of Pharmacy"; Pharmaceutical Dosage Forms and Drug Delivery Systems (1999); and Handbook of Pharmaceutical Excipients (2000).

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents, and the like, are readily available to the public.

In an embodiment of the present disclosure, the inhibiting agent is administered to the host using any means capable of resulting in the desired effect (e.g., reduction in viral load, reduction in liver fibrosis, increase in liver function, and the like). Thus, the inhibiting agent can be incorporated into a variety of formulations for therapeutic administration. For example, the inhibiting agent can be formulated into pharmaceutical compositions by combination with appropriate, pharmaceutically acceptable carriers or diluents, and may be formulated into preparations in solid, semi-solid, liquid, or gaseous forms, such as tablets, capsules, powders, granules, ointments, solutions, suppositories, injections, inhalants, and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch, or potato starch; with binders, such as crystalline cellulose, cellulose derivatives, acacia, corn starch, or gelatins; with disintegrators, such as corn starch, potato starch, or sodium carboxymethylcellulose; with lubricants, such as talc or magnesium stearate; and if desired, with diluents, buffering agents, moistening agents, preservatives, and flavoring agents.

Embodiments of the inhibiting agent can be formulated into preparations for injection by dissolving, suspending, or emulsifying them in an aqueous or nonaqueous solvent, such as vegetable or other similar oils, synthetic aliphatic acid glycerides, esters of higher aliphatic acids, or propylene glycol; and if desired, with conventional additives such as solubilizers, isotonic agents, suspending agents, emulsifying agents, stabilizers, and preservatives.

Embodiments of the inhibiting agent can be utilized in aerosol formulation to be administered via inhalation. Embodiments of the inhibiting agent can be formulated into pressurized acceptable propellants such as dichlorodifluoromethane, propane, nitrogen and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes, and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet, or suppository, contains a predetermined amount of the composition containing one or more inhibiting agents. Similarly, unit dosage forms for injection or intravenous administration may comprise the inhibiting agent in a composition as a solution in sterile water, normal saline, or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles in accordance with the invention.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the inhibiting agent can be accomplished using any of a variety of refillable pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed Infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, 17th edition, 1985. The composition or formulation to be administered will, in any event, contain a quantity of the inhibiting agent adequate to achieve the desired state in the subject being treated.

Compositions of the present invention include those that comprise a sustained-release or controlled release matrix. In addition, embodiments of the present invention can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone, and silicone. Illustrative biodegradable matrices include a polylactide matrix, a polyglycolide matrix, and a polylactide co-glycolide (co-polymers of lactic acid and glycolic acid) matrix.

In another embodiment, the pharmaceutical composition of the present disclosure (as well as combination compositions) is delivered in a controlled release system. For example, the inhibiting agent may be administered using intravenous infusion, an implantable osmotic pump, a transdermal patch, liposomes, or other modes of administration. In one embodiment, a pump may be used (Sefton 1987; Buchwald et al. 1980; Saudek et al. 1989). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990).

In another embodiment, the compositions of the present invention (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

Treatment Methods

Embodiments of the present invention include methods of treating an infection by viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV. In particular, inhibiting agents described herein can be used to treat an infection by a virus of the Flaviviridae family of viruses. In an embodiment, the present disclosure provides a method of treating a host infected with a virus as described above by administering to the host a therapeutically effective amount of an inhibiting agent in one or more doses, to reduce the viral load in the host.

Embodiments of the present invention include methods of prophylactically treating an infection by a viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV. In particular, inhibiting agents described herein can be used to prophylactically treat an infection by a virus of the Flaviviridae family of viruses. In an embodiment, the present disclosure provides a method of prophylactically treating a host infected with a virus from the Flaviviridae family of viruses by administering to the host a therapeutically effective amount of an inhibiting agent in one or more doses, to reduce the viral load in the host. In an embodiment, a method of prophylactically treating a host infected with a virus from the Flaviviridae family of viruses, the method comprising administering to the host a therapeutically effective amount of an inhibiting agent to reduce the viral load in the host. Additional details regarding clemizole and dosing of clemizole is described above.

In an embodiment, inhibiting agents described herein are used in combination with another agent (e.g., an antiviral agent) to treat an infection with viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV. In an embodiment, inhibiting agents described herein are used in combination with another agent (e.g., an antiviral agent) to prophylactically treat an infection with a virus from the Flaviviridae family of viruses. Embodiments of the method involve administering to an individual in need thereof one or more inhibiting agents that inhibit binding of viral proteins containing a YXXΦ or dileucine motif to host clathrin adaptor proteins such as AP2M1 or other μ subunits of clathrin AP complexes. In an embodiment, the present invention provides methods of treating a flavivirus infection, e.g., an HCV infection, and methods of reducing liver fibrosis that may occur as sequelae of an HCV infection.

In an embodiment, the inhibiting agent includes one or more of inhibiting agents described above. In various embodiments, the inhibiting agent is a protein kinase inhibitor, such as inhibitors of AAK1 or GAK, which regulates viral protein-AP2M1 binding or binding of a viral protein to other µ subunits of clathrin AP complexes and mediate virus assembly and/or budding, or variants of these proteins thereof.

In an embodiment, an effective amount of the inhibiting agent is an amount that, when administered in one or more doses to a host (e.g., human) in need thereof, reduces viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR (qRT-PCR) (Amplicor HCV Monitor™, Roche Molecular Systems, New Jersey); and a branched DNA signal amplification assay [Quantiplex™ HCV RNA Assay (bDNA), Chiron Corp., Emeryville, Calif.]. See, e.g., Gretch et al. (1995). Also of interest is a nucleic acid test (NAT) sold by Chiron Corporation under the trade name Procleix™, which NAT simultaneously tests for the presence of HIV-1 and HCV (Vargo et al. 2002).

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Embodiments of the present disclosure provide methods, inhibiting agents, and pharmaceutical formulations useful in the treatment of patients suffering from a viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV. In one embodiment, the patient is co-infected with Flaviviridae other than HCV. In one embodiment, the patient is infected with HCV but is not known to be infected with another virus, including, but not limited to, HIV. In another embodiment, the patient is infected with HCV and one or more additional viruses, including, but not limited to, HIV. In one embodiment, the patient is treated for a viral infection by administering only a single inhibiting agent as described herein as useful in the treatment of HCV infection. In another embodiment, the patient is treated for a viral infection by administering both an inhibiting agent described herein as useful in the treatment of HCV infection as well as one or more additional agents known to be useful in the treatment of viral infection, including, but not limited to drugs for the treatment of HIV, such as Atripla, Complera, Combivir, Retrovir, Truvada, Viracept, Fuzeon, Selzentry, Isentress, or the like. In one embodiment, the one or more additional agents does not include a CCR-5 antagonist. In another embodiment, the one or more additional agents does include a CCR-5 antagonist, and the patient is infected with HCV but not known to be infected (or is not infected) with HIV.

Dosages

Embodiments of the inhibiting agent can be administered to a host in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose.

In an embodiment, the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of the specific inhibiting agent administered, the severity of the symptoms and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the inhibiting agent is administered continuously.

The duration of administration of the inhibiting agent, e.g., the period of time over which the inhibiting agent is administered, can vary, depending on any of a variety of factors, e.g., patient response, etc. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

Routes of Administration

Embodiments of the present invention provide methods and compositions for the administration of the inhibiting agent to a host (e.g., a human) using any available method and route suitable for drug delivery, including in vivo and ex vivo methods, as well as systemic and localized routes of administration.

Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

Combination Therapies

Embodiments of the present invention include methods, inhibiting agents, and pharmaceutical formulations for the treatment of viral infection. Embodiments of the inhibiting agents and pharmaceutical formulations useful in the methods of the present disclosure can be employed in combination with other antiviral agents to treat viral infection. In an embodiment, in accordance with the methods of the present invention, an inhibiting agent that is used to treat a host infected by viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV is used in combination with one or more other antiviral agents to treat the infection. In an embodiment, in accordance with the methods of the present invention, an inhibiting agent that prevents the binding of at least one viral protein containing a YXXΦ or dileucine motif to host proteins such as AP2M1 or other µ subunits of clathrin AP complexes (also referred to herein as an "HCV YXXΦ or dileucine antagonist") can be used in combination with one or more other antiviral agents to treat viral infection.

For instance, current medical practice to treat HCV infection typically employs combination therapy with ribavirin (such as Rebetol or Copegus), either an interferon-alpha (such as interferon alpha 2b) or pegylated interferon (such as Pegasys, marketed by Roche, or PEG-Intron, marketed by Schering Plough), and a protease inhibitor. In accordance with the methods of the present disclosure, an inhibiting compound can be used in combination with these standard therapies to treat HCV infection.

A number of HCV protease and polymerase inhibitors are either approved or in development for the treatment of HCV infection, and in accordance with the methods of the present disclosure, co-administration of an inhibiting agent that prevents the binding of at least one viral protein containing a YXXΦ or dileucine motif to host proteins such as AP2M1 or other µ subunits of clathrin AP complexes and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

In accordance with the methods of the present disclosure, co-administration of an inhibiting agent that prevents the binding of at least one viral protein containing a YXXΦ or dileucine motif to host proteins such as AP2M1 or other µ subunits of clathrin AP complexes and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128 (Roche/Pharmasset), GS-9190 (Gilead), MK-0608 (Merck), PSI-6130 (Pharmasset), and PFE-868,554 (PFE). In an embodiment, the method provides combination treatments with agents that inhibit AAK1 and GAK.

A number of toll-like receptor (TLR) agonists are in development for the treatment of HCV infection, and in accordance with the methods of the present disclosure, co-administration of a YXXΦ or dileucine antagonist that prevents the binding of at least one viral protein containing a YXXΦ or dileucine motif to host proteins such as AP2M1 or other µ subunits of clathrin AP complexes and a TLR agonist can be efficacious in the treatment of HCV. In one embodiment, an interferon alpha and/or a nucleoside analog such as ribavirin and/or an HCV protease inhibitor and/or an HCV RNA polymerase inhibitor is/are also employed in this combination therapy. Suitable TLR agonists include, but are not limited to, TLR7 agonists [i.e., ANA245 and ANA975 (Anadys/Novartis)] and TLR9 agonists [i.e., Actilon (Coley) and IMO-2125 (Idera)].

A number of thiazolide derivatives are in development for the treatment of HCV infection, and in accordance with the methods of the present disclosure, co-administration of an antagonist that prevents the binding of at least one viral protein containing a YXXΦ or dileucine motif to host proteins such as AP2M1 or other μ subunits of clathrin AP complexes, and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the present disclosure, co-administration of an inhibiting agent that prevents the binding of at least one viral protein containing a YXXΦ or dileucine motif to host proteins such as AP2M1 or other μ subunits of clathrin AP complexes, and a cyclophilin inhibitor [i.e., NIM-811 (Novartis) and DEBIO-025 (Debiopharm)] and/or an alpha-glucosidase inhibitor [i.e., Celgosivir (Migenix)] and/or one or more agents from one or more of the other classes of HCV therapeutic agents discussed herein is used to treat HCV infection.

Other agents that can be used in combination with inhibiting agents of the present disclosure that prevent the binding of at least one viral protein containing a YXXΦ or dileucine motif to host proteins such as AP2M1 or other μ subunits of clathrin AP complexes include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBC1D20 and/or NS5A's interaction with TBC1D20 (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/0199174, incorporated herein by reference); (iv) agents inhibiting membrane association mediated by the HCV amphipathic helices, such as those found in NS5A, NS4B, and NS5B (see PCT publication WO 2002/089731, supra), (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathways (see US patent application publications 2008/0118511, 2007/0065427, 2007/0122378, incorporated herein by reference); and (xi) agents targeting HCV amphipathic helix function, such as AH2 inhibitors.

In another embodiment of the present disclosure, an inhibiting agent that prevents the binding of at least one viral protein containing a YXXΦ or dileucine motif to host proteins such as AP2M1 or other μ subunits of clathrin AP complexes is used in combination with one or more drugs capable of treating an HIV infection to treat a patient that is co-infected with HIV and HCV. In another embodiment of the present disclosure, an inhibiting agent that prevents the binding of at least one viral protein containing a YXXΦ or dileucine motif to host proteins such as AP2M1 or other μ subunits of clathrin AP complexes is used in combination with one or more drugs capable of treating an HBV infection to treat a patient that is co-infected with HBV and HCV. In an embodiment, an inhibiting agent that prevents the binding of at least one viral protein containing a YXXΦ or dileucine motif to host proteins such as AP2M1 or other μ subunits of clathrin AP complexes is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, etc.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, $O_2$, $O_2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, $O_2,O_2$-anhydro-β-L-arabinofuranosyluracil, 2'-deoxy-β-L-uridine, 3'5'-Di-O-benzoyl-2'-deoxy-4-thio β-L-uridine, 2'-deoxy-β-L-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204; 6,534,523; 6,420,380; 6,410,531; 6,329,417; 6,329,379; and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309; 6,608,067; and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003); NS3 inhibitor BILN 2061 (Boehringer-Ingelheim; Lamarre et al. (2002), and Lamarre et al. (2003); NS3 inhibitor VX-950 (Vertex Pharmaceuticals; Kwong et al. (2003); NS3 inhibitor SCH6 (Abib et al. (2003); Program and Abstracts of the 54$^{th}$ Annual Meeting of the American Association for the Study of Liver Diseases (AASLD, 2003); any of the NS3 protease inhibitors disclosed in WO 99/07733, WO 99/07734, WO 00/09558, WO 00/09543, WO 00/59929, or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126, and 127 disclosed in the table of pages 224-226 in WO 02/060926); an NS3 protease inhibitor as disclosed in any one of U.S. Patent Publication Nos. 2003/019067, 2003/0187018, and 2003/0186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B.

In an embodiment, the at least one additional suitable therapeutic agent includes NS5B inhibitors. Suitable HCV non-structural protein-5 (N55; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003); a benzothiadiazine compound as disclosed in Dhanak et al. (2002); an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α. can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable a interferons include, but are not limited to, naturally-occurring IFN-α (including, but not limited to, naturally occurring IFN-α2a, IFN-α2b); recombinant interferon α-2b such as Intron-A interferon available from Schering Corporation, Kenilworth, N.J.; recombinant interferon α-2a such as Roferon interferon available from Hoffmann-La Roche, Nutley, N.J.; recombinant interferon α-2C such as Berofor α2 interferon available from Boehringer Ingelheim Pharmaceutical, Inc., Ridgefield, Conn.; interferon α-n1, a purified blend of natural α interferons such as Sumiferon available from Sumitomo, Japan or as Wellferon interferon α-n1 (INS) available from the Glaxo-Wellcome Ltd., London, Great Britain; and interferon α-n3 a mixture of natural α interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen™, InterMune, Inc., Brisbane, Calif.). IFN-con$_1$ is the consensus interferon agent in the Infergen™ alfacon-1 product. The Infergen™ consensus interferon product is referred to herein by its brand name (Infergen™) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ [a fusion product of human albumin and IFN-α; Human Genome Sciences; see, e.g., Osborn et al. (2002)]. Also suitable for use in the present disclosure are gene-shuffled forms of IFN-α. See, e.g., Masci et al. (2003). Other suitable interferons include), Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen™, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as PKC-412, erlotinib, sunitinib, and the like, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

For example, HCV replication assays employing a luciferase reporter-linked HCV genome in the presence of various combinations of PKC-412, erlotinib, sunitinib, and the like. In such assays, luciferase activity is directly proportional to HCV RNA genome replication.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids. In an embodiment, the disclosure provides a method of treatment with agents that inhibit GAK and agents that inhibit AAK1. In an embodiment, such co-treatment provides synergistic effects, such as antiviral effects.

Hosts Suitable for Treatment

Hosts suitable for treatment with an embodiment of the inhibiting agent or an embodiment of the method include hosts who are infected with viral infection from clathrin AP binding viruses, Flaviviridae, Lentiviridae, HCV, HIV, co-infections, such as HCV/HIV co-infections, Flaviviridae other than HCV, clathrin AP binding viruses other than Flaviviridae, or clathrin AP binding viruses other than HCV. As used herein, the term Flaviviridae includes any member of the family Flaviviridae, including, but not limited to, Dengue virus, including Dengue virus 1, Dengue virus 2, Dengue virus 3, Dengue virus 4 (see, e.g., GenBank Accession Nos. M23027, M19197, A34774, and M14931); Yellow Fever Virus; West Nile Virus; Japanese Encephalitis Virus; St. Louis Encephalitis Virus; Bovine Viral Diarrhea Virus (BVDV); and Hepatitis C Virus (HCV); and any serotype, strain, genotype, subtype, quasispecies, or isolate of any of the foregoing. Where the Flaviviridae is HCV, the HCV is any of a number of genotypes, subtypes, or quasispecies, including, e.g., genotype 1, including 1a and 1b, 2, 3, 4, 6, etc. and subtypes (e.g., 2a, 2b, 3a, 4a, 4c, etc.), and quasispecies.

Hosts suitable for treatment with embodiments of the present invention include treatment failure patients. The term "treatment failure patients" (or "treatment failures") as used herein generally refers to HCV-infected patients who failed to respond to previous therapy for HCV (referred to as "non-responders") or who initially responded to previous therapy, but in whom the therapeutic response was not maintained (referred to as "relapsers"). The previous therapy generally can include treatment with any antiviral agent other than an inhibiting agent of the present disclosure.

Hosts suitable for treatment with embodiments of the present disclosure include individuals who have been clinically diagnosed as infected with HCV. Individuals who are infected with HCV can be identified by detecting HCV RNA in their blood, and/or having an anti-HCV antibody in their serum.

Individuals who are clinically diagnosed as infected with HCV include naive individuals (e.g., individuals not previously treated for HCV).

Hosts suitable for treatment with embodiments of the present disclosure include individuals who have any detectable HCV titer. The patient may be infected with any HCV genotype (genotype 1, including 1a and 1b, 2, 3, 4, 6, etc. and subtypes (e.g., 2a, 2b, 3a, etc.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior antiviral treatment, or who have a contraindication to therapy with a known antiviral agent.

In an embodiment, HCV-positive hosts with stage 3 or 4 liver fibrosis according to the METAVIR scoring system, which is known in the art, are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system, all of which are known in the art). In an embodiment, the method finds use in treatment of HCV post liver transplantation for HCV induced hepatocellular carcinoma. In an embodiment, this serves to prevent re-infection of the graft.

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy.

In an embodiment, the method provides treating patients infected with viruses as described herein, particularly those infected with HCV who also are afflicted with cancer, such as hepatic cancer.

Assays

The present disclosure also provides in vitro and cell-based methods of screening for antiviral agents. In one embodiment, the disclosure provides methods for detecting interaction between the YXXΦ motif and host proteins. In one embodiment, the present disclosure provides a binding assay to detect proteins or agents that inhibit binding of YXXΦ or dileucine motifs to AP2M1 or other µ subunits of clathrin AP complexes. For instance, the disclosure provides a method in which candidate agents as described herein are contacted with a Flaviviridae and AP2M1 or other µ subunits of clathrin AP complexes. Binding of the Flaviviridae to the proteins is detected as is known in the art. Reduced activity in the presence of a candidate agent relative to controls indicates identification of a binding inhibitor. In another embodiment, cell-based binding assays are used. In another embodiment, cell assays are used to screen for the effects on viral assembly or budding. In this embodiment, candidate agents are contacted with a Flaviviridae and a cell expressing AP2M1 or other μ subunits of clathrin AP complexes. Cellular effects, such as viral budding or assembly, or binding between the Flaviviridae and cell can be assayed by methods known in the art. In one embodiment, a replication assay is used. An example of a replication assay is outlined in U.S. patent application publication 2011/0052536 A1, which is expressly incorporated herein by reference. Reduced binding, budding, or assembly and the like, of the virus in the presence of the candidate agent relative to controls indicates identification of a binding inhibitor or antiviral agent. In some embodiments, in vitro microfluidics affinity assay, as known in the art, is also used to enable detection of weak and transient protein interactions.

In one embodiment, protein-fragment complementation assays, as described herein and as are known in the art, are used to validate interaction between core and AP2M1. In another embodiment, a co-immunprecipitation assay is used to identify interaction between the proteins.

EXAMPLES

The following examples are included to demonstrate preferred embodiments of the invention and to set forth a clear understanding of the principles of the disclosure. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Many variations and modifications may be made to the above-described embodiments of the disclosure without departing substantially from the spirit and principles of the disclosure. All such modifications and variations are intended to be included herein within the scope of this disclosure.

Example 1

Identification of a YXXΦ Motif within HCV Core

Inspection of the primary sequence of the HCV core protein reveals a conserved YIP(V/L) motif within the second domain (D2) of the protein (FIGS. 1A, D). This motif conforms to the YXXΦ sorting signal consensus recognized by AP2M1 (Ohno, *J Cell Sci* 119:3719-3721, 2006; Nakatsu et al., *Cell Struct Funct* 28:419-429, 2003; Owen et al., *Ann Rev Cell Devel Biol* 20:153-191, 2004).

Core Binds AP2M1

Figure 9A:
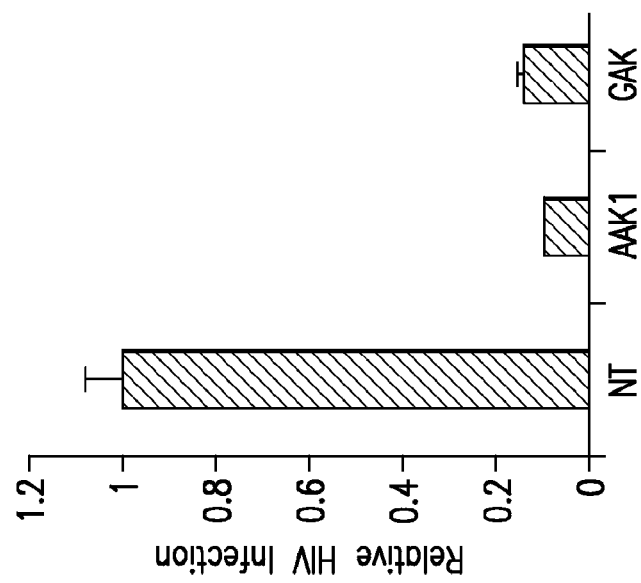
FIG. 9A-B: Shows that AAK1 and GAK depletion or pharmacological inhibition abrogates HIV-1 replication in TZM-b1 cells (CXCR4-positive HeLa cells that express CD4 and CCR5 and also contain integrated reporter genes for luciferase and E. coli β-galactosidase, both under the control of an HIV long-terminal repeat sequence (tat gene)).
Figure 9B:
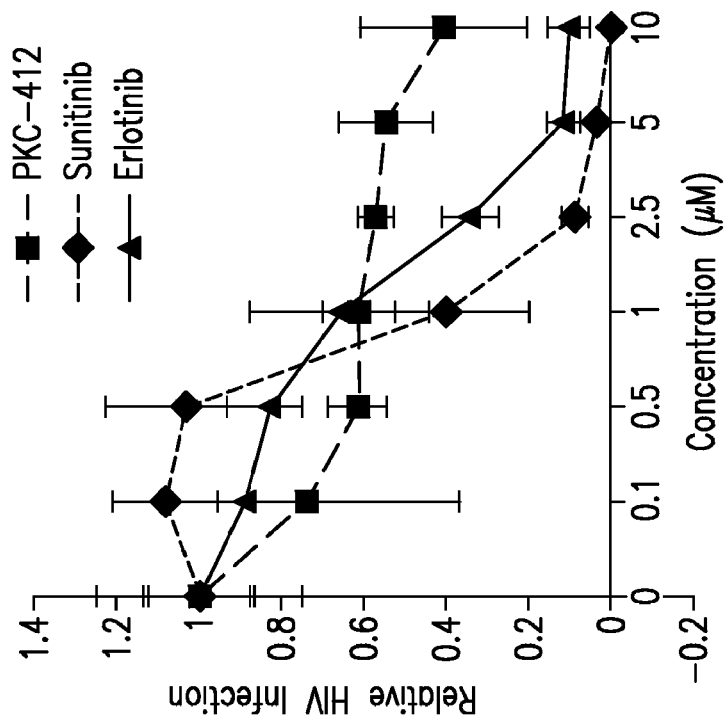

Interactions of sorting signals with clathrin adaptors and endocytic components are typically weak (Kd of binding at a μM range), transient (Nakatsu et al., *Cell Struct Funct* 28:419-429, 2003; Aguilar et al., *J Biol Chem* 276:13145-13152, 2001), and involve membrane proteins, thus difficult to study by standard technologies (Cusick et al., *Hum Mol Genet* 2005; Bailer *Curr Opin Microbiol* 12:453-459, 2009). To determine whether HCV core binds AP2M1, proteomic platforms that overcome these challenges were used. In vitro microfluidics affinity assays are based on mechanical trapping of molecular interactions (MITOMI), which eliminates the off-rate problem facing current platforms, and thus allows studying weak and transient interactions, with nanoliter protein consumption (Maerkl et al., *Science* 315:233-237, 2007; Einav et al., *Nat Biotech* 26:1019-1027, 2008; Gerber et al., *Nat Meth* 6:71-74, 2009). A microfluidics format that enables a high fidelity analysis of protein-protein interactions (P-PIs) was used (Gerber et al., *Nat Meth* 6:71-74, 2009). In vitro protein expression in the presence of microsomal membranes and binding experiments with MITOMI were performed essentially as described (Maerkl et al., *Science* 315:233-237, 2007; Einav et al., *Nat Biotech* 26:1019-1027, 2008; Gerber et al., *Nat Meth* 6:71-74, 2009) (FIG. 9). These assays detected binding of AP2M1 to core. The degree of binding correlated with increasing core concentration (FIG. 1F). Background binding of AP2M1 to a control HCV protein, NS3, was 4-20 fold lower and did not increase significantly with increased protein concentration.

Figure 2A:
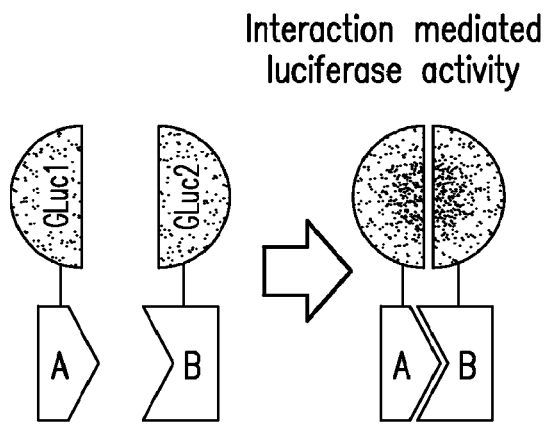
FIG. 2A-E: Shows a viral core binding AP2M1 in cells and in the context of HCV infection.
Figure 2B:
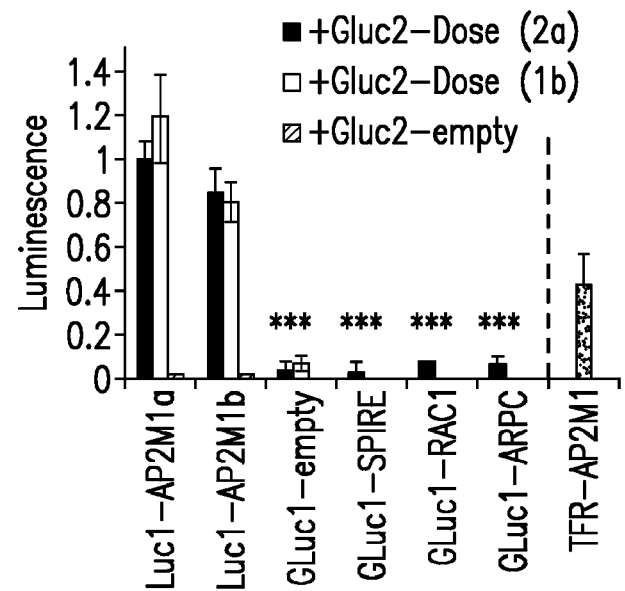
Figure 2C:
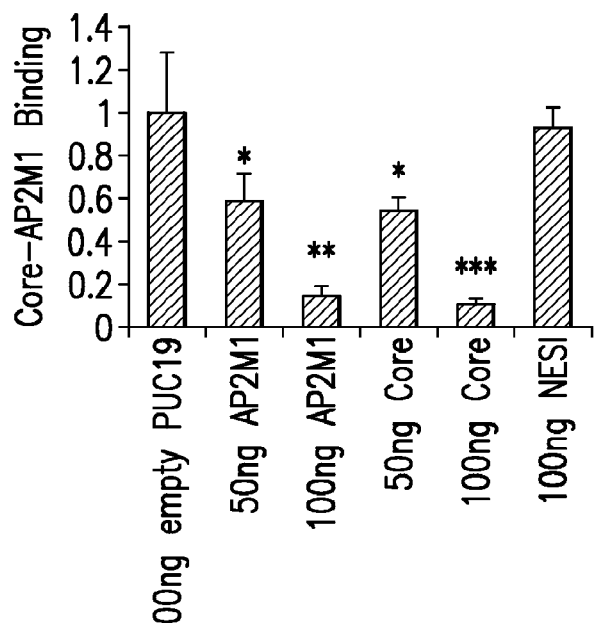

To determine whether the core-AP2M1 interaction occurs in cells, protein-fragment complementation assays (PCAs) based on reversible reconstitution of a Gaussia princeps luciferase reporter was used (FIG. 2A). The current format was optimized for improved signal, thus providing a highly sensitive means for measuring challenging P-PIs (Cassonnet et al., *Nat Meth* 8:990-992, 2011). Significant luciferase signal was detected in Huh-7.5 cells cotransfected with plasmids encoding the two reporter fragments fused to the prey and bait proteins (GLuc1-AP2M1 and GLuc2-core). Background levels of binding were detected in cells cotransfected with either the GLuc1-AP2M1 or GLuc2-core constructs and the empty reciprocal vector, the two empty GLuc vectors, or GLuc1 fused to three unrelated proteins (SPIRE, RAC1, and ARPC). The apparent affinity of AP2M1 to core was higher than to transferrin receptor (TFR), a host cargo protein harboring a YXXΦ signal, known to be recognized by AP2M1 (Gminard et al., *Traffic* 5, 181-193, 2004) (FIG. 2B). Binding was not genotype-specific, as core proteins derived from either the 2a (Lindenbach et al., *Science* 309:623-626, 2005) or 1b (Lohmann et al., *Science* 285: 110-113, 1999) genotypes demonstrated comparable levels of AP2M1 binding. Furthermore, there were no significant differences in core binding to the two isoforms of AP2M1 (a/b) (FIG. 2B). Comparable results were demonstrated in Huh-7.5 (human hepatoma derived) cells, representing the most relevant cell model (FIG. 2B), and 293T cells (data not shown). Binding appeared specific, as increasing concentrations of free core or AP2M1, but not nuclear export signal-interacting protein (NESI), a control protein involved in mediating hepatitis D virus assembly (Wang et al., *J Virol* 79:8113-8120, 2005), progressively decreased core-AP2M1 binding (FIG. 2C).

Figure 2D:
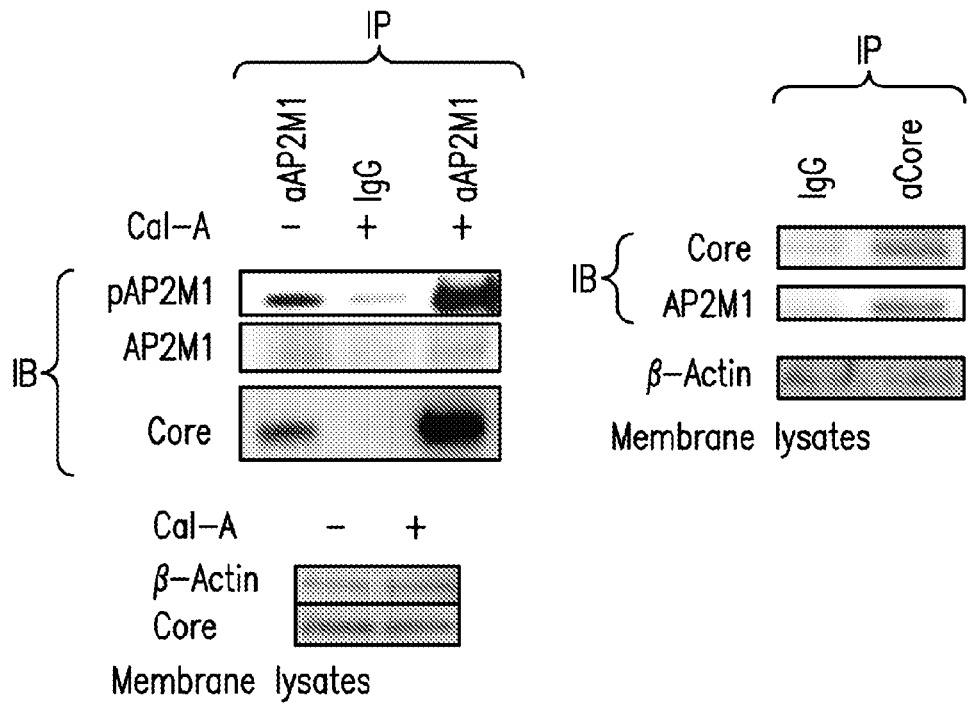
Figure 2E:
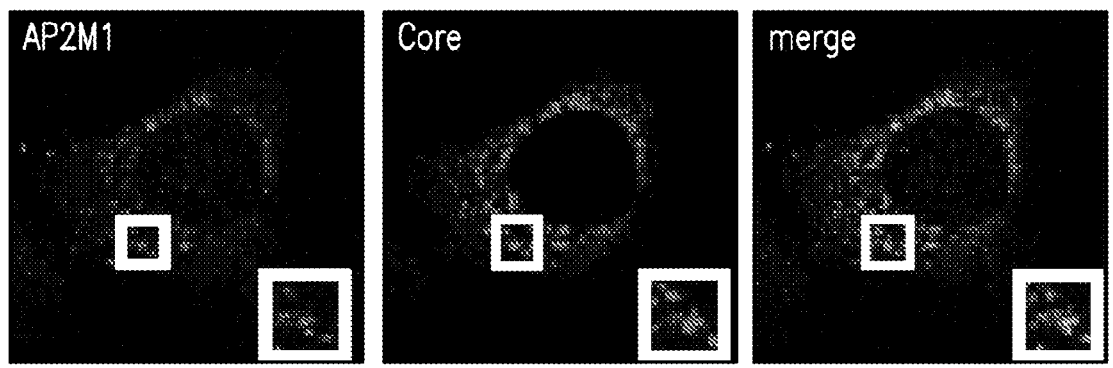

To determine whether core binds AP2M1 in the context of authentic HCV infection, co-immunoprecipitation assays in membrane fractions prepared from Huh-7.5 cells infected with cell culture-grown HCV (J6/JFH) were performed (Lindenbach et al., *Science* 309:623-626, 2005). AP2M1 could bring down core when anti-AP2M1 antibodies but not IgG controls were added to the membrane lysates. Binding was significantly augmented by calyculin A [an inhibitor of AP2M1 dephosphorylation, which "locks" AP2M1 in its YXXΦ binding active conformation (Ricotta et al., *J Biol Chem* 283:5510-5517, 2008)] (FIG. 2D). Binding in reciprocal conditions was similarly demonstrated (FIG. 2D). Colocalization of core with AP2M1 in Huh-7.5 cells 72 hr following electroporation with J6/JFH HCV RNA was also investigated. Quantitative confocal immunofluorescence (IF) analysis revealed extensive colocalization of core and AP2M1 in these cells (with 67±6% colocalization of AP2M1 stained puncta with core) (FIG. 2E).

Core's YXXΦ Motif in AP2M1 Binding and HCV Assembly

Figure 3B:
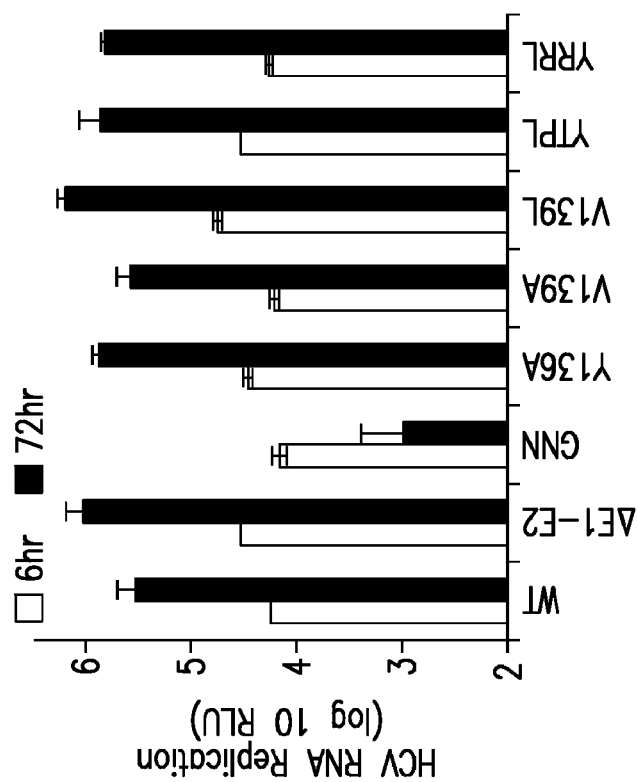
FIG. 3A-H: Shows a core YXXΦ motif mediating AP2M1 binding and viral assembly, functionally interchangeable with other YXXΦ signals.
Figure 3A:
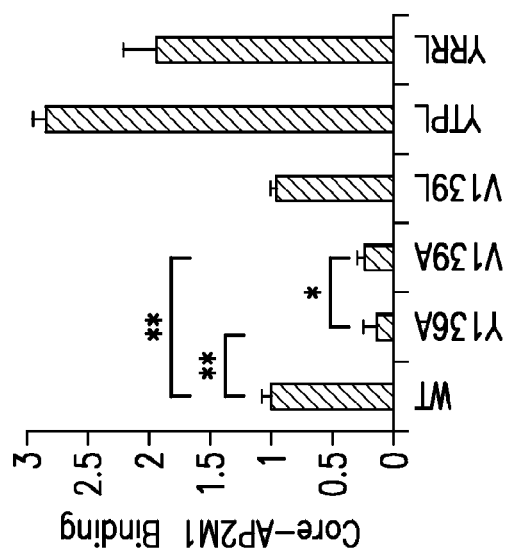
Figure 3D:
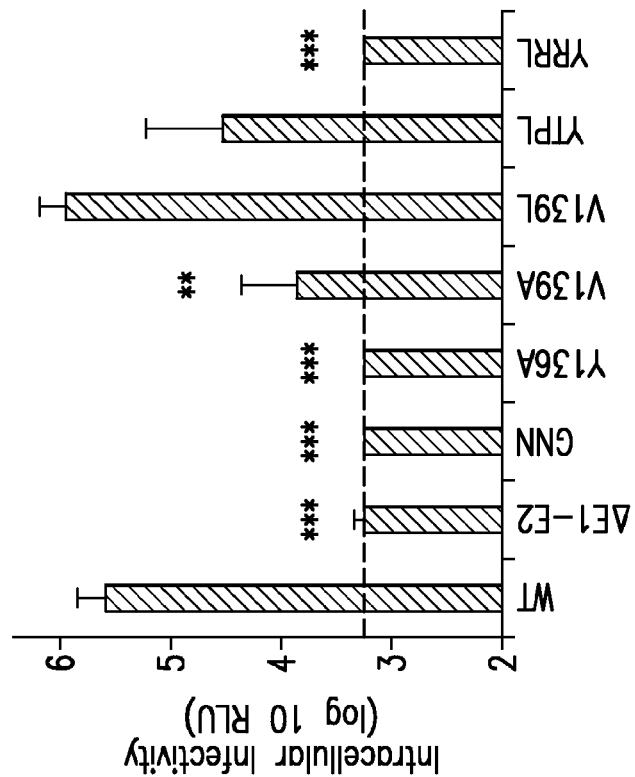
Figure 3C:
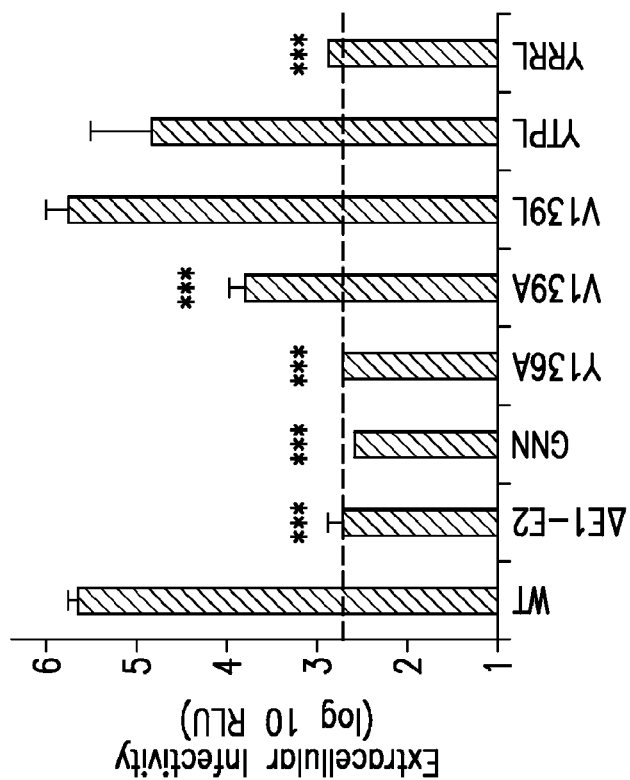
Figures 3E, 3F:
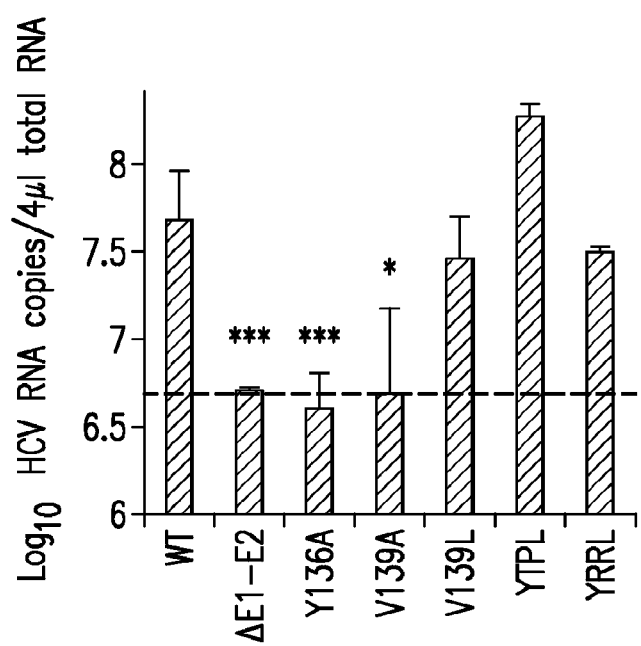
Figure 3H:
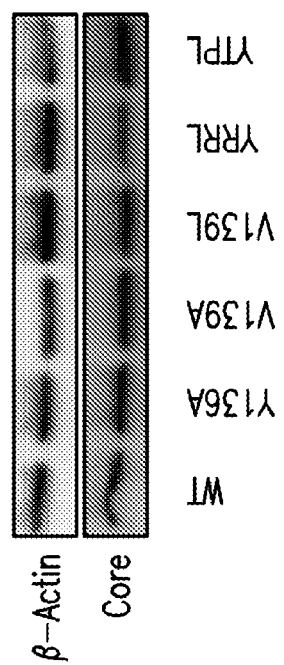
Figure 3G:
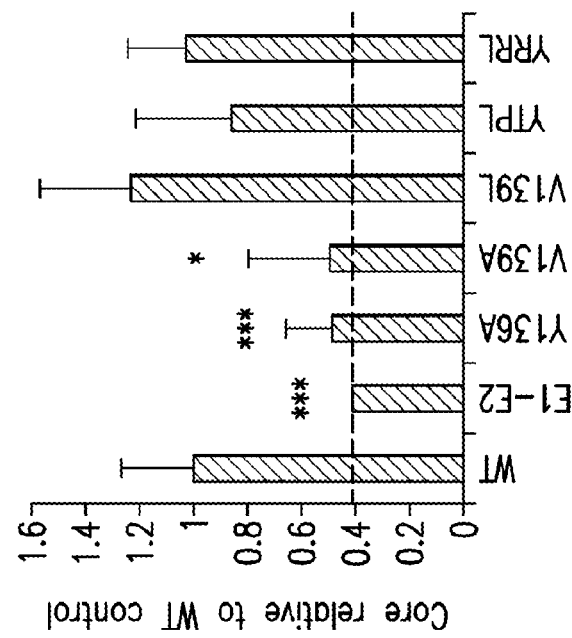
Figure 11:
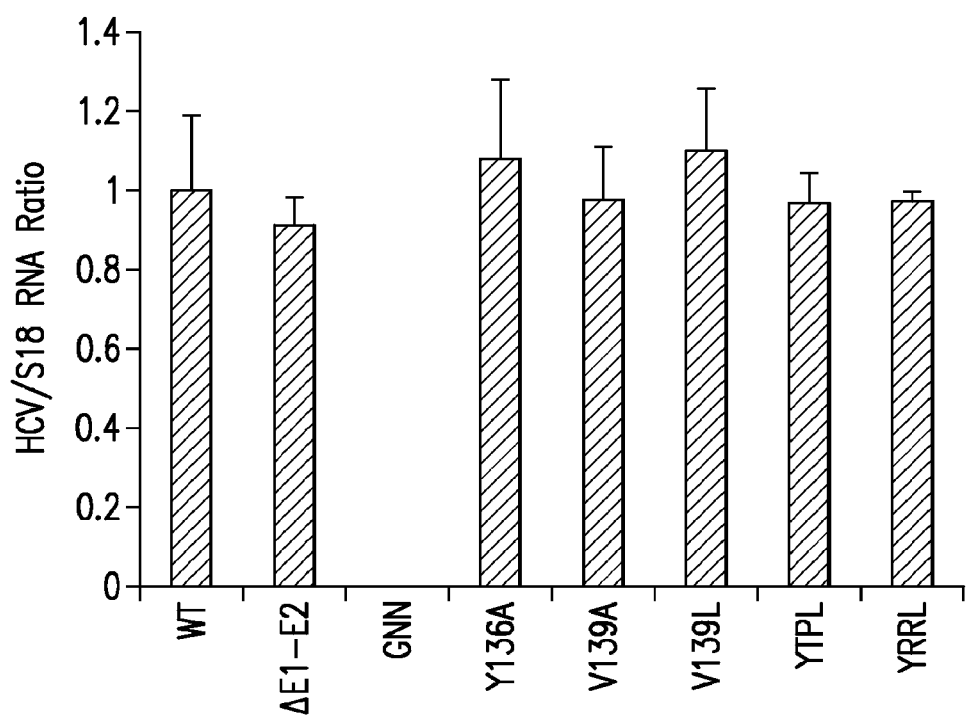
FIG. 11: Shows that the core's YXXΦ mutations do not affect HCV RNA replication by qRT-PCR assays. HCV RNA replication, by qRT-PCR in Huh-7.5 cells 72 hr following electroporation with J6/JFH(p7-Rluc2A) harboring the corresponding core's YXXΦ mutations relative to WT control. ΔE1-E2 is an assembly defective control. GNN is a replication defective polymerase mutant. Means and s.d. (error bars) of results from two independent experiments in triplicates are shown.
Figure 12:
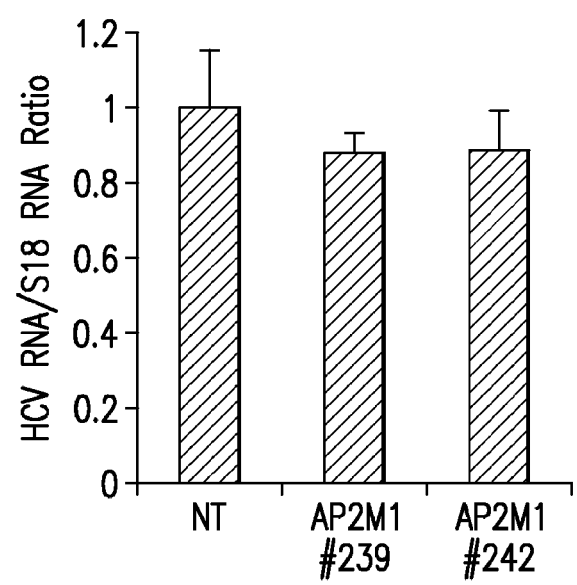
FIG. 12: Shows that AP2M1 depletion has no effect on HCV RNA replication by qRT-PCR assays. HCV RNA replication, by qRT-PCR in Huh-7.5 cells harboring the corresponding shRNAs 72 hr following electroporation with J6/JFH(p7-Rluc2A) relative to NT control. Means and s.d. (error bars) of results from two independent experiments in triplicates are shown.
Figure 13A:
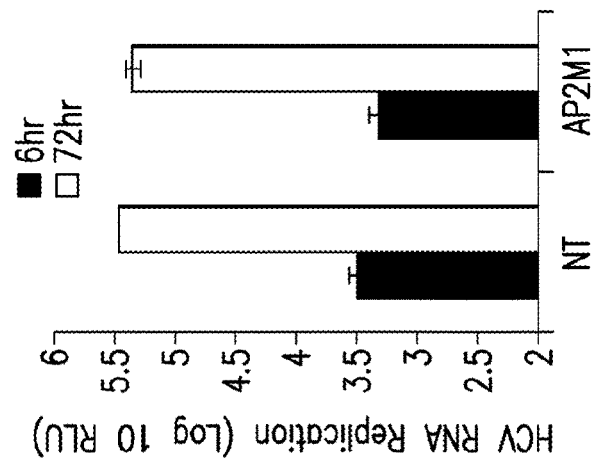
FIG. 13A-G: Shows transient depletion of AP2M1 by pooled siRNAs inhibits HCV assembly.
Figure 13B:
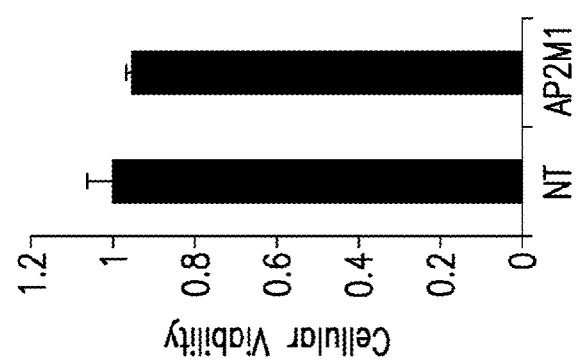
Figure 13C:
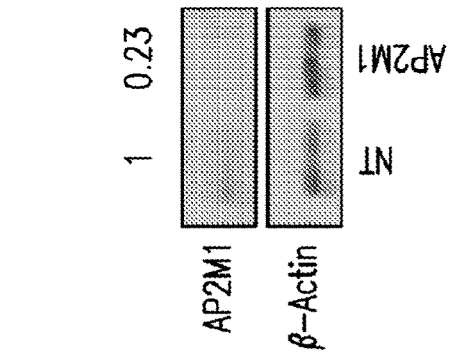
Figure 13D:
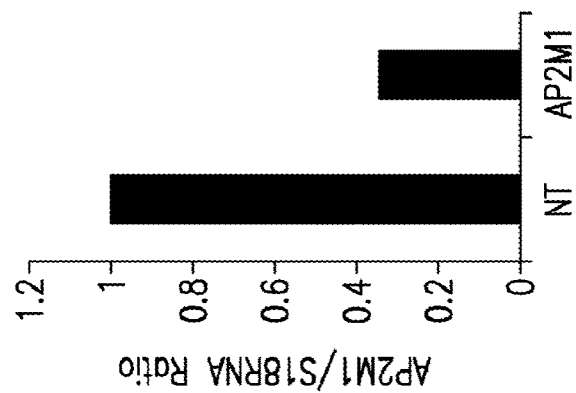
Figure 13G:
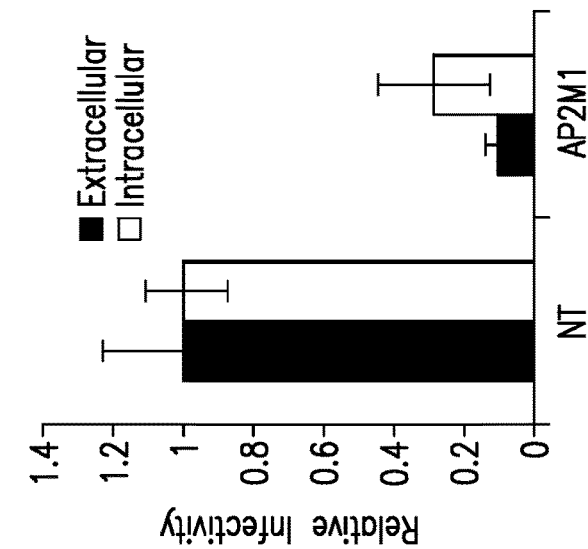
Figure 13F:
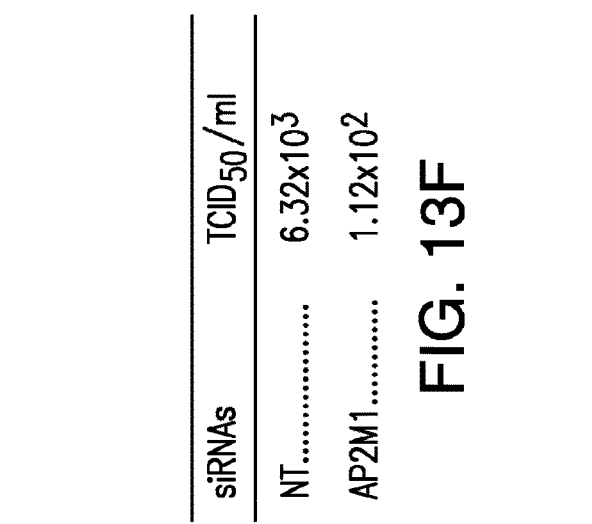
Figure 13E:
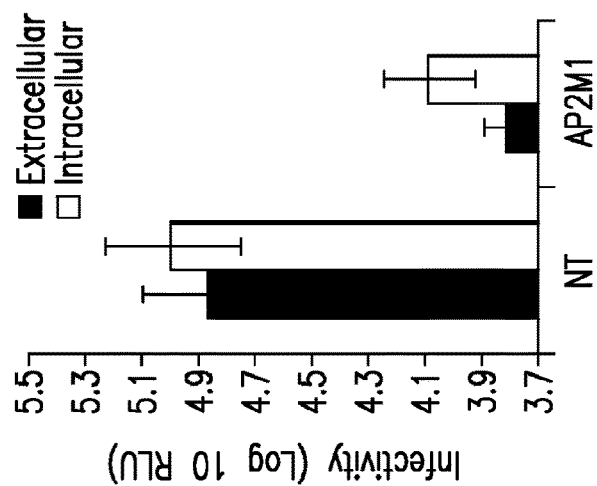

Using a series of point mutations (FIG. 1D), whether AP2M1 binding is mediated by core's YXXΦ motif was tested. A Y136A core mutation reduced AP2M1 binding measured by PCAs by ~10 fold compared with wild type (WT) core, whereas a V(Φ)139A mutation caused less inhibition of binding (FIG. 3A). To study the role of core's YXXΦ motif in HCV infection, these mutations were introduced into the J6/JFH(p7-Rluc2A) HCV genome—a *Renilla* luciferase-containing reporter virus that replicates and produces high titers of virus in Huh-7.5 cells (Murray et al., *J Virol* 81:10220-10231, 2007). Cells were electroporated with in vitro transcribed RNA generated from each construct. HCV RNA replication of these viral mutants was comparable to that of the WT virus, as measured by luciferase reporter gene-linked assays (FIG. 3B), and qRT-PCR (FIGS. 11 and 12). In contrast, a polymerase-defective mutant, J6/JFH(p7-Rluc2A)-GNN, did not replicate. Luciferase assays in naive cells inoculated with supernatants derived from cells electroporated with viral genome harboring the Y136A core mutation measured undetectable levels of extracellular infectivity. The V139A mutation decreased infectivity by ~1.5 logs compared to WT virus (FIG. 3C). Intracellular infectivity, measured in naive cells infected with clarified supernatants derived from lysed electroporated cells, mirrored the diminished extracellular infectivity (FIG. 3D), suggesting that core's YXXΦ motif mediates virions assembly and not release. Essentially no infectious virus was produced either intra- or extracellularly by assembly (ΔE1-E2) or replication (GNN) defective controls. Infectivity titers of WT virus measured by limiting dilution assays were comparable to those previously reported with this reporter system (Kopp et al., *J Virol* 84:1666-1673, 2010). Consistent with the luciferase assays described above, while the V139A core mutation decreased the extra- and intracellular infectivity titers by a ~1-1.5 log compared with WT virus, an undetectable level of infectivity titers was measured with virus harboring the Y136A core mutation or E1-E2 deletion (FIG. 3E). The effect of core mutations on infectivity correlated with their effect on AP2M1 binding. To exclude the possibility that core's mutations affected infectivity by causing particle disassembly or production of defective core protein- and RNA-containing particles, production of noninfectious particles was determined. Detectable levels of HCV RNA and core protein release were measured in supernatants of cells harboring replicating genomes by qRT-PCR and ELISA assays, respectively, as described (Murray et al., *J Virol* 81:10220-10231, 2007; Kopp *J Virol* 84:1666-1673, 2010) (FIG. 3F, 3G). Nevertheless, the levels released by the Y136A and V139A core mutants were not significantly higher than those released by the assembly-defective ΔE1-E2 mutant, suggesting that noninfectious particles were not produced. Core expression was not affected by the mutations, as western analysis (FIG. 3H) and fluorescence microscopy (data is not shown) demonstrated protein expression at WT levels. Reversion of the infectivity phenotype was detected by luciferase assays in Huh-7.5 cells infected with HCV harboring the Y136A and V139A core mutations following two weeks of passaging. This reversion coincided with the emergence of primary-site revertants by sequencing analysis. These results provide additional evidence for the requirement of maintaining a functional YXXΦ motif for supporting HCV replication. Together, these data suggest that the AP2M1 binding motif within core is required for viral assembly in vitro.

Core's YXXΦ Motif is Functionally Interchangeable with Other YXXΦ Sorting Signals To determine whether core's YXXΦ motif is functionally interchangeable with homologous signals, a V139L mutation, thus "swapping" the genotype 2a core's sequence with that of genotype 1b was introduced. Similarly, the YTPL and YRRL sequences, known to mediate binding of HLA-DM (Ohno et al., *J Bioll Chem* 273:25915-25921, 1998) and thrombopoietin receptor (Hitchcock et al., *Blood* 112:2222-2231, 2008) to AP2M1, respectively, were used to substitute the core's YXXΦ sequence (FIG. 1D). Binding of core harboring these sequences to AP2M1 was either comparable to or greater than that of WT core, as determined by PCAs (FIG. 3A). These mutations had no effect on HCV RNA replication (FIG. 3B). In correlation with their biochemical phenotype, the intracellular and extracellular infectivity of the V139L and YTPL core mutants were comparable to that of WT virus (FIG. 3C, 3D). This functional interchangeability supports that core's YXXΦ motifs exerts its function via interactions with host cell proteins. Despite its efficient binding to AP2M1 (FIG. 3A) and stability by western analysis (FIG. 3H), the YRRL mutant did not produce detectable levels of infectious virus (FIG. 3C, 3D). Interestingly, this mutant released HCV RNA and core protein into supernatants of electroporated cells at levels comparable to that of WT core, likely reflecting production of noninfectious particles (FIG. 3F, 3G). The YRRL mutant may thus impact other function of core in infectious virus production that is independent of its binding to AP2M1.

AP2M1 in HCV Assembly

Figure 4C:
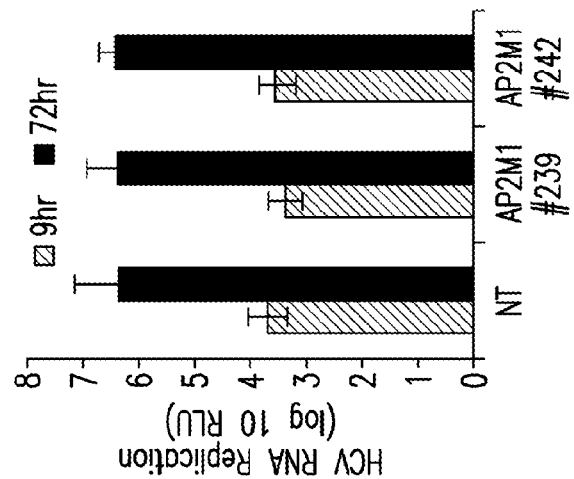
Figure 4B:
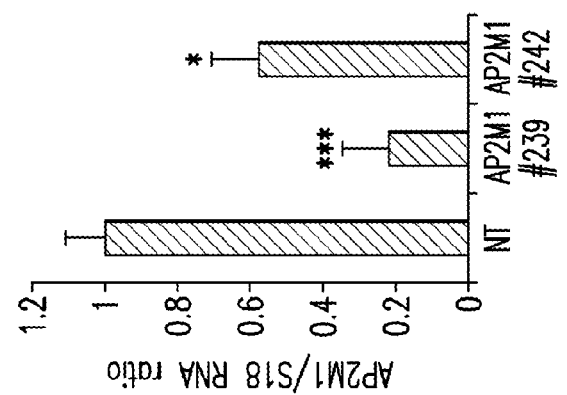
Figure 4A:
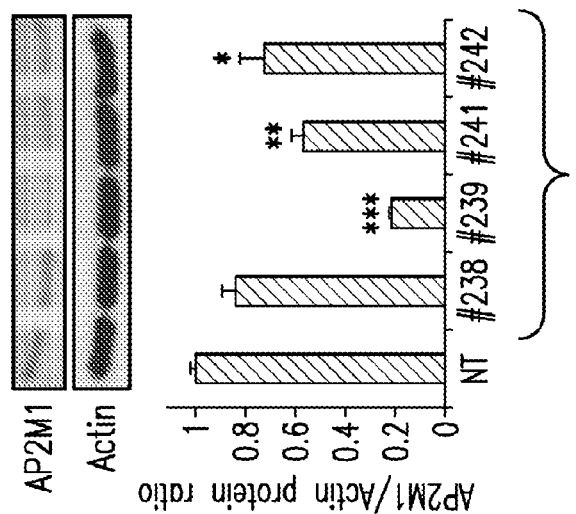
Figure 4I:
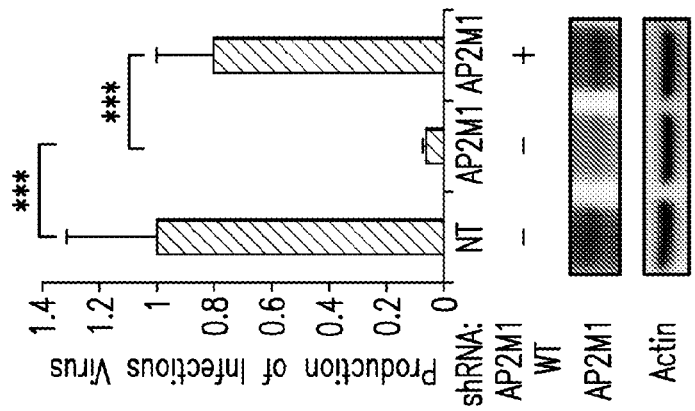
Figure 4H:
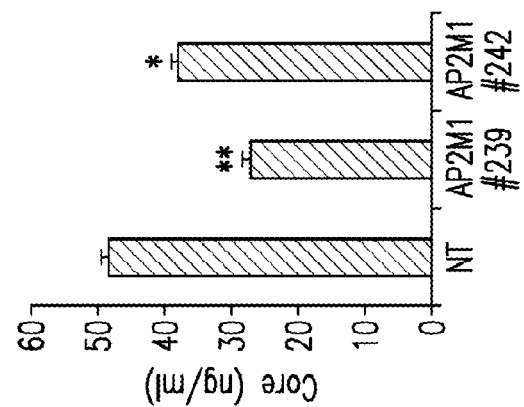
Figure 4G:
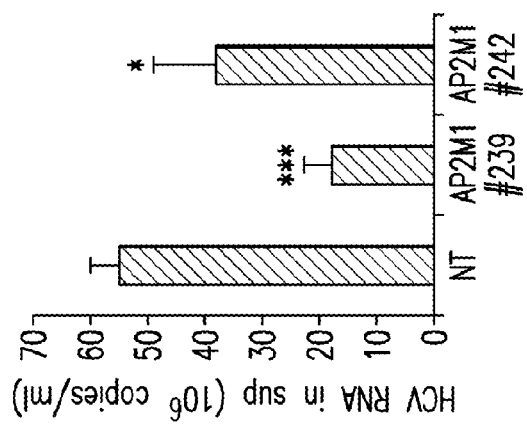

The functional relevance of AP2M1 to the HCV life cycle was determined. Stable Huh-7.5 clones harboring short hairpin RNA (shRNA) lentiviral constructs targeting distinct regions in the AP2M1 gene or a non-targeting (NT) sequence were established. Effective suppression of AP2M1 levels was achieved (FIG. 4A, 4B), without apparent cytostatic or cytotoxic effects. The effect of AP2M1 depletion on infectious virus production was studied in these clones following electroporation with J6/JFH(p7-Rluc2A) RNA. AP2M1 knockdown had no effect on HCV RNA replication as measured in these stable clones by luciferase assays (FIG. 4C) and qRT-PCR 72 hr following electroporation (data not shown). Supernatants collected at 72 hr postelectroporation were used to inoculate naive Huh-7.5 cells followed by luciferase assays at 72 hr postinoculation. As shown in FIG. 4D, AP2M1 depletion reduced extracellular infectivity by >2 logs compared with NT control. Intracellular infectivity, measured in naive cells infected with clarified supernatants derived from lysed electroporated cells, mirrored the diminished extracellular infectivity(FIG. 4E) and correlated with the degree of AP2M1 depletion. Measurements of intra- or extracellular infectivity titers by limiting dilution assays demonstrated consistent results (FIG. 4F). AP2M1 depletion did not increase production of noninfectious particles, as suggested by the levels of HCV RNA and core protein release measured in supernatants of cells by qRT- PCR and ELISA assays, respectively (FIG. 4G, 4H). Similar effects on infectious virus production were demonstrated in Huh-7.5 cells transiently depleted for AP2M1 by siRNAs and either electroporated with the J6/JFH(p7-Rluc2A) RNA or infected with culture grown J6/JFH virus (titer: $1.2 \times 10^5$ TCID$_{50}$/ml) (Lindenbach et al., *Science* 309:623-626, 2005). The effects of silencing endogenous AP2M1 on infectious virus production were rescued by ectopic expression of shRNA-resistant WT AP2M1 harboring a wobble mutation within the site targeted by the shRNA, largely excluding the possibility of off-target effects causing the observed phenotype (FIG. 4I). The stable and transient RNAi approaches thus both suggest that AP2M1 is important for efficient HCV assembly.

Disruption of Core-AP2M1 Binding Abolishes Recruitment of AP2M1 to LD, Alters the Sub-Cellular Localization of Core, and Core Colocalization with E2

Figure 5A:
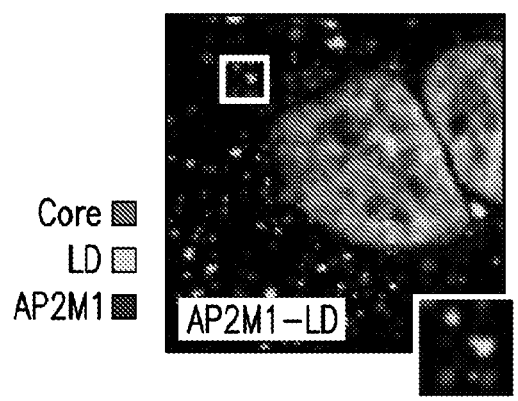
FIG. 5A-P: Shows that disruption of core-AP2M1 binding abolishes recruitment of AP2M1 to LD and alters the sub-cellular localization of core and its colocalization with E2. Quantitative confocal immunofluorescence (IF) analysis of the sub-cellular localization of core and AP2M1 and core-E2 colocalization in Huh-7.5 cells.
Figure 5B:
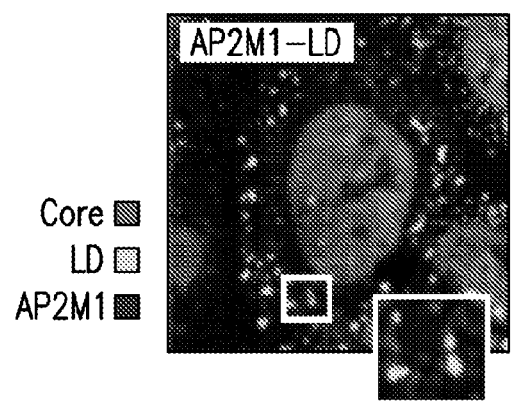
FIG. 5(B)-(D) Merged images of Huh-7.5 cells infected with J6/JFH HCV stained for core (red), the LD marker, Bodipy (green), and AP2M1 (blue).
Figure 5C:
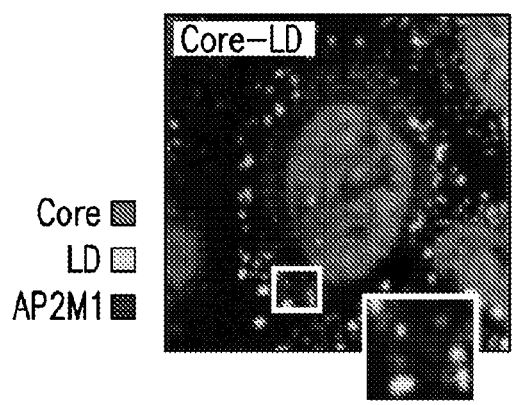
Figure 5D:
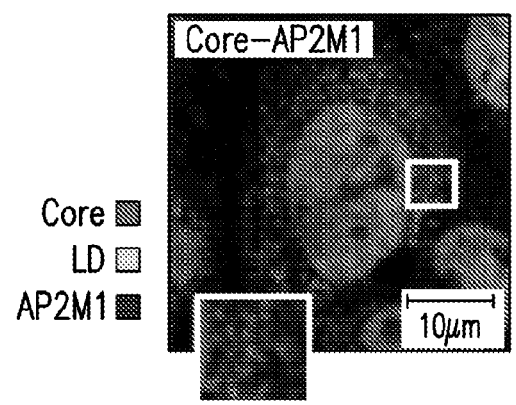
Figure 5E:
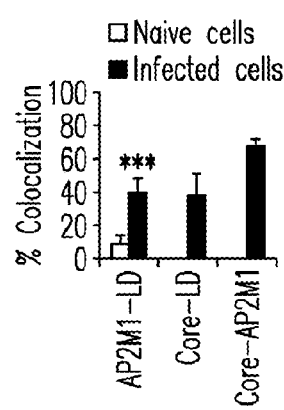
FIG. 5(E) Percent colocalization of the indicated signals in naive (white) or infected (black) cells by a quantitative colocalization analysis of (A)-(D).
Figure 5F:
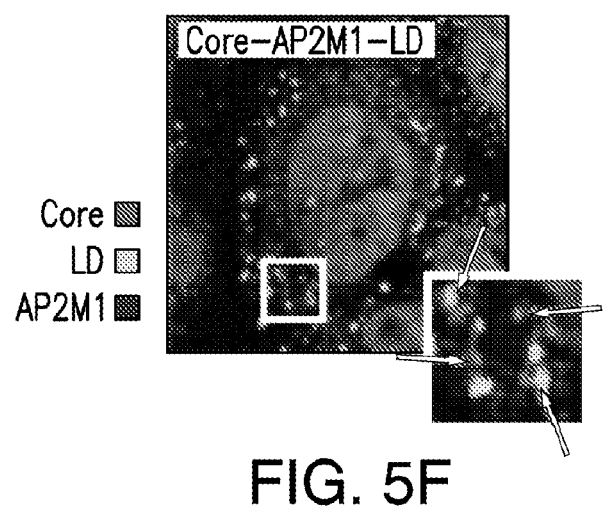
FIG. 5(F) A four channel merged image. The yellow arrows in the inset indicate colocalization of core and AP2M1 to LD.

To test the hypothesis that the defect in HCV assembly resulting from YXXΦ core mutations or AP2M1 silencing correlates with alterations in the sub-cellular localization of AP2M1 and/or core, a quantitative confocal immunofluorescence (IF) analysis was performed. 10-15 randomly chosen cells were analyzed for each category for the degree of localization of core or AP2M1 to various intracellular compartments using ImageJ (JACoP) software and Manders' Colocalization Coefficients (MCC). The latter were chosen, as they strictly measure co-occurrence independent of signal proportionality (Dunn et al., *Am J Physiol-Cell Physiol* 300:C723-C742, 2011). Endogenous AP2M1 minimally colocalized with the LD marker, Bodipy, in naive Huh-7.5 cells, with 8.2% of LD staining positive for AP2M1 (FIG. 5A, 5E). In contrast, infection with J6/JFH virus appeared to significantly increase the localization of AP2M1 to LD, with 40±8% of LD being AP2M1 positive (FIG. 5B, 5E) (p-value=0.0006). Similarly, and as previously described (Kopp et al., *J. Virol.* 84:1666-1673, 2010; Boulant et al., *Journal of General Virology* 88:2204-2213, 2007; Coller et al., *PLoS pathogens* 8:e1002466-e1002466, 2012), core was partially localized to LD (37±14% of core positive LD) (FIG. 5C, 5E). Furthermore, the partial colocalization of core with AP2M1 occurred in part on LD (FIG. 5D, 5F).

Figure 5G:
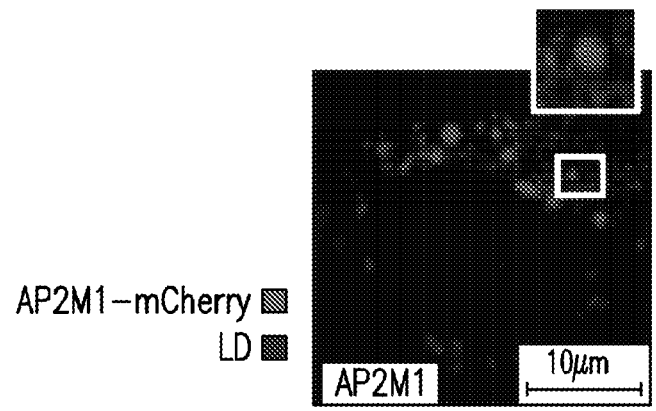
FIG. 5(G)-(J) Representative merged images and quantitative colocalization analysis of AP2M1 (red) and the lipid marker, LipidTOX (blue), in Huh-7.5 cells transfected with plasmids expressing AP2M1-mCherry alone FIG. 5(G) or AP2M1-mCherry with WT core FIG. 5(H) or core Y136A mutant FIG. 5(I). Core expression (green) in the cells shown in panels FIG. 5(H)
Figure 5H:
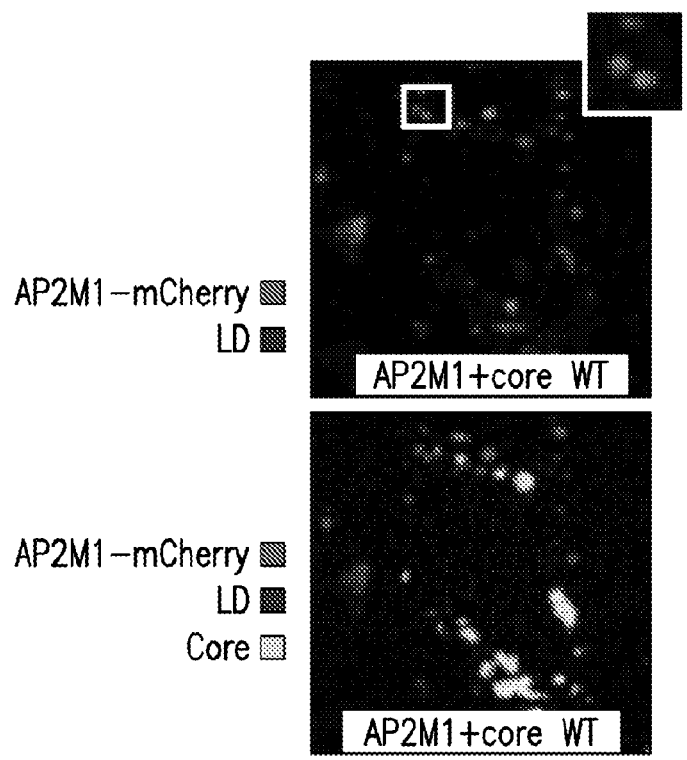
Figure 5I:
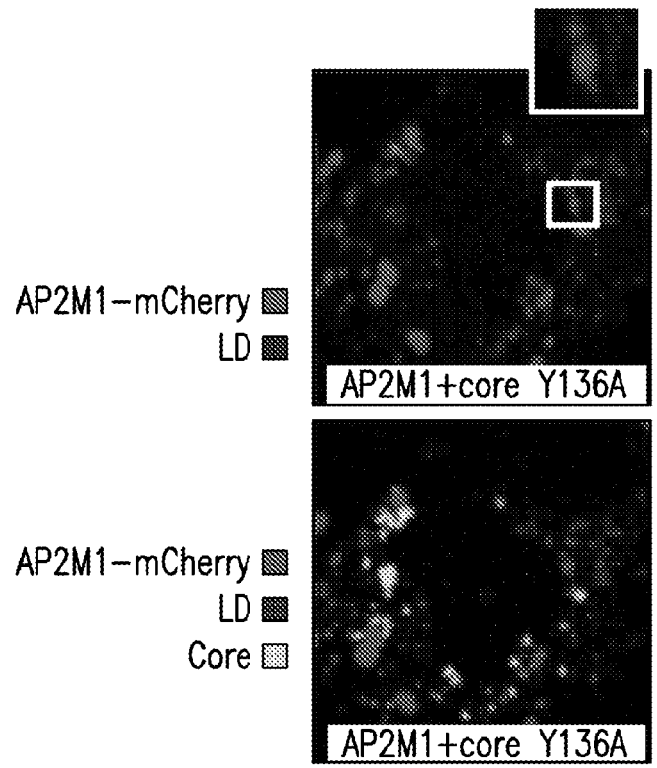
Figure 5J:
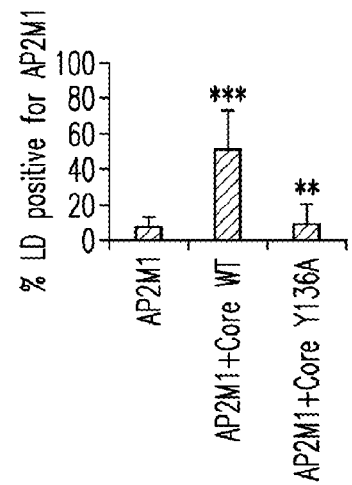

To test whether core is involved in mediating the increased localization of AP2M1 to LD measured in HCV infected cells, AP2M1-mCherry was overexpressed either alone or in combination with WT core or Y136A core mutant by transfecting Huh-7.5 cells. LD were labeled with HCS LipidTOX (Invitrogen). Similarly to naive cells, AP2M1 was minimally localized to LD in Huh-7.5 cells overexpressing AP2M1 alone (8±2% of LD positive for AP2M1) (FIG. 5G, 5J). In contrast, as in infected cells, when co-expressed with WT core, AP2M1 appeared to significantly accumulate at LD, with 51.8±20% of LD being AP2M1 positive (p-value=$4.8 \times 10^{-5}$) (FIG. 5H, 5J). No such increase in colocalization was demonstrated, however, when AP2M1 was co-expressed with core harboring the Y136A mutation (with 10% AP2M1 positive LD) (p-value=0.001) (FIG. 5I, 5J), suggesting that core's YXXΦ motif may mediate recruitment of AP2M1 to LD.

Figure 5K:
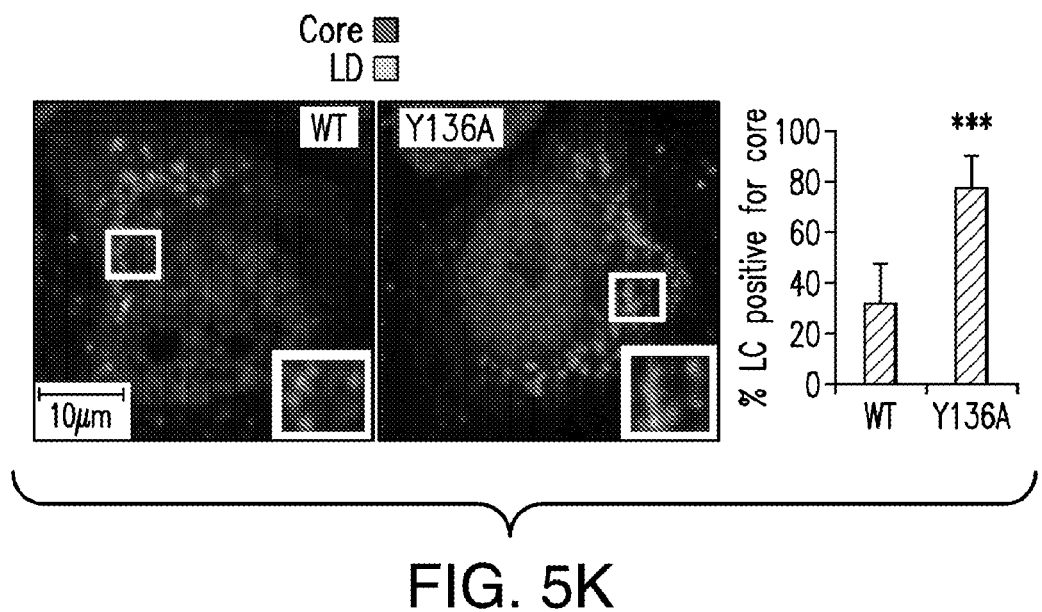
Figure 5L:
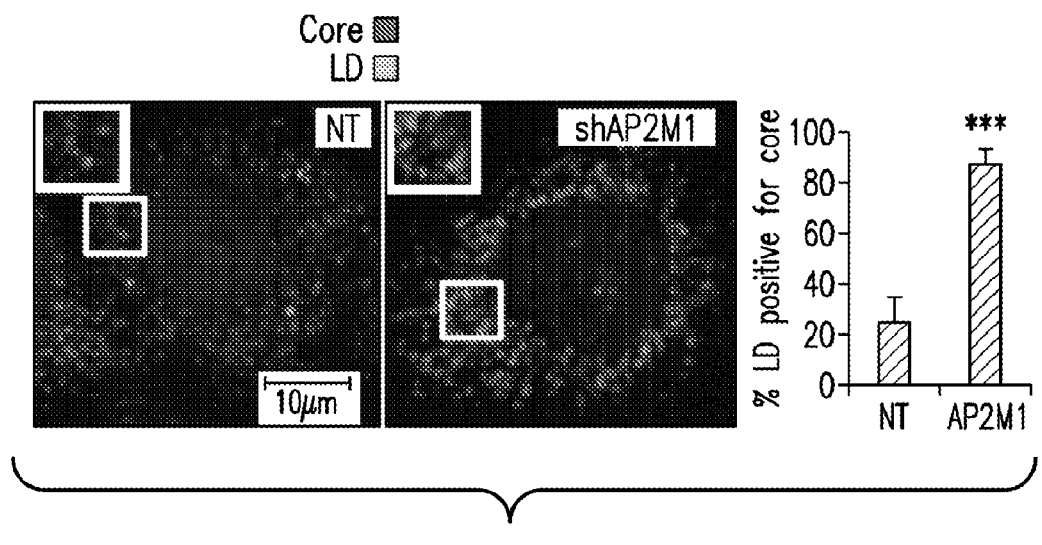
Figure 5M:
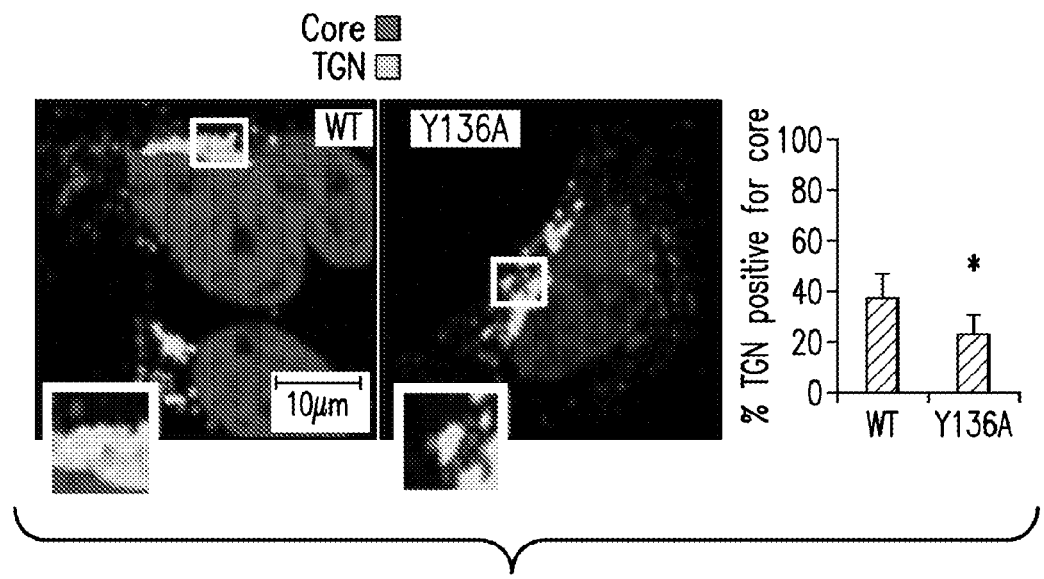
Figure 5N:
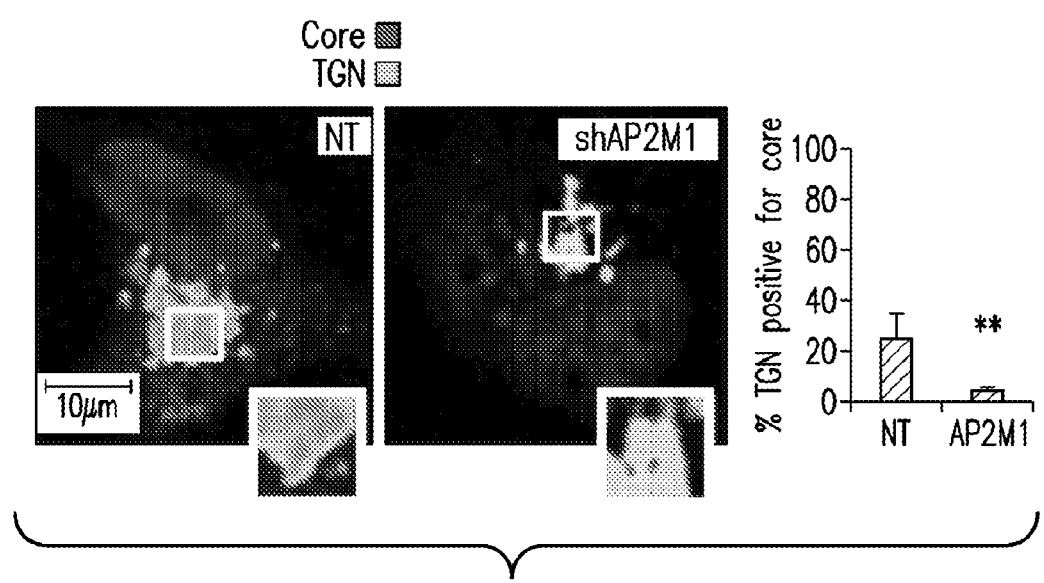
Figure 5O:
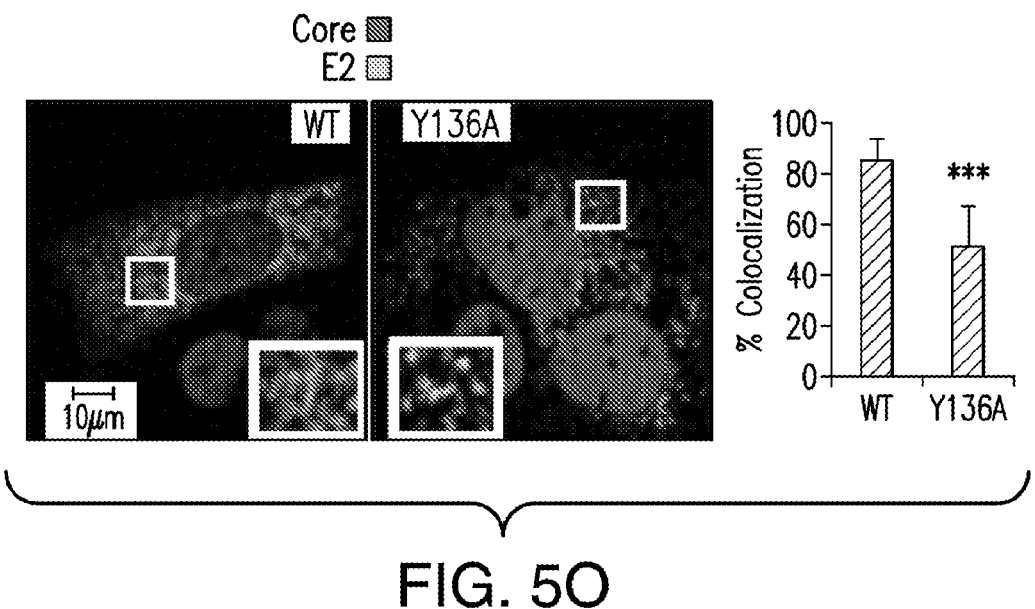
Figure 5P:
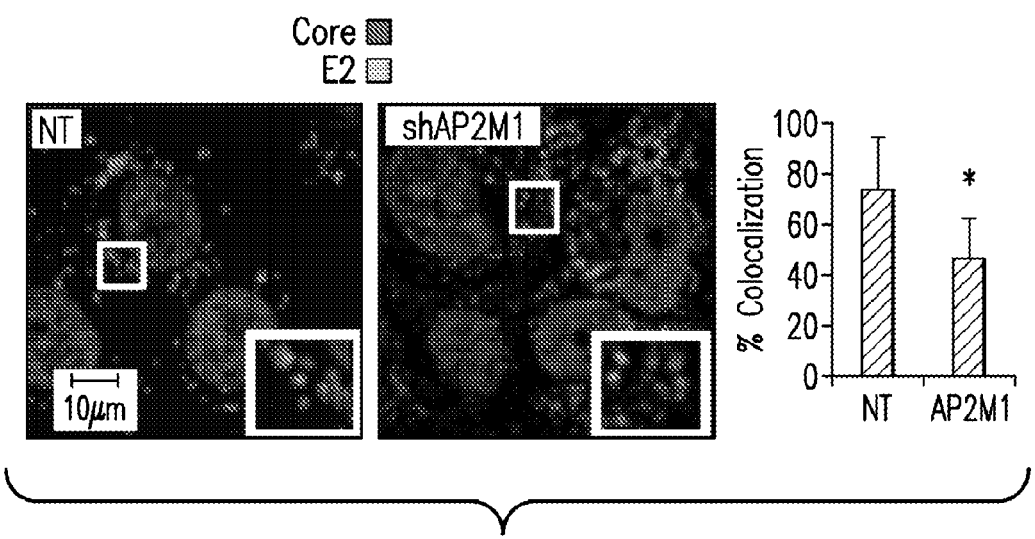
Figure 14A:
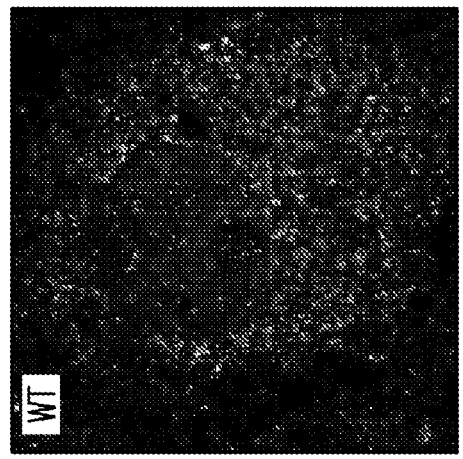
FIG. 14A-C: Shows that a Y136A core mutation does not seem to affect core localization to ER membranes in HCV infected cells.
Figure 14B:
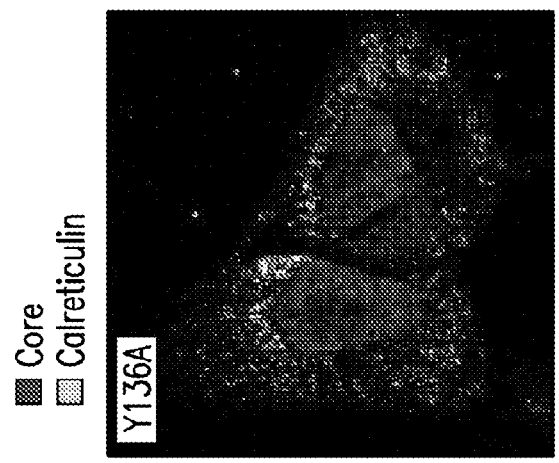
Figure 14C:
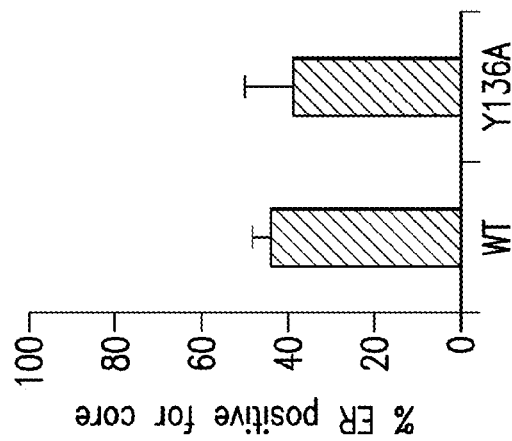

The effect of disruption of the core-AP2M1 interaction on core localization to LD, ER, and TGN and its colocalization with the E2 envelope protein in cells electroporated with J6/JFH HCV RNA was tested. As previously shown, core localized to all these intracellular compartments (Kopp et al., *J. Virol.* 84, 1666-1673, 2010; Boulant et al., *Journal of General Virology* 88, 2204-2213, 2007) (with percent colocalization ranging from 30 to 45%). Interestingly, localization of core harboring the Y136A mutation to LD was significantly greater than that of WT core (78±13% vs. 32±16%, respectively, p-value=$2.7 \times 10^{-6}$) (FIG. 5K). Similarly, the percent colocalization of core with the LD marker was dramatically increased from 25±10% in NT cells to 87±6.6% following silencing of AP2M1 (p-value=$1.55 \times 10^{-8}$) (FIG. 5L). While neither the Y136A core mutation nor AP2M1 depletion had an apparent effect on core colocalization with the ER marker, calreticulin (FIG. 14), both were associated with a significant decrease in core colocalization with the TGN marker, TGN46 (FIG. 5M, 5N) and the E2 envelope protein (FIG. 5O, 5P).

Together, these results suggest that core's interaction with AP2M1 facilitates recruitment of AP2M1 to LD and that the observed defect in HCV assembly following disruption of the core-AP2M1 interaction is associated with accumulation of core on LD, decreased core colocalization with E2, and impaired core trafficking to TGN.

AAK1 and GAK Regulate Core-AP2M1 Binding and are Involved in HCV Assembly

Figure 6B:
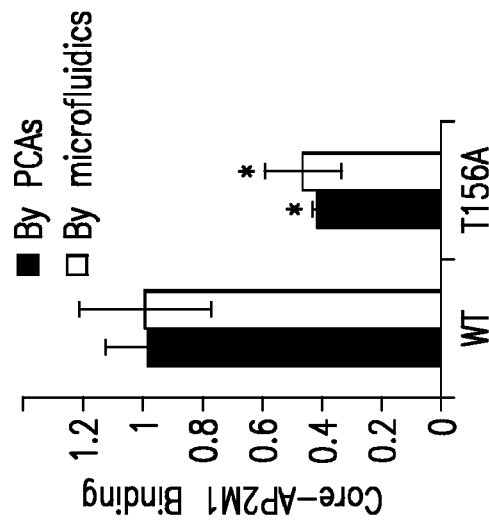
Figure 6D:
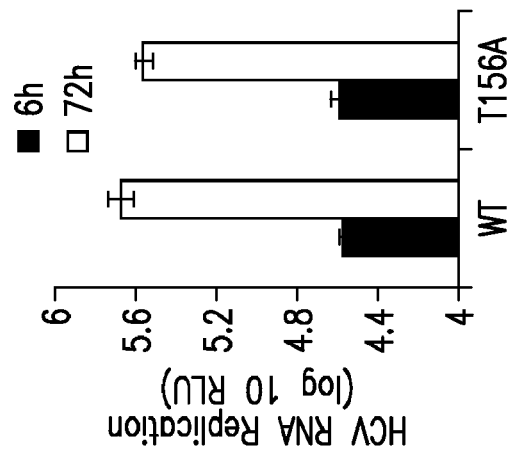
Figure 6A:
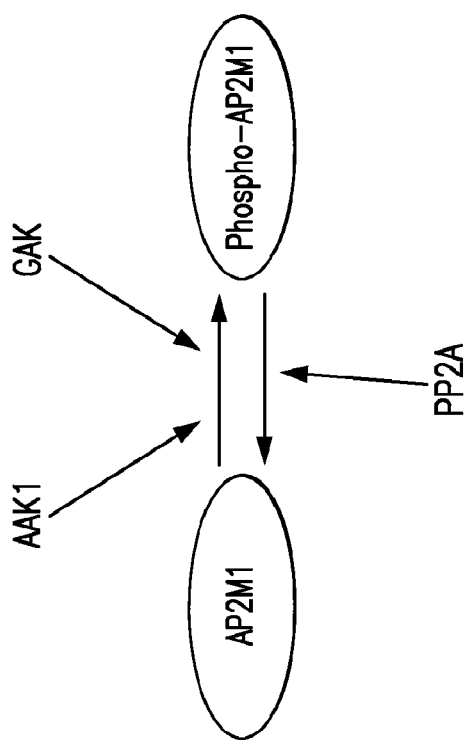
Figure 6C:
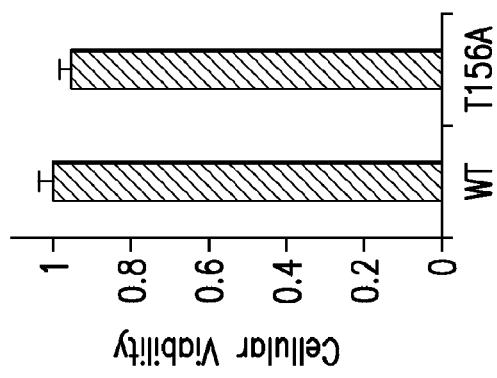

Phosphorylation of T156 within AP2M1 by the serine/threonine kinases AAK1 and GAK (Ricotta et al., *Journal of Cell Biology* 156, 791-795, 2002; Korolchuk et al., *Traffic* 3, 428-439, 2002; Zhang et al., *Traffic* 6, 1103-1113, 2005) stimulates binding of AP2M1 to cargo protein tyrosine signals and is transient due to dephosphorylation by PP2A (Ricotta et al., *Journal of Biological Chemistry* 283, 5510-5517, 2008) (FIG. 6A). Indeed, calyculin A (a PP2A inhibitor) augmented the binding of core to AP2M1 (FIG. 2D) and a T156A AP2M1 mutation impaired it (FIG. 6B). To study the effect of overexpression of AP2M1 harboring the T156A mutation on infectious HCV production, Huh-7.5 cells were transfected with plasmids encoding either WT or AP2M1 T156A mutant. 48 hr posttransfection cells were electroporated with J6/JFH(p7-Rluc2A) HCV RNA and subjected to HCV RNA replication and infectivity assays, as described above. Overexpression of the T156A AP2M1 mutant had no effect on cellular viability and was dispensable for HCV RNA replication, yet significantly reduced extra- and intra-cellular infectivity compared with WT AP2M1 (FIG. 6C-E), consistent with a dominant negative effect on HCV assembly.

Figure 6I:
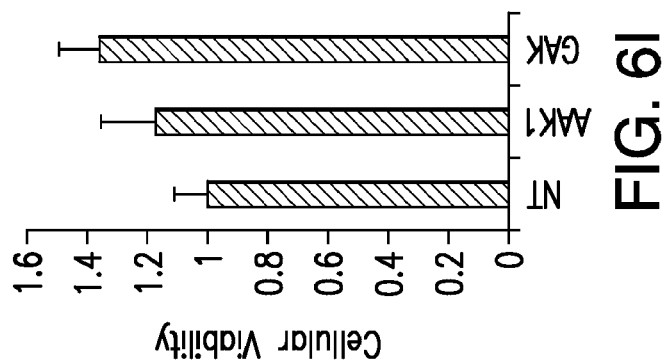
Figure 6J:
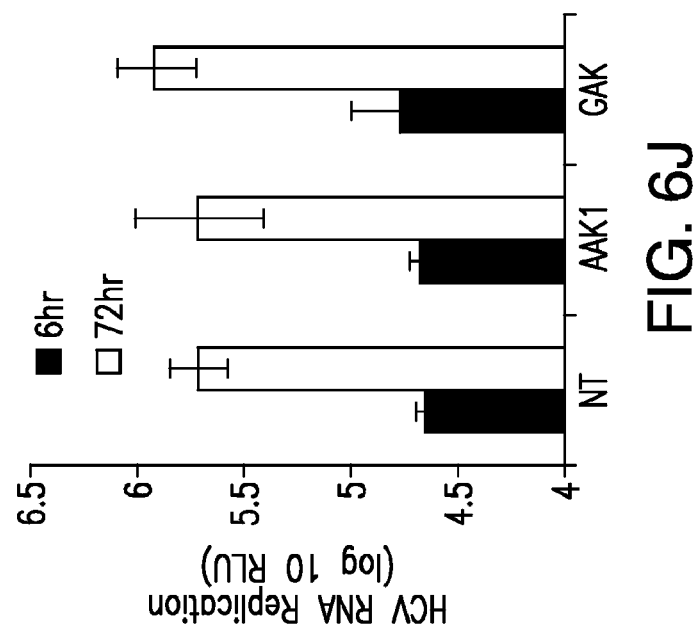
Figure 6H:
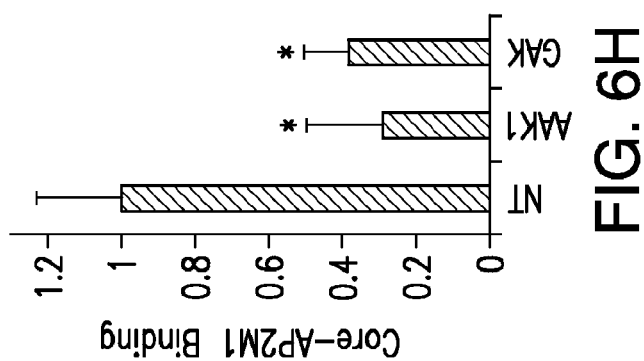
Figure 6L:
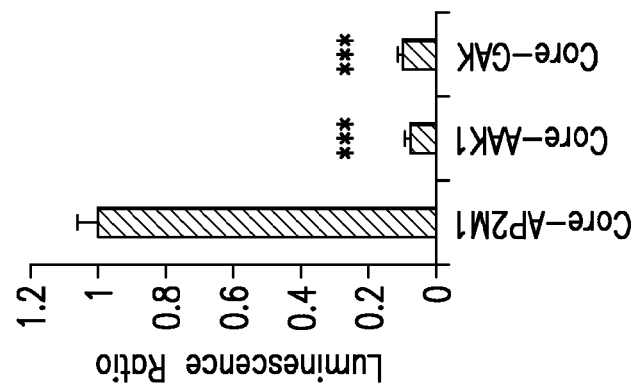
Figure 6K:
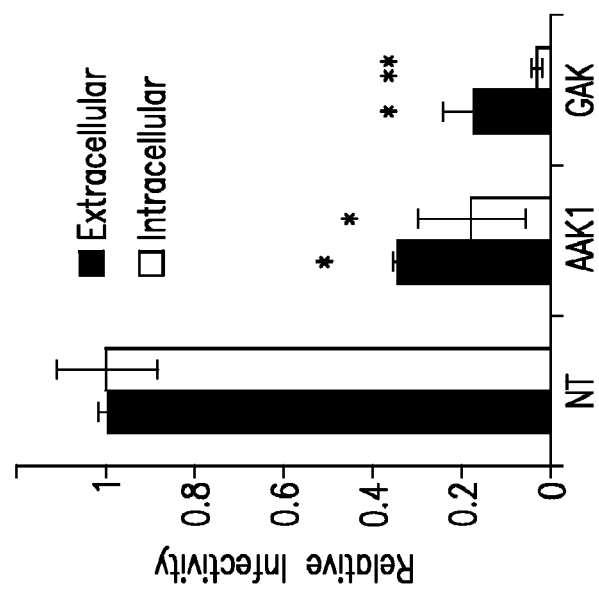

To study the hypothesis that AAK1 and GAK are involved in regulating the interaction of AP2M1 with core, binding experiments were performed in Huh-7.5 cells depleted for AAK1 or GAK by siRNAs (FIG. 6F, 6G). Depletion of either AAK1 or GAK significantly decreased core-AP2M1 binding compared to NT, as measured by PCAs (FIG. 6H), with no apparent cytotoxic effect (data not shown). AAK1 and GAK depleted cells were then electroporated with J6/JFH(p7-Rluc2A) HCV RNA. While depletion of either AAK1 or GAK had no cytotoxic effect and was dispensable for HCV RNA replication, it significantly reduced intracellular and extracellular infectivity (FIG. 6I-K). The effect of AAK1 and GAK on HCV assembly did not result from their direct binding to core (FIG. 6L). These results provide evidence for the involvement of AAK1 and GAK in the regulation of core-AP2M1 binding and in mediating HCV assembly. Moreover, they validate the importance of AP2M1 for efficient HCV assembly by a dominant-interfering approach, thus supporting the RNAi data.

Figures 7A, 7B:
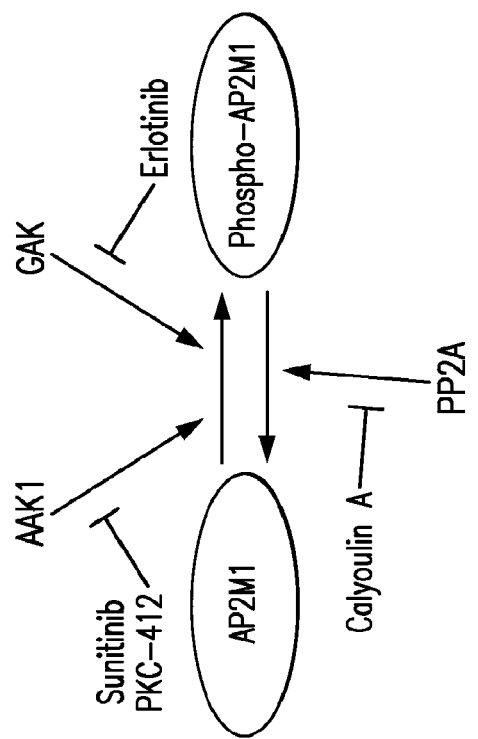
Figure 7F:
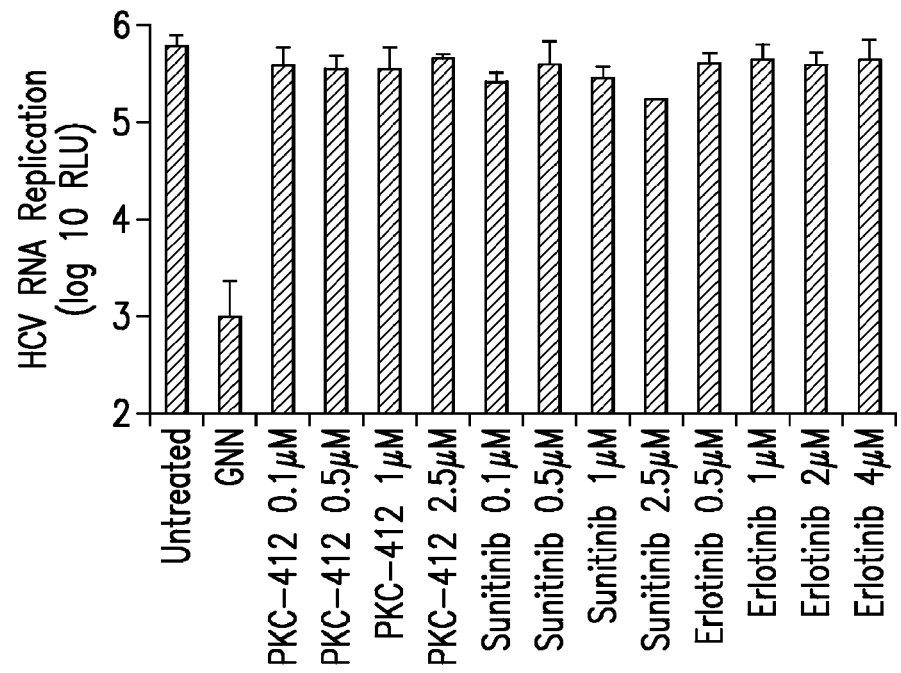
Figure 7G:
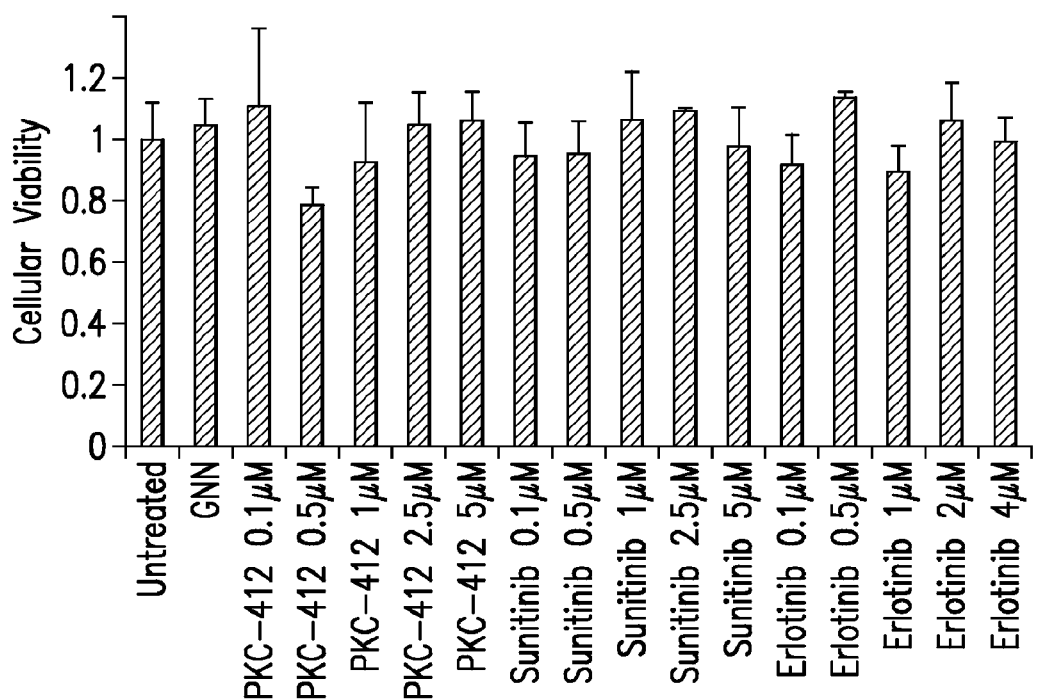
Figure 7H:
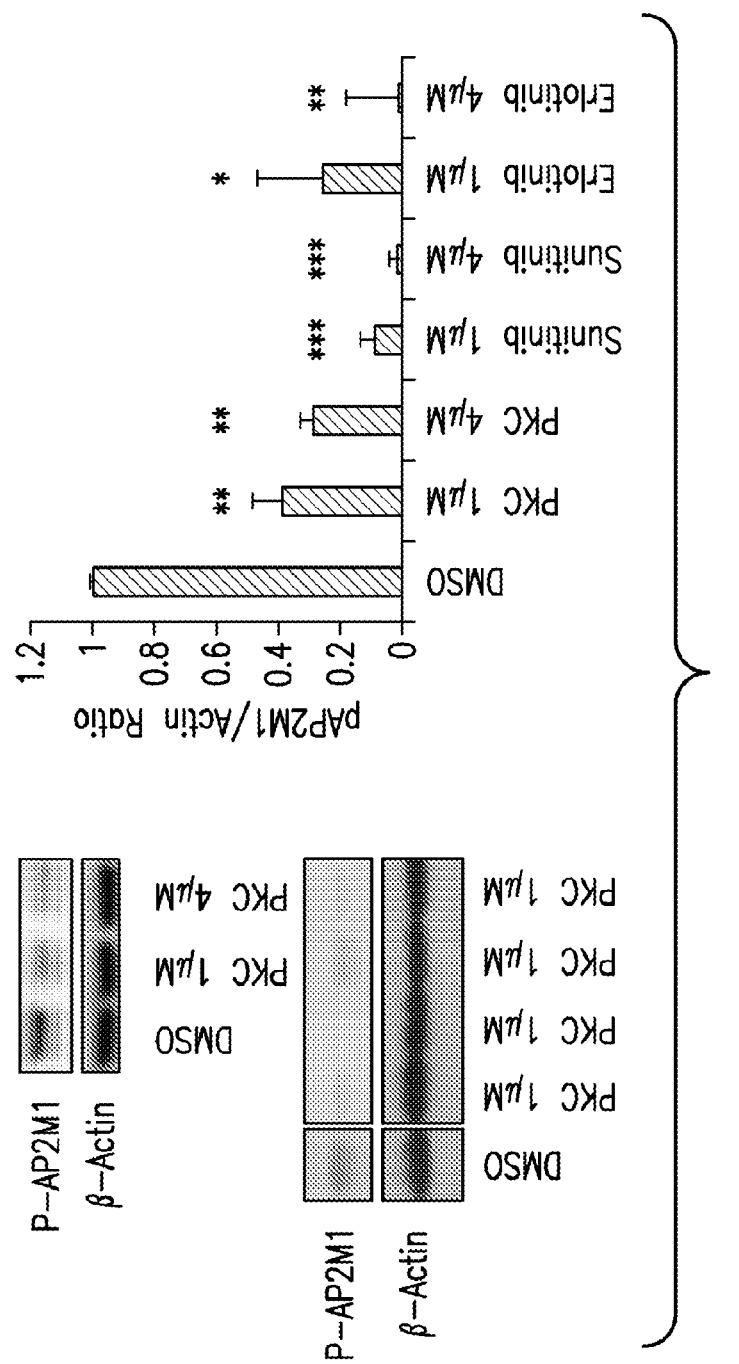
Figure 7I:
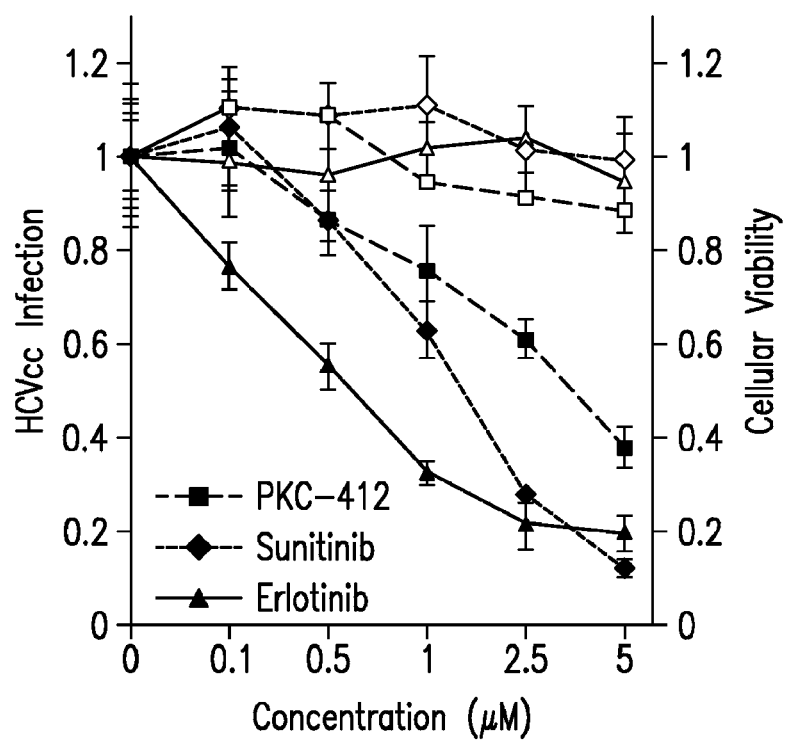
Figure 8A:
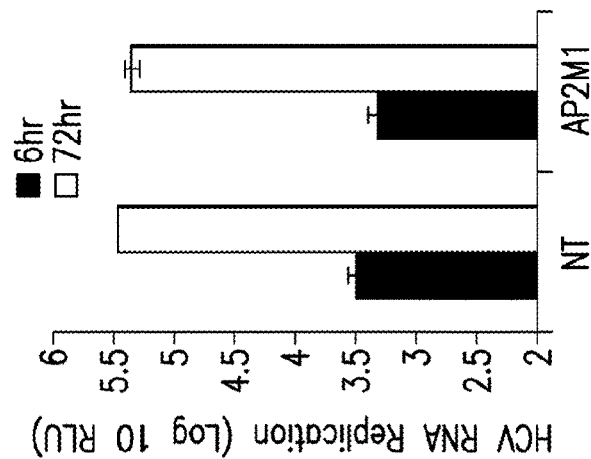
FIG. 8A-G: Transient depletion of AP2M1 by pooled siRNAs inhibits HCV assembly.
Figure 8B:
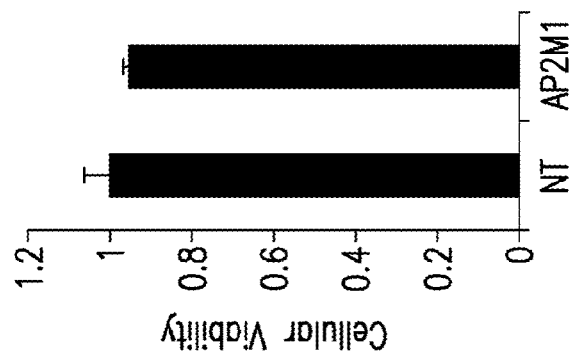
Figure 8C:
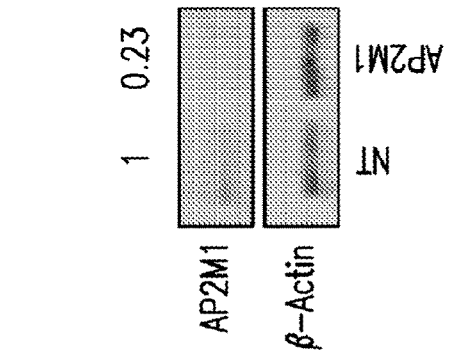
Figure 8D:
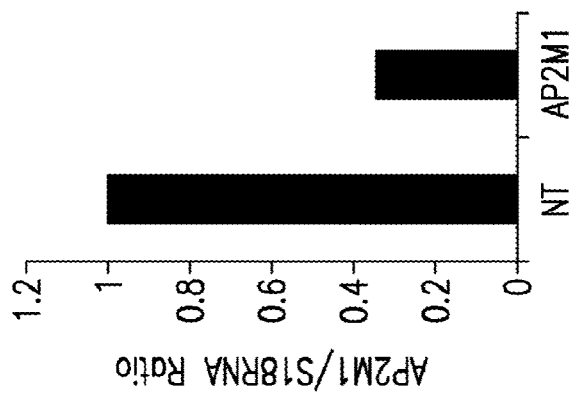
Figure 8G:
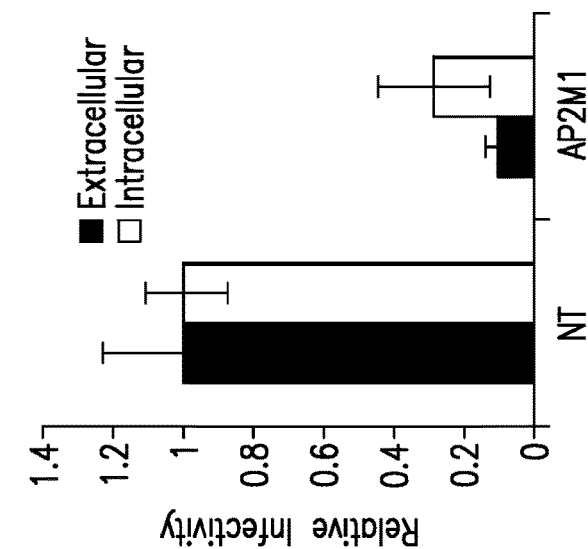
Figure 8F:
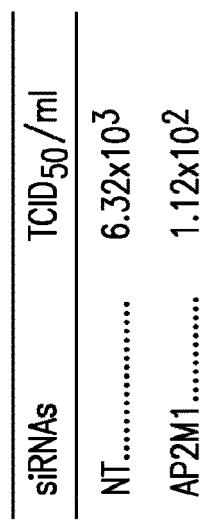
Figure 8E:
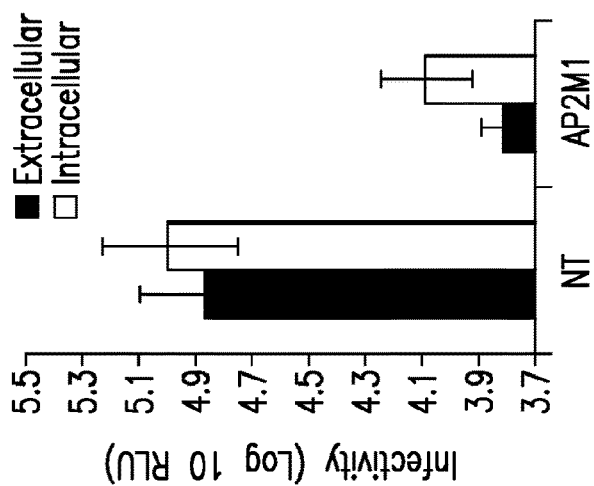

Pharmacological Inhibitors of AAK1 and GAK Disrupt Core-AP2M1 binding and HCV assembly Analysis of heat maps and affinity assays of kinase inhibitors (Karaman et al., *Nat Biotech* 26, 127-132, 2008) revealed compounds, such as sunitinib and PKC-412, which bind AAK1, and erlotinib which binds GAK, with high affinities (nM range) (Karaman et al., *Nat Biotech* 26, 127-132, 2008) (FIG. 7A, 7B). These compounds inhibited core-AP2M1 binding in a dose-dependent manner, as determined by PCAs (FIG. 7C), with half maximal inhibitory concentrations (IC50s) of ~0.04-0.2 µM. When used to treat Huh-7.5 cells electroporated with the J6/JFH(p7-Rluc2A) HCV genome, these compounds had a dramatic dose-dependent effect on extra—(FIG. 7D) and intracellular infectivity (FIG. 7E) at 72 hr (with half maximal effective concentration (EC50s) of 0.15-1.8 µM) (FIG. 7B). There was no effect on HCV RNA replication and no apparent cellular toxicity (FIG. 7F, 7G). Indeed, the inhibitory effect on core-AP2M1 binding and infectivity was associated with reductions in phospho-AP2M1 levels in the relevant cells by western analysis (FIG. 7H,). Last, these compounds significantly inhibited viral infection in Huh-7.5 cells infected with tissue culture grown HCV (titer: 6.3×10$^5$ TCID$_{50}$/ml ) (FIG. 7I, 7B,). These results provide pharmacological validation for the involvement of AAK1 and GAK in regulating the core-AP2M1 interaction and for AP2M1's role in HCV assembly. Furthermore, they provide candidate compounds targeting assembly.

Example 2

AAK1 and GAK Depletion or Pharmacological Inhibition Abrogate HIV-1 Replication

There is a substantial body of evidence to support that interactions of AP1M1 and AP2M1 with HIV Gag and Env (gp41) mediate several critical steps along the assembly/release pathway (Batonick et al., *Virology* 342:190-200, 2005; Camus et al., *Molec Biol Cell* 18:3193-3203, 2007; Berlioz-Torrent et al., *J Virol* 73:1350-1361, 1999; Byland et al., *Molec Biol Cell* 18:414-425, 2007; Wyss et al., *J Virol* 75:2982-2992, 2001; Ohno et al., *Virology* 238:305-315, 1997; Boge et al., *J Biol Chem* 273:15773-15778, 1998; Egan et al., *J Virol* 70:6547-6556, 1996; Rowell et al., *J Immunol* 155:473-488, 1995; Lodge et al., *EMBO J* 16:695-705, 1997; Deschambeault et al., *J Virol* 73:5010-5017, 1999). Most importantly, a tyrosine motif within Env mediates cell-to-cell spread (Gminard et al., *Traffic* 5, 181-193, 2004; Lindenbach et al., *Science* 309, 623-626, 2005), a mechanism thought to account for ongoing HIV replication despite ART (Sigal et al., *Nature* 477, 95-98, 2011), possibly via AP1M1 which sorts to basolateral membranes. However, the role of AAK1 and GAK in HIV infection has not been studied, and these mechanisms have not been targeted pharmacologically.

Figure 10A:
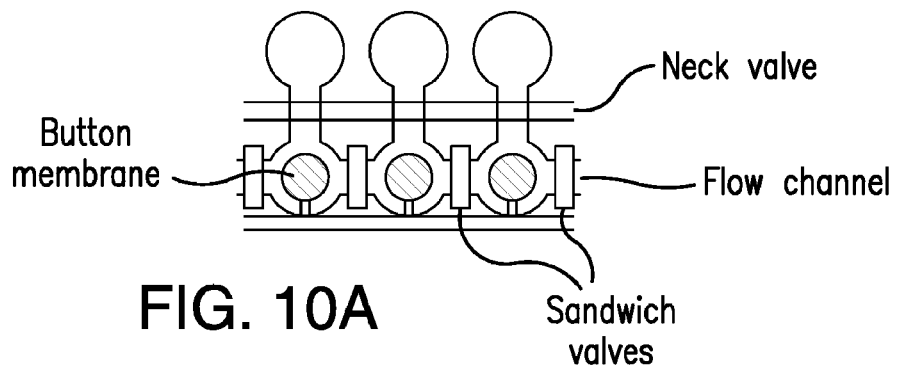
FIG. 10A-C: Shows Microfluidic-based protein-protein binding assay. Three individual unit cells (out of hundreds in a microfluidic device) are shown in this scheme.
Figure 10B:
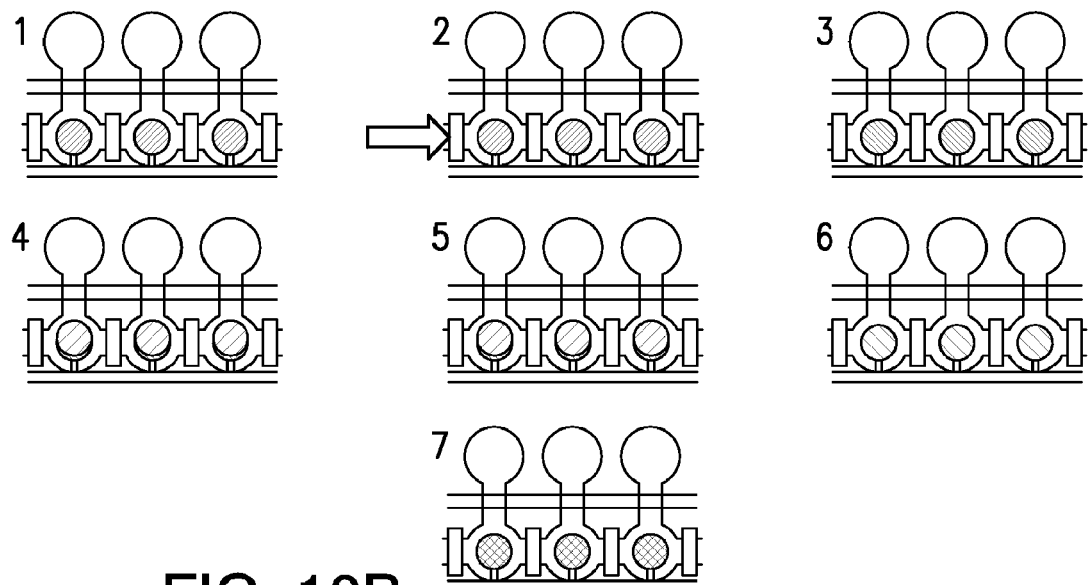
Figure 10C:
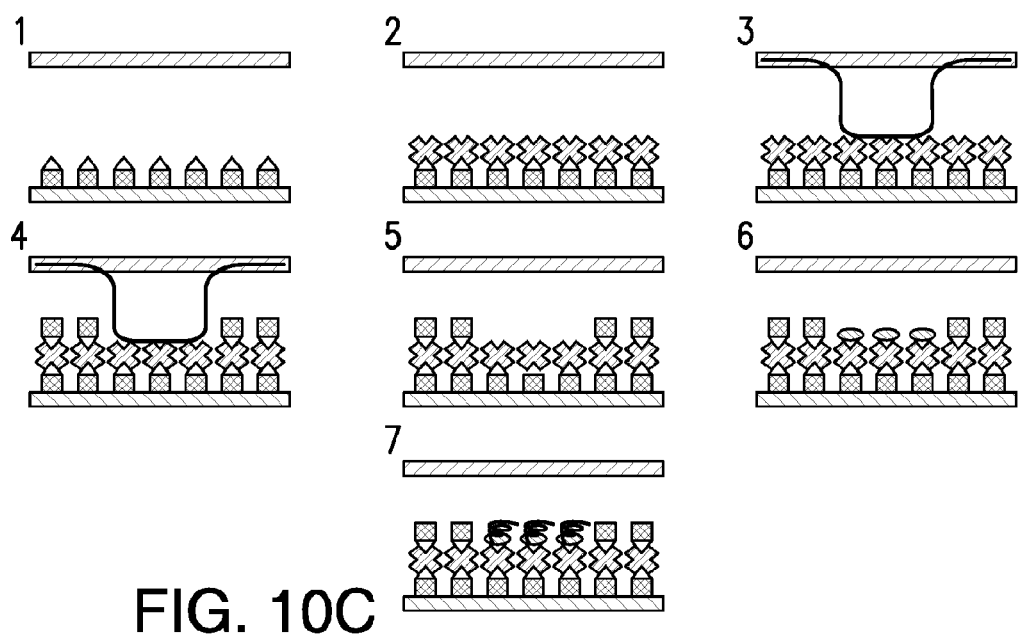

To test the hypothesis that AAK1 and GAK are important for HIV infection, HeLa-derived TZM-b1 cells were used, which express CD4, CCR5 and CXCR4, as well as β-galactosidase and firefly luciferase reporter genes responsive to HIV transcription (Wei et al., *Antimicrobial agents and chemotherapy* 46:1896-1905, 2002). Cells were transfected with siRNAs targeting AAK1, GAK or a NT sequence followed by infection with the infectious HIV-1 NL4-3 clone (Adachi et al., *J Virol* 59:284-291, 1986), as described (Zhou et al., *Cell Host & Microbe* 4:495-504, 2008). Luciferase activity was measured at 96 hr postinfection. AAK1 and GAK depletion significantly inhibited HIV replication (FIG. 10). To test the effect of pharmacological inhibitors of AAK1 and GAK against HIV, HIV-1 infected HeLa-derived TZM-b1 cells were treated daily with serial dilutions of sunitinib, erlotinib or PKC-412 for 4 days followed by luciferase assays. A significant dose response antiviral effect was observed with no effect on viability (FIG. 10). EC$_{50}$ of erlotininb was 1.4±0.3 (P value-0.0058), sunitinib-0.8±0.4 (P value-0.1), and PKC-412-8.5±4 (P value-0.1). Since these studies were conducted 96 hr postinfection, they assessed all stages of infection from entry to release and spread (Zhou et al., *Cell Host & Microbe* 4:495-504, 2008), and therefore suggest that AAK1 and GAK are important for overall HIV replication.

Methods

Plasmids.

ORFs encoding AP2M1, GAK, AAK1, TFR, SPIRE, RAC1, ARPC, and NESI were picked from the Human ORFeome library of cDNA clones (Rual et al., *Genome research* 14, 2128-2135, 2004) (Open biosystems) and recombined into either pcDNA-Dest40 (for C-terminal V5-his tagging), pGLuc (for *Gaussia Princeps* luciferase fragment (Gluc) tagging) (Cassonnet et al., *Nat Methods* 8, 990-992, 2011), and/or pCherry (for mCherry fluorescence protein tagging) vectors using gateway technology (Invitrogen). ORFs encoding T7-tagged full length core and NS3 were amplified from described vectors (Blight et al., *Science* 290, 1972-1974, 2000) and ligated into pcDNA3.1 (Invitrogen). pFL-J6/JFH(p7-Rluc2A) (Murray et al., *J Virol* 81, 10220-10231, 2007) was a gift from Dr. C. M. Rice (Tscherne et al., *J Virol* 80, 1734-1741, 2006). The YXXΦ core mutations and AP2M1 mutations were introduced into these plasmids by site-directed mutagenesis (using the QuikChange kit (Stratagene)).

Antibodies and Compounds.

See Tables 1 and 2.

RNAi and Rescue of Gene Silencing.

40-100 nM individual or pooled siRNAs (FIG. 8) were transfected into cells using silMPORTER (Upstate, Millipore) 48 hr prior to HCV RNA electroporation. Five individual MISSION Lentiviral Transduction Particles (Sigma) harboring short hairpin RNAs (shRNAs) targeting various sites in the AP2M1 RNA and a control shRNA were used to transduce Huh-7.5 cells according to the manufacturer's protocol. RNAi reagents used in this study are summarized in Table 3. AP2M1 rescue was performed by transduction of Huh-7.5 cells stably depleted for AP2M1 with lentiviruses expressing shRNA-resistant AP2M1 48 hr prior to electroporation with HCV genome.

Microfluidics Affinity Assays.

Device fabrication and design were done essentially as described (Maerkl et al., *Science* 315, 233-237, 2007). V5-his-tagged human proteins and T7-tagged viral proteins were expressed off the chip by mammalian in vitro transcription/translation mixture (TNT) (Promega) (in the presence of microsomal membranes). The device was subjected to surface patterning, resulting in a circular area coated with biotinylated anti-his antibodies within each unit cell (Einav et al., *Nature Biotechnology* 26, 1019-1027, 2008; Gerber et al., *Nature methods* 6, 71-74, 2009). Protein-protein binding experiments were performed as described (Gerber et al., *Nature methods* 6, 71-74, 2009). Briefly, human bait proteins were loaded into the device and bound to the surface anti-his antibodies. Viral and human proteins were incubated in the chip and labeled with anti-T7-Cy3 and anti-V5-FITC antibodies, respectively. Interactions were trapped mechanically by MITOMI (Maerkl et al., *Science* 315, 233-237, 2007; Einav et al., *Nature Biotechnology* 26, 1019-1027, 2008; Gerber et al., *Nature methods* 6, 71-74, 2009). After a brief wash to remove untrapped unbound material, the trapped protein complexes were detected by an array scanner (Tecan). The ratio of bound viral prey to expressed human bait protein was calculated for each data point by measuring the ratio of median signal of Cy3 to median signal of FITC. Protein concentration in lysates were determined by quantitative western analysis against standard curves of T7-tagged proteins. Experiments were conducted at least three times, each time with >20 replicates. See FIG. 10 for a detailed protocol.

Cell Cultures.

Huh-7.5 cells and 293T cells were maintained in Dulbecco's modified minimal essential medium (Gibco) supplemented with 1% L-glutamine (Gibco), 1% penicillin, 1% streptomycin (Gibco), 1× nonessential amino acids (Gibco), and 10% fetal bovine serum (Omega Scientific). Cell lines were passaged three times a week after treatment with 0.05% trypsin-0.02% EDTA and seeding at a dilution of 1:4.

Protein-Fragment Complementation Assays.

Binding assays were performed essentially as described (Cassonnet et al., *Nat Methods.* 8, 990-992, 2011). Combinations of plasmids encoding prey (A) and bait (B) proteins, each fused to a fragment of the *Gaussia Princeps* luciferase protein (Gluc1 and Gluc2) or control vectors were cotransfected into 293T or Huh-7.5 cells plated in 96-well plates in triplicates. At 24 hr posttransfection, cells were lysed and subjected to standard luciferase reporter gene assays using *Renilla* luciferase assays system (Promega). Results were expressed either as luminescence or luminescence ratio. The latter represents the average luminescence signal detected in cells transfected with Gluc1-A and Gluc2-B divided by the average of luminescence measured in control wells transfected with Gluc1-A and an empty Gluc2 vector with those transfected with Gluc2-B and an empty Gluc1 vector. Competition assays and studies designed to determine inhibitory effect of compounds or siRNAs were performed as above, except that binding was measured in the presence of excess free proteins, the inhibitors, or siRNAs, respectively. Experiments were conducted at least three times in triplicates.

Co-Immunoprecipitations.

Membranes were prepared from ~20×10$^6$ Huh-7.5 cells infected with HCV (J6/JFH) (Lindenbach, et al., *Science* 309, 623-626, 2005), as previously described (Einav et al., *J Virol* 78, 11288-11295, 2004). Briefly, cells were collected by trypsinization, washed once with PBS and resuspended in HME buffer (20 mM HEPES [pH 7.4], 1 mM EDTA, 2 mM MgCl2), supplemented with phenylmethylsulfonyl fluoride to a final concentration of 1 mM and a protease inhibitors cocktail (Sigma). Cells were lysed by two cycles of freeze-thaw in dry ice-ethanol and then passaged through a 27.5-gauge needle 10 times. Nuclei were removed by centrifugation at 250×g for 10 min, and the postnuclear supernatant was subjected to ultracentrifugation at 100,000×g for 30 min to obtain the membrane preparation. All steps were done at 4° C. Total membrane proteins were diluted in 1 ml TDB buffer (2.5% Triton X-100, 25 mM triethanolamine-Cl [pH 8.6], 20 mM NaCl, 5 mM EDTA, 0.2% NaN3) (Einav et al., *J Virol* 78, 11288-11295, 2004) and incubated for 30 min at 37° C. with 100 nM calyculin-A or DMSO. Due to the weak and transient nature of the interactions, 25 mM dithiobis-succinimidyl-propionate (DSP) cross-linker (Pierce) was added to allow covalent binding of the already bound interacting proteins. Samples were incubated for 2 hr on ice. 1 M Tris was added to stop the DSP activity. Lysates were then clarified by 10 min centrifugation at 1000×g, followed by 30 min ultracentrifugation of the supernatants at 100,000×g. Membrane pellets were resuspended in 100 ml HME buffer (20 mM NaHEpes (PH 7.4), 1 mM EDTA (Ph 8), 2 mM MgCl2), and TDB buffer was added for a final volume of 1 ml. Samples were incubated overnight with either anti-AP2M1 antibodies, anti-core antibodies or IgG controls, and protein G magnetic beads (Millipore). Immunoprecipitates were analyzed by western blotting. Experiments were conducted twice in duplicates.

In Vitro Transcription of Viral RNA and Transfection.

HCV RNA was generated and delivered into Huh-7.5 cells, as previously described (Lindenbach et al., *Science* 309, 623-626, 2005; Murray et al., *J Virol* 81, 10220-10231, 2007). Briefly, RNA was synthesized from XbaI linearized J6/JFH(p7-Rluc2A) template using the T7 MEGAscript kit according to the manufacturer's protocol (Ambion). Reaction mixtures were incubated for 3 hr at 37° C. and then subjected to DNase treatment for 15 min at 37° C. Viral RNA was purified using the RNeasy kit (Qiagen). RNA was quantified by absorbance at 260 nm, and its quality was verified by agarose gel electrophoresis. Subconfluent Huh-7.5 cells were trypsinized and collected by centrifugation at 700 g for 5 min. The cells were then washed three times in ice-cold RNase-free PBS (BioWhittaker) and resuspended at 1.5*10$^7$ cells/ml in PBS. 5 µg of the in vitro transcribed wild type or J6/JFH(p7-Rluc2A) mutant RNA was mixed with 400 µl of washed Huh-7.5 cells in a 2 mm-gap cuvette (BTX) and immediately pulsed (0.82 kV, five 99 µs pulses) with a BTX-830 electroporator. After a 15 min recovery at 25° C., cells were diluted in 30 ml of prewarmed growth medium and plated into 96, 24, 6-well and P100 tissue culture plates.

HCV RNA Replication by Luciferase Assays.

HCV RNA replication was measured at 6-9 hr, and 72 hr postelectroporation, as described (Murray et al., *J Virol* 81, 10220-10231, 2007). Electroporated cells plated in quadruplicates in 96-well plates were washed twice with PBS and lysed with 30 µl of *Renilla* lysis buffer (Promega). Following 15 min of shaking at RT, luciferase activity was quantified using a *Renilla* luciferase substrate (Promega) and a Tecan luminometer (Tecan) according to the manufacturers' protocols.

HIV Replication Assays.

HeLa-derived TZM-b1 cells, which express CD4, CCR5 and CXCR4, as well as β-galactosidase and firefly luciferase reporter genes responsive to HIV transcription (Wei et al., *Antimicrobial agents and chemotherapy* 46, 1896-1905, 2002) were used in these assays. Cells were transfected with siRNAs targeting AAK1, GAK or a NT sequence followed by infection with the infectious HIV-1 NL4-3 clone (Adachi et al., *J Virol* 59, 284-291, 1986), as described (Zhou et al., *Cell Host & Microbe* 4, 495-504, 2008). Luciferase activity was measured at 96 hr postinfection. To test the effect of pharmacological inhibitors of AAK1 and GAK against HIV, HIV-1 infected HeLa-derived TZM-b1 cells were treated daily with serial dilutions of sunitinib, erlotinib or PKC-412 for 4 days followed by luciferase assays.

Extracellular Infectivity.

Culture supernatants of Huh-7.5 cells electroporated with J6/JFH(p7-Rluc2A) RNA and plated in P100 dishes were harvested at 72 hr postelectroporation, clarified (with a 0.22-µm-pore size filter) and used to infect naïve Huh-7.5 cells for 72 hr in triplicates before lysis in *Renilla* lysis buffer (Promega). Luciferase activity in 20 µl of cell lysates was quantified as described above. To determine the effect of erlotinib, sunitinib, and PKC-412 on infectious virus production, electroporated cells were grown in the presence of the inhibitors with daily medium changes for 72 hr prior to collection of supernatants or cell lysates. Results represent log 10 RLU values per 10 cm tissue culture dish. Experiments were repeated three times, each time with quadruplicates.

Intracellular Infectivity Assays.

As described by Murray et al. (*J Virol* 81, 10220-10231, 2007), 72 hr postelectroporation with J6/JFH(p7-Rluc2A) RNA cells were trypsinized, collected by centrifugation, resuspended in 500 µl medium, lysed by freeze-thaw cycles, and pelleted twice at 3,650×g. Clarified supernatants diluted in complete medium were used to inoculate naive Huh-7.5 cells in triplicates, followed by lysis and luciferase assays at 72 hr. Results represent log 10 RLU values per 10 cm tissue culture dish. Experiments were repeated three times, each time with quadruplicates.

Virus Titration.

Extracellular and Intracellular titers were determined by limiting dilution assays based on immunohistochemical staining for core. 50% tissue culture infectious dose ($TCID_{50}$) was calculated, as described (Lindenbach et al., *Science* 309, 623-626, 2005). Results are expressed as $TCID_{50}$/ml. Minimal titers measured with the ΔE1-E2 mutant were used for background subtraction.

Core ELISA.

The concentration of released core protein was measured in clarified cell culture supernatants harvested at 72 hr postelectroporation by ELISA (Cell Biolabs) against standard curves of recombinant core antigen, according to the manufacturer's instructions.

Viability Assays.

Following 24, 48, and 72 hrs of treatment with inhibitory compounds or silencing with siRNAs, cells were incubated for 2-4 hrs at 37° C. in the presence of 10% AlamarBlue reagent (TREK Diagnostic Systems), as described (Einav et al., *Nature Biotechnology* 26, 1019-1027, 2008). Plates were then scanned and fluorescence was detected by using FLEXstation II 384 (Molecular Devices, Inc.).

Infection Studies.

$6 \times 10^3$ Huh-7.5 cells seeded in 96-well plates were infected in triplicates with cell culture-grown HCV J6/JFH (titer: $1.2 \times 10^5$ $TCID_{50}$/ml). Extracellular and intracellular infectivity were measured by focus formation assays (Lindenbach et al., *Science* 309, 623-626, 2005) in naive Huh-7.5 cells infected with supernatants or clarified cell lysates derived from the infected cells at 72 hr postinfection.

To determine the antiviral effect of erlotinib, sunitinib, and PKC-412, $6 \times 10^3$ Huh-7.5 cells seeded in 96-well plates were infected in triplicates with cell culture-grown HCV (J6/JFH(p7-Rluc2A)) (titer: $6.3 \times 10^5$ $TCID_{50}$/ml) with an MOI (multiplicity of infection) of 0.1. Six hours after infection and daily thereafter, cells were washed and medium was replaced with medium containing serial dilutions of the inhibitory compounds. At 72 hr, samples were subjected to viability assays, followed by standard luciferase assays (Promega).

Analysis of Revertants.

Huh-7.5 cells electroporated with J6/JFH(p7-Rluc2A) harboring the Y136A or V139A mutations were propagated. Culture supernatants were harvested every few days and used to inoculate naive Huh-7.5 cells for determination of extracellular infectivity by luciferase assays 72 hr following inoculation. Total cellular RNA was extracted from clones demonstrating reversion of the infectivity phenotypone (at day 8 postelectroporation for Y136A clones and day 14 for V139A mutant clones) using TRIzol reagent (Invitrogen). Reverse transcription reaction and PCR amplification were performed using Superscript One-Step reverse transcriptase PCR (RT-PCR) kit (Invitrogen). A ~1-kb segment harboring the core coding sequence was amplified. The PCR products were purified from agarose gels by Ultra Clean 15 DNA purification kit (MoBio) and subjected to automatic sequencing on an ABI Prism 377 DNA sequencer (Sequetech). Presence of primary site reversion was confirmed by two independent sequences using forward and reverse oligos.

RNA Extraction and qRT-PCR.

Total RNA was isolated from cells or 1 ml cell culture supernatants using TRIzol (Invitrogen) or QiaAmp UltraSens kit (Qiagen), respectively. qRT-PCRs mixtures were assembled in triplicates using 0.5 µg or 4 µl RNA and High-Capacity RNA-to-cDNA (Applied Biosystems). TaqMan reagents are listed in Table 4. Amplification and analysis were performed using StepOnePlus Real-Time-PCR system (Applied Biosystems). S18 was used as a control.

Western Blot.

Cell lysates were subjected to western analyses using primary antibodies followed by HRP-conjugated secondary antibodies. Bands intensity was quantified using NIH Image.

Quantitative Immunofluorescence Confocal Microscopy.

Huh-7.5 cells were electroporated with J6/JFH HCV RNA or infected with culture grown J6/JFH virus, seeded onto coverslips, and incubated for 72 hr at 37° C. Cells were fixed with 4% paraformaldehyde in PBS, washed with PBS, permeabilized with 0.1% Triton X-100 in PBS for 5 min, and blocked for 1 hr in PBS containing 1% BSA. Fixed cells were incubated with primary antibodies against either the core protein, AP2M1, TGN46, calreticulin or E2 at room temperature for 1 hr (see Table 1). Secondary antibodies (goat anti-rabbit Alexa Fluor 488, goat anti-mouse Alexa Fluor 594, chicken anti-goat IgG Alexa Fluor 647, and goat anti-human Alexa Fluor 647) (Invitrogen) were incubated for 1 hr at room temperature. LD staining with Bodipy-488/503 (Invitrogen) was performed as described (Kopp et al., *J Virol* 84, 1666-1673, 2010). Cover slips were then washed three times in PBS, and mounted with ProLong Gold antifade reagent (Invitrogen). Alternatively, Huh-7.5 cells were co-transfected with plasmids expressing AP2M1-YFP and/or Core-mCherry. LD were stained with HCS LipidTOX (Invitrogen). All slides were analyzed using Zeiss LSM 510 confocal microscope. Colocalization was quantified in 10-15 randomly chosen cells from each sample using ImageJ (JACoP) colocalization Software and Manders' Colocalization Coefficients (MCC). Threshold values were determined using auto threshold (plugin, ImageJ). Only pixels whose red and green intensity values were both above their respective thresholds were considered to be pixels with colocalized probes. MCCs were then calculated as the fractions of total fluorescence in the region of interest that occurs in these "colocal" pixels (with a higher value representing more colocalization). M2 coefficient values represented as mean percent colocalization are shown.

Statistical Analysis.

IC50s and EC50s were measured by fitting data to a three parameter logistic curve, as described (Einav et al., *Nature Biotechnology* 26, 1019-1027, 2008). P-values were calculated using one-tailed unpaired Student's t test.

Example 3

The Effect of Erlotinib, Sunitinib, and PKC-412 on AP2M1 Phosphorylation

To determine the effect of the inhibitory compounds on AP2M1 phosphorylation, Huh-7.5 cells harboring J6/JFH (p7-Rluc2A) RNA were treated daily with various concentrations of the compounds or with DMSO. Since AP2M1 phosphorylation is transient (due to the activity of the phosphatase PP2A (Ricotta et al., *J Biol Chem* 283:5510-5517, 2008), to allow capturing of the phosphorylated AP2M1 state, lysates were prepared at 72 hr following a 30 min incubation of the cells with 100 nM of the PP2A inhibitor, calyculin A (Cal-A) or a DMSO control. Samples were then subjected to SDS-PAGE and blotting with antibodies targeting either the phosphorylated AP2M1 form or actin. Indeed, significantly lower ratios of phosphorylated-AP2M1 to actin were measured in lysates prepared from cells treated with either sunitinib, erlotinib or PKC-412, compared with the DMSO control (FIG. 6H). Phospho-AP2M1 to actin ratios were progressively decreased by increasing concentrations of sunitinib and erlotinib in a dose-dependent manner. These results suggest that AAK1 or GAK are potently inhibited by these compounds in Huh-7.5 cells harboring infectious HCV.

The Effect of the Compounds on HCV RNA Replication, Intracellular Infectivity, Extracellular Infectivity, and HCV Replication.

To determine the effect of erlotinib, sunitinib, and PKC-412 on infectious virus production, Huh-7.5 cells were electroporated with J6/JFH(p7-Rluc2A) HCV genome (Murray et al., *J Virol* 81:10220-10231, 2007), plated in 6-well plates, and treated daily with serial dilutions of the compounds or DMSO. At 72 hr postelectroporation, cellular viability was measured by alamarBlue-based assays followed by luciferase assays for determination of HCV RNA replication. Cell culture supernatants and lysates were collected at 72 hr from parallel samples and used to inoculate naive Huh-7.5 cells for determination of extracellular and intracellular infectivity, respectively. Luciferase assays were performed in these cells at 72 hr post inoculation.

To determine the effect of these compounds on HCV replication, $6 \times 10^3$ Huh-7.5 cells seeded in 96-well plates were infected in triplicates with cell culture-grown HCV (J6/JFH(p7-Rluc2A)) tittered at $6.3 \times 10^5$ TCID$_{50}$/ml with an MOI (multiplicity of infection) of 0.1. At 6 hr postelectroporation, cells were washed and medium was replaced with serial dilutions of the inhibitory compounds. Cells were treated daily for 72 hr and then subjected to viability assays followed by standard luciferase assays.

Alternatively, $6 \times 10^3$ Huh-7.5 cells seeded in 96-well plates were infected in triplicates with cell culture-grown HCV J6/JFH (titer: $1.2 \times 10^5$ TCID$_{50}$/ml with an MOI of 0.1, and subjected to focus formation assays, as described (Lindenbach et al., *Science* 309:623-626, 2005). Following 72 hr of daily treatment with the compounds, cells were fixed in 4% formaldehyde and permeabilized with saponin. HCV core protein was detected with primary anti-core monoclonal and secondary goat anti-mouse Alexa 594-conjugated antibodies. Foci were counted under an inverted microscope.

Experiments were repeated twice, each with 4 replicates. Signal was normalized to samples grown in the presence of the corresponding concentration of DMSO. EC50s were measured by fitting data to a three parameter logistic curve using the formula $Y=a+(b-a)/(1+10^{\wedge}(X-c))$ (a, b and c represent minimum binding, maximum binding and logEC50, respectively)(BioDataFit, Chang Bioscience, Inc).

TABLE 1

Antibodies used in this study

| Antibodies | Source |
| --- | --- |
| Biotinylated anti-penta-his | Qiagen |
| FITC-conjugated anti-V5 | Invitrogen |
| Phycoerythrin-conjugated anti-T7 tag | Abcam |
| Rabbit Anti-AAK1 | Abcam |
| Rabbit anti-AP2M1 | Santa Cruz Biotechnology |
| Goat anti-AP2M1 | Santa Cruz Biotechnology |
| Rabbit anti-phospho-AP2M1 (T156) | Cell signaling |
| Rabbit anti-TGN46 | Abcam |
| Rabbit anti-calreticulin | Enzo Life Sciences |
| Mouse anti-GAK | MBL international corporation |
| Mouse anti-core | Austral Biologicals |
| Human anti-E2 (CBH5) | Dr. Steven K Foung |
| Mouse anti-actin | Sigma |
| HRP-conjugated anti-mouse IgG | Cell signaling |
| HRP-conjugated anti-rabbit IgG | Cell signaling |

TABLE 2

Compounds used in this study

| Compound | Source |
| --- | --- |
| PKC-412 | Sigma |
| Sunitinib malate | Sigma |
| Erlotinib | LC Laboratories |
| Calyculin A | Cell Signaling |

TABLE 3

RNAi used in this study

| RNAi type | Target | Catalogue# | Source | Sequence |
| --- | --- | --- | --- | --- |
| ON-TARGETplus SMARTpools | AP2M1 | LQ-008170-00-0002 | Dharmacon | |
| | AP2M1 | J-004233-05 | Dharmacon | GUUAAGCGGUCCAACAUUU |
| | AP2M1 | J-004233-06 | Dharmacon | GCGAGAGGGUAUCAAGUAU |
| | AP2M1 | J-004233-07 | Dharmacon | AGUUUGAGCUUAUGAGGUA |
| | AP2M1 | J-004233-08 | Dharmacon | GAACCGAAGCUGAACUACA |
| | Non-targeting | D-001810-10-05 | Dharmacon | Non Available |
| siRNAs | AAK1 | Ref #4 | Ambion | GGUGUGCAAGAGAGAAAUCtt |
| | GAK | Ref #5 | Dharmacon | AACGAAGGAACAGCUGAUUCA |
| | Non-targeting | D-001210-01-05 | Dharmacon | Non Available |
| MISSION shRNAs | AP2M1 | TRCN0000060238 ("238") | Sigma | CCGGGTGGTCATCAAGTCCAACTTTCTCGA GAAAGTTGGACTTGATGACCACTTTTTG |
| | AP2M1 | TRCN0000060239 ("239") | Sigma | CCGGCACCAGCTTCTTCCACGTTAACTCGA GTTAACGTGGAAGAAGCTGGTGTTTTTG |

TABLE 3-continued

RNAi used in this study

| RNAi type | Target | Catalogue# | Source | Sequence |
|---|---|---|---|---|
| | AP2M1 | TRCN0000060241 ("241") | Sigma | CCGGGCTGGATGAGATTCTAGACTTCTCGA GAAGTCTAGAATCTCATCCAGCTTTTTG |
| | AP2M1 | TRCN0000060242 ("242") | Sigma | CCGGCATTTATGAAACTCGCTGCTACTCGAG TAGCAGCGAGTTTCATAAATGTTTTTG |
| | Non-targeting | SHC002V | Sigma | Non Available |

TABLE 4

Taqman probes and primers used in this study

| Primer name | Sequence or assay catalogue # |
|---|---|
| HCV Forward | CTTCACGCAGAAAGCGTCTA |
| HCV Reverse | CAAGCACCCTATCAGGCAGT |
| HCV Taqman MGB probe | [6FAM]-TATGAGTGTCGTGCAGCCTC-[MGB-NFQ] |
| AP2M1 | HS01037584_m1 |
| GAK | HS00178347_m1 |
| AAK1 | HS00208618_m1 |
| S18 | hs999999_m1 |

All reagents listed in this table were purchased from Applied Biosystems, Inc (ABI).

The invention claimed is:

1. A method of inhibiting assembly or budding of Dengue virus, comprising contacting a host cell that is infected with Dengue virus with sunitinib or a pharmaceutically acceptable salt of sunitinib, wherein the sunitinib inhibits adaptor-associated kinase 1 (AAK1), thereby inhibiting assembly or budding of the Dengue virus.

2. The method of claim 1, wherein said sunitinib or pharmaceutically acceptable salt of sunitinib blocks binding of a viral structural protein to a host protein.

3. The method of claim 1, wherein said sunitinib or pharmaceutically acceptable salt of sunitinib competes with a viral structural protein for binding to a host protein.

4. The method of claim 1, wherein said sunitinib or pharmaceutically acceptable salt of sunitinib competes with a host protein for binding to a viral structural protein.

5. The method of claim 1, further comprising contacting said host cell with erlotinib, midostaurin, or a pharmaceutically acceptable salt or combination thereof.

6. The method of claim 5, wherein the host cell is contacted with erlotinib or a pharmaceutically acceptable salt of erlotinib.

7. The method of claim 5, wherein the host cell is contacted with midostaurin or a pharmaceutically acceptable salt of midostaurin.

8. The method of claim 1, wherein assembly or budding of said Flaviviridae is inhibited.

* * * * *

SEQUENCE LISTING

<160> NUMBER OF SEQ ID NOS: 13

<210> SEQ ID NO 1
<211> LENGTH: 19
<212> TYPE: RNA
<213> ORGANISM: Artificial sequence
<220> FEATURE:
<223> OTHER INFORMATION: RNAi

<400> SEQUENCE: 1
guuaagcggu ccaacauuu                                                19

<210> SEQ ID NO 2
<211> LENGTH: 19
<212> TYPE: RNA
<213> ORGANISM: Artificial sequence
<220> FEATURE:
<223> OTHER INFORMATION: RNAi

<400> SEQUENCE: 2
gcgagagggu aucaaguau                                                19

<210> SEQ ID NO 3
<211> LENGTH: 19
<212> TYPE: RNA
<213> ORGANISM: Artificial sequence
<220> FEATURE:
<223> OTHER INFORMATION: RNAi

<400> SEQUENCE: 3
aguuugagcu uaugaggua                                                19

<210> SEQ ID NO 4
<211> LENGTH: 19
<212> TYPE: RNA
<213> ORGANISM: Artificial sequence
<220> FEATURE:
<223> OTHER INFORMATION: RNAi

<400> SEQUENCE: 4

```
gaaccgaagc ugaacuaca                                                    19

<210> SEQ ID NO 5
<211> LENGTH: 21
<212> TYPE: DNA
<213> ORGANISM: Artificial sequence
<220> FEATURE:
<223> OTHER INFORMATION: siRNA
<220> FEATURE:
<221> NAME/KEY: misc_feature
<222> LOCATION: (20)..(21)
<223> OTHER INFORMATION: Two thymine residues at the end of an RNA
      sequence

<400> SEQUENCE: 5
ggugugcaag agagaaauct t                                                 21

<210> SEQ ID NO 6
<211> LENGTH: 21
<212> TYPE: RNA
<213> ORGANISM: Artificial sequence
<220> FEATURE:
<223> OTHER INFORMATION: siRNA

<400> SEQUENCE: 6
aacgaaggaa cagcugauuc a                                                 21

<210> SEQ ID NO 7
<211> LENGTH: 58
<212> TYPE: DNA
<213> ORGANISM: Artificial sequence
<220> FEATURE:
<223> OTHER INFORMATION: shRNA

<400> SEQUENCE: 7
ccgggtggtc atcaagtcca actttctcga gaaagttgga cttgatgacc acttttg          58

<210> SEQ ID NO 8
<211> LENGTH: 58
<212> TYPE: DNA
<213> ORGANISM: Artificial sequence
<220> FEATURE:
<223> OTHER INFORMATION: shRNA

<400> SEQUENCE: 8
ccggcaccag cttcttccac gttaactcga gttaacgtgg aagaagctgg tgttttg          58

<210> SEQ ID NO 9
<211> LENGTH: 58
<212> TYPE: DNA
<213> ORGANISM: Artificial sequence
<220> FEATURE:
<223> OTHER INFORMATION: shRNA

<400> SEQUENCE: 9
ccgggctgga tgagattcta gacttctcga gaagtctaga atctcatcca gcttttg          58

<210> SEQ ID NO 10
<211> LENGTH: 58
<212> TYPE: DNA
<213> ORGANISM: Artificial sequence
<220> FEATURE:
<223> OTHER INFORMATION: shRNA

<400> SEQUENCE: 10
ccggcattta tgaaactcgc tgctactcga gtagcagcga gtttcataaa tgttttg          58
```

-continued

```
<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
cttcacgcag aaagcgtcta                                               20

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
caagcaccct atcaggcagt                                               20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
tatgagtgtc gtgcagcctc                                               20
```